(12) United States Patent
Bullington et al.

(10) Patent No.: US 12,083,234 B2
(45) Date of Patent: Sep. 10, 2024

(54) APPARATUS AND METHODS FOR MAINTAINING STERILITY OF A SPECIMEN CONTAINER

(71) Applicant: Magnolia Medical Technologies, Inc., Seattle, WA (US)

(72) Inventors: Gregory J. Bullington, Seattle, WA (US); Shan E. Gaw, Seattle, WA (US); Jay M. Miazga, Langley, WA (US); Skooks Pong, Kirkland, WA (US); Shannon E Eubanks, Woodinville, WA (US)

(73) Assignee: Magnolia Medical Technologies, Inc., Seattle, WA (US)

( * ) Notice: Subject to any disclaimer, the term of this patent is extended or adjusted under 35 U.S.C. 154(b) by 944 days.

(21) Appl. No.: 16/815,521

(22) Filed: Mar. 11, 2020

(65) Prior Publication Data

US 2020/0215211 A1     Jul. 9, 2020

Related U.S. Application Data

(60) Continuation of application No. 15/925,159, filed on Mar. 19, 2018, now Pat. No. 10,624,977, which is a
(Continued)

(51) Int. Cl.
*A61B 5/15*        (2006.01)
*A61B 5/154*      (2006.01)
(Continued)

(52) U.S. Cl.
CPC ........ *A61L 2/0082* (2013.01); *A61B 5/15003* (2013.01); *A61B 5/150351* (2013.01);
(Continued)

(58) Field of Classification Search
None
See application file for complete search history.

(56) References Cited

U.S. PATENT DOCUMENTS

| 2,707,953 A | 5/1955 | Ryan |
| 2,992,974 A | 7/1961 | Belcove et al. |
| (Continued) | | |

FOREIGN PATENT DOCUMENTS

| AT | 310345 B | 9/1973 |
| BR | 112012025546 A2 | 6/2016 |
| (Continued) | | |

OTHER PUBLICATIONS

Arkin, C. F. et al., "Procedures for the Collection of Diagnostic Blood Specimens by Venipuncture; Approved Standard," Fifth Edition, Clinical and Laboratory Standards Institute, vol. 23, No. 32 (2003), 52 pages.

(Continued)

*Primary Examiner* — Benjamin S Melhus
*Assistant Examiner* — Aurelie H Tu
(74) *Attorney, Agent, or Firm* — Cooley LLP

(57) ABSTRACT

An apparatus includes a fluid reservoir, a sterilization member, and a transfer adapter. The sterilization member operably couples to the fluid reservoir. The sterilization member is configured to be transitioned between a first configuration, in which the sterilization member obstructs an inlet surface of the fluid reservoir and maintains the inlet surface in a substantially sterile environment, and a second configuration, in which the inlet surface is unobstructed. The transfer adapter is configured to be placed in fluid communication with a portion of a patient. The transfer adapter is configured to move relative to the sterilization member from a first position to a second position such that a surface of the transfer adapter contacts the sterilization member to transi- (Continued)

tion the sterilization member to the second configuration. The fluid reservoir is placed in fluid communication with the transfer adapter when the transfer adapter is in the second position.

6 Claims, 19 Drawing Sheets

Related U.S. Application Data division of application No. 15/257,185, filed on Sep. 6, 2016, now Pat. No. 9,950,084.

(60) Provisional application No. 62/213,875, filed on Sep. 3, 2015.

(51) Int. Cl.
*A61B 5/155* (2006.01)
*A61L 2/00* (2006.01)
*B01L 3/00* (2006.01)

(52) U.S. Cl.
CPC .. *A61B 5/150732* (2013.01); *A61B 5/150992* (2013.01); *A61B 5/154* (2013.01); *A61B 5/155* (2013.01); *B01L 3/502* (2013.01); *B01L 3/50825* (2013.01); *B01L 3/5635* (2013.01); *A61B 5/150389* (2013.01); *A61B 5/150503* (2013.01); *A61L 2202/121* (2013.01); *A61L 2202/15* (2013.01); *A61L 2202/22* (2013.01); *B01L 2200/026* (2013.01); *B01L 2200/141* (2013.01); *B01L 2300/042* (2013.01); *B01L 2300/044* (2013.01); *B01L 2300/0672* (2013.01)

(56) References Cited

U.S. PATENT DOCUMENTS

| | | |
|---|---|---|
| 3,013,557 A | 12/1961 | Pallotta |
| 3,098,016 A | 7/1963 | Sam et al. |
| 3,382,865 A | 5/1968 | Worrall, Jr. et al. |
| 3,405,706 A * | 10/1968 | Cinqualbre ...... A61B 5/150305 600/577 |
| 3,467,021 A | 9/1969 | Green, Jr. et al. |
| 3,467,095 A | 9/1969 | Ross et al. |
| 3,494,351 A | 2/1970 | Horn et al. |
| 3,494,352 A | 2/1970 | Russo et al. |
| 3,577,980 A | 5/1971 | Cohen |
| 3,596,652 A | 8/1971 | Winkelman |
| 3,604,410 A | 9/1971 | Whitacre |
| 3,635,798 A | 1/1972 | Kirkham et al. |
| 3,640,267 A | 2/1972 | Hurtig et al. |
| 3,648,684 A | 3/1972 | Barnwell et al. |
| 3,680,558 A | 8/1972 | Kapelowitz |
| 3,696,806 A | 10/1972 | Sausse et al. |
| 3,730,168 A | 5/1973 | Mcwhorter |
| 3,741,197 A | 6/1973 | Sanz et al. |
| 3,777,773 A | 12/1973 | Tolbert |
| 3,803,810 A | 4/1974 | Rosenberg |
| 3,817,240 A | 6/1974 | Ayres |
| 3,831,602 A | 8/1974 | Broadwin |
| 3,834,372 A | 9/1974 | Turney |
| 3,835,835 A | 9/1974 | Thompson et al. |
| 3,848,579 A | 11/1974 | Villa-Real |
| 3,848,581 A | 11/1974 | Cinqualbre et al. |
| 3,859,998 A | 1/1975 | Thomas et al. |
| 3,874,367 A | 4/1975 | Ayres |
| 3,886,930 A | 6/1975 | Ryan |
| 3,890,203 A | 6/1975 | Mehl |
| 3,890,968 A | 6/1975 | Pierce et al. |
| 3,937,211 A | 2/1976 | Merten |
| 3,945,380 A | 3/1976 | Dabney et al. |
| 3,960,139 A | 6/1976 | Bailey |
| 3,978,846 A | 9/1976 | Bailey |
| 3,996,923 A | 12/1976 | Guerra |
| 4,056,101 A | 11/1977 | Geissler et al. |
| 4,057,050 A | 11/1977 | Sarstedt |
| 4,063,460 A | 12/1977 | Svensson |
| 4,077,395 A | 3/1978 | Woolner |
| 4,106,497 A | 8/1978 | Percarpio |
| 4,133,863 A | 1/1979 | Koenig |
| 4,150,089 A | 4/1979 | Linet |
| 4,154,229 A | 5/1979 | Nugent |
| 4,166,450 A | 9/1979 | Abramson |
| 4,190,426 A | 2/1980 | Ruschke |
| 4,193,400 A | 3/1980 | Loveless et al. |
| 4,207,870 A | 6/1980 | Eldridge |
| 4,210,173 A | 7/1980 | Choksi et al. |
| 4,212,308 A | 7/1980 | Percarpio |
| 4,238,207 A | 12/1980 | Ruschke |
| 4,257,416 A | 3/1981 | Prager |
| 4,298,358 A | 11/1981 | Ruschke |
| 4,312,362 A | 1/1982 | Kaufman |
| 4,327,746 A | 5/1982 | Feaster |
| 4,340,067 A | 7/1982 | Rattenborg |
| 4,340,068 A | 7/1982 | Kaufman |
| 4,349,035 A | 9/1982 | Thomas et al. |
| 4,354,507 A | 10/1982 | Raitto |
| 4,370,987 A | 2/1983 | Bazell et al. |
| 4,373,535 A | 2/1983 | Martell |
| 4,411,275 A | 10/1983 | Raitto |
| 4,412,548 A | 11/1983 | Hoch |
| 4,425,235 A | 1/1984 | Cornell et al. |
| 4,436,098 A | 3/1984 | Kaufman |
| 4,444,203 A | 4/1984 | Engelman |
| 4,459,997 A | 7/1984 | Sarstedt |
| 4,509,534 A | 4/1985 | Tassin, Jr. |
| 4,608,996 A | 9/1986 | Brown |
| 4,626,248 A | 12/1986 | Scheller |
| 4,654,027 A | 3/1987 | Dragan et al. |
| 4,657,027 A | 4/1987 | Paulsen |
| 4,657,160 A | 4/1987 | Woods et al. |
| 4,673,386 A | 6/1987 | Gordon |
| 4,676,256 A | 6/1987 | Golden |
| 4,690,154 A | 9/1987 | Woodford et al. |
| 4,699,612 A | 10/1987 | Hamacher |
| 4,705,497 A | 11/1987 | Shitaokoshi et al. |
| 4,715,854 A | 12/1987 | Vaillancourt |
| 4,838,855 A | 6/1989 | Lynn |
| 4,865,583 A | 9/1989 | Tu |
| 4,879,098 A | 11/1989 | Oberhardt et al. |
| 4,886,072 A | 12/1989 | Percarpio et al. |
| 4,890,627 A | 1/1990 | Haber et al. |
| 4,904,240 A | 2/1990 | Hoover |
| 4,936,315 A | 6/1990 | Lineback |
| 4,980,297 A | 12/1990 | Haynes et al. |
| 4,988,339 A | 1/1991 | Vadher |
| 5,027,827 A | 7/1991 | Cody et al. |
| 5,045,185 A | 9/1991 | Ohnaka et al. |
| 5,052,403 A | 10/1991 | Haber et al. |
| 5,084,034 A | 1/1992 | Zanotti |
| 5,097,842 A | 3/1992 | Bonn |
| 5,100,394 A | 3/1992 | Dudar et al. |
| 5,108,927 A | 4/1992 | Dorn |
| 5,122,129 A | 6/1992 | Olson et al. |
| 5,135,489 A | 8/1992 | Jepson et al. |
| 5,222,502 A | 6/1993 | Kurose |
| 5,269,317 A | 12/1993 | Bennett |
| 5,330,464 A | 7/1994 | Mathias et al. |
| 5,334,162 A | 8/1994 | Harris |
| 5,354,537 A | 10/1994 | Moreno |
| 5,360,011 A | 11/1994 | McCallister |
| 5,395,339 A | 3/1995 | Talonn et al. |
| 5,417,673 A | 5/1995 | Gordon |
| 5,429,610 A | 7/1995 | Vaillancourt |
| 5,431,811 A | 7/1995 | Tusini et al. |
| 5,439,450 A | 8/1995 | Haedt |
| 5,450,856 A | 9/1995 | Norris |
| 5,454,786 A | 10/1995 | Harris |
| 5,466,228 A | 11/1995 | Evans |
| 5,472,605 A | 12/1995 | Zuk, Jr. |
| 5,485,854 A | 1/1996 | Hollister |

(56) References Cited

U.S. PATENT DOCUMENTS

| | | |
|---|---|---|
| 5,507,299 A | 4/1996 | Roland |
| 5,520,193 A | 5/1996 | Suzuki et al. |
| 5,522,804 A | 6/1996 | Lynn |
| 5,573,510 A | 11/1996 | Isaacson |
| 5,577,513 A | 11/1996 | Van Vlasselaer |
| 5,603,700 A | 2/1997 | Daneshvar |
| 5,632,906 A | 5/1997 | Ishida et al. |
| 5,649,912 A | 7/1997 | Peterson |
| 5,658,271 A | 8/1997 | Loubser |
| 5,691,486 A | 11/1997 | Behringer et al. |
| 5,749,857 A | 5/1998 | Cuppy |
| 5,759,160 A | 6/1998 | Neese et al. |
| 5,762,633 A | 6/1998 | Whisson |
| 5,772,608 A | 6/1998 | Dhas |
| 5,785,682 A | 7/1998 | Grabenkort |
| 5,811,658 A | 9/1998 | Van Driel et al. |
| 5,857,983 A | 1/1999 | Douglas et al. |
| 5,865,803 A | 2/1999 | Major |
| 5,865,812 A | 2/1999 | Correia |
| 5,871,699 A | 2/1999 | Ruggeri |
| 5,873,841 A | 2/1999 | Brannon |
| 5,876,926 A | 3/1999 | Beecham |
| 5,882,318 A | 3/1999 | Boyde |
| 5,922,551 A | 7/1999 | Durbin et al. |
| 5,961,472 A | 10/1999 | Swendson et al. |
| 5,971,956 A | 10/1999 | Epstein |
| 5,980,830 A | 11/1999 | Savage et al. |
| 6,001,307 A | 12/1999 | Naka et al. |
| 6,010,633 A | 1/2000 | Zuk, Jr. et al. |
| 6,013,037 A | 1/2000 | Brannon |
| 6,016,712 A | 1/2000 | Warden et al. |
| 6,050,957 A | 4/2000 | Desch |
| 6,106,509 A | 8/2000 | Loubser |
| 6,126,643 A | 10/2000 | Vaillancouert |
| 6,146,360 A | 11/2000 | Rogers et al. |
| 6,159,164 A | 12/2000 | Neese et al. |
| 6,210,909 B1 | 4/2001 | Guirguis |
| 6,224,561 B1 | 5/2001 | Swendson et al. |
| 6,254,581 B1 | 7/2001 | Scott |
| 6,306,614 B1 | 10/2001 | Romaschin et al. |
| 6,325,975 B1 | 12/2001 | Naka et al. |
| 6,328,726 B1 | 12/2001 | Ishida et al. |
| 6,355,023 B1 | 3/2002 | Roth et al. |
| 6,364,847 B1 | 4/2002 | Shulze et al. |
| 6,364,890 B1 | 4/2002 | Lum et al. |
| 6,368,306 B1 | 4/2002 | Koska |
| 6,387,086 B2 | 5/2002 | Mathias et al. |
| 6,403,381 B1 | 6/2002 | Mann et al. |
| 6,416,496 B1 | 7/2002 | Rogers et al. |
| 6,440,725 B1 | 8/2002 | Pourahmadi et al. |
| 6,478,775 B1 | 11/2002 | Galt et al. |
| 6,506,182 B2 | 1/2003 | Estabrook et al. |
| 6,511,439 B1 | 1/2003 | Tabata et al. |
| 6,520,948 B1 | 2/2003 | Mathias et al. |
| 6,569,117 B1 | 5/2003 | Ziv et al. |
| 6,592,555 B1 | 7/2003 | Wen-Pi et al. |
| 6,626,884 B1 | 9/2003 | Dillon et al. |
| 6,629,959 B2 | 10/2003 | Kuracina et al. |
| 6,638,252 B2 | 10/2003 | Moulton et al. |
| 6,648,835 B1 | 11/2003 | Shemesh |
| 6,692,479 B2 | 2/2004 | Kraus et al. |
| 6,695,004 B1 | 2/2004 | Raybuck |
| 6,712,963 B2 | 3/2004 | Schick |
| 6,716,187 B1 | 4/2004 | Jorgensen et al. |
| 6,716,396 B1 | 4/2004 | Anderson et al. |
| 6,733,433 B1 | 5/2004 | Fell |
| 6,736,783 B2 | 5/2004 | Blake et al. |
| 6,746,420 B1 | 6/2004 | Prestidge et al. |
| 6,843,775 B2 | 1/2005 | Hyun |
| 6,860,871 B2 | 3/2005 | Kuracina et al. |
| 6,905,483 B2 | 6/2005 | Newby et al. |
| 6,913,580 B2 | 7/2005 | Stone |
| 6,945,948 B2 | 9/2005 | Bainbridge et al. |
| 7,044,941 B2 | 5/2006 | Mathias et al. |
| 7,052,603 B2 | 5/2006 | Schick |
| 7,055,401 B2 | 6/2006 | Prybella et al. |
| 7,087,047 B2 | 8/2006 | Kraus et al. |
| 7,141,097 B2 | 11/2006 | Leahey |
| 7,241,281 B2 | 7/2007 | Coelho et al. |
| 7,306,736 B2 | 12/2007 | Collins et al. |
| 7,314,452 B2 | 1/2008 | Madonia |
| 7,316,662 B2 | 1/2008 | Delnevo et al. |
| 7,335,188 B2 | 2/2008 | Graf |
| 7,351,228 B2 | 4/2008 | Keane et al. |
| 7,384,416 B2 | 6/2008 | Goudaliez et al. |
| 7,435,231 B2 | 10/2008 | Mathias et al. |
| 7,461,671 B2 | 12/2008 | Ehwald et al. |
| 7,479,131 B2 | 1/2009 | Mathias et al. |
| 7,614,857 B2 | 11/2009 | Fuechslin et al. |
| 7,618,407 B2 | 11/2009 | Demay et al. |
| 7,648,491 B2 | 1/2010 | Rogers |
| 7,666,166 B1 | 2/2010 | Emmert et al. |
| 7,744,573 B2 | 6/2010 | Gordon et al. |
| 7,780,794 B2 | 8/2010 | Rogers et al. |
| 7,896,817 B2 | 3/2011 | Garrison |
| 7,985,302 B2 | 7/2011 | Rogers et al. |
| 8,197,420 B2 | 6/2012 | Patton |
| 8,206,318 B2 | 6/2012 | Uchiyama et al. |
| 8,206,514 B2 | 6/2012 | Rogers et al. |
| 8,231,546 B2 | 7/2012 | Patton |
| 8,282,605 B2 | 10/2012 | Tan et al. |
| 8,287,499 B2 | 10/2012 | Miyasaka |
| 8,337,418 B2 | 12/2012 | Patton |
| 8,349,254 B2 | 1/2013 | Hoshino et al. |
| 8,356,644 B2 | 1/2013 | Chong et al. |
| 8,377,040 B2 | 2/2013 | Burkholz et al. |
| 8,382,712 B2 | 2/2013 | Kim |
| 8,523,826 B2 | 9/2013 | Layton, Jr. |
| 8,535,241 B2 | 9/2013 | Bullington et al. |
| 8,540,663 B2 | 9/2013 | Davey et al. |
| 8,568,371 B2 | 10/2013 | Siopes et al. |
| 8,574,203 B2 | 11/2013 | Stout et al. |
| 8,603,009 B2 | 12/2013 | Tan et al. |
| 8,647,286 B2 | 2/2014 | Patton |
| 8,827,958 B2 | 9/2014 | Bierman et al. |
| 8,832,894 B2 | 9/2014 | Rogers et al. |
| 8,864,684 B2 | 10/2014 | Bullington et al. |
| 8,876,734 B2 | 11/2014 | Patton |
| 8,992,505 B2 | 3/2015 | Thorne, Jr. et al. |
| 8,999,073 B2 | 4/2015 | Rogers et al. |
| 9,022,950 B2 | 5/2015 | Bullington et al. |
| 9,022,951 B2 | 5/2015 | Bullington et al. |
| 9,060,724 B2 | 6/2015 | Bullington et al. |
| 9,060,725 B2 | 6/2015 | Bullington et al. |
| 9,138,572 B2 | 9/2015 | Zeytoonian et al. |
| 9,149,576 B2 | 10/2015 | Bullington et al. |
| 9,155,495 B2 | 10/2015 | Bullington et al. |
| 9,204,864 B2 | 12/2015 | Bullington et al. |
| 9,259,284 B2 | 2/2016 | Rogers et al. |
| 9,320,459 B2 | 4/2016 | Chin et al. |
| 9,820,682 B2 | 11/2017 | Rogers et al. |
| 9,855,001 B2 | 1/2018 | Patton |
| 9,855,002 B2 | 1/2018 | Patton |
| 9,855,386 B2 | 1/2018 | Close et al. |
| 9,861,306 B2 | 1/2018 | Patton |
| 9,872,645 B2 | 1/2018 | Patton |
| 9,877,675 B2 | 1/2018 | Baid |
| 9,931,466 B2 | 4/2018 | Bullington et al. |
| 9,950,084 B2 | 4/2018 | Bullington et al. |
| 9,962,489 B2 | 5/2018 | Hopkins |
| 9,999,383 B2 | 6/2018 | Bullington et al. |
| 10,010,282 B2 | 7/2018 | Rogers et al. |
| 10,022,079 B2 | 7/2018 | Hopkins |
| 10,022,530 B2 | 7/2018 | Tekeste |
| 10,028,687 B2 | 7/2018 | Patton |
| 10,028,688 B2 | 7/2018 | Patton |
| 10,028,689 B2 | 7/2018 | Patton |
| 10,039,483 B2 | 8/2018 | Bullington et al. |
| 10,045,724 B2 | 8/2018 | Patton |
| 10,052,053 B2 | 8/2018 | Patton |
| 10,123,783 B2 | 11/2018 | Bullington et al. |
| 10,143,412 B2 | 12/2018 | Rogers et al. |
| 10,143,413 B2 | 12/2018 | Garrett et al. |
| 10,206,613 B2 | 2/2019 | Bullington et al. |

(56) References Cited

U.S. PATENT DOCUMENTS

| | | |
|---|---|---|
| 10,220,139 B2 | 3/2019 | Bullington et al. |
| 10,238,326 B2 | 3/2019 | Gil et al. |
| 10,251,590 B2 | 4/2019 | Bullington et al. |
| 10,265,007 B2 | 4/2019 | Bullington et al. |
| 10,292,633 B2 | 5/2019 | Bullington et al. |
| 10,299,713 B2 | 5/2019 | Patton |
| 10,369,285 B2 | 8/2019 | Hopkins |
| 10,433,779 B2 | 10/2019 | Bullington et al. |
| 10,463,792 B2 | 11/2019 | Hopkins |
| 10,596,315 B2 | 3/2020 | Bullington et al. |
| 10,624,977 B2 | 4/2020 | Bullington et al. |
| 10,736,554 B2 | 8/2020 | Bullington et al. |
| 10,744,315 B2 | 8/2020 | Sanders |
| 10,772,548 B2 | 9/2020 | Bullington et al. |
| 10,827,964 B2 | 11/2020 | Rogers et al. |
| 10,881,343 B2 | 1/2021 | Bullington et al. |
| 10,912,506 B2 | 2/2021 | Bullington et al. |
| 11,076,787 B2 | 8/2021 | Bullington et al. |
| 11,116,904 B2 | 9/2021 | Hopkins |
| 11,167,085 B2 | 11/2021 | Hopkins |
| 11,234,626 B2 | 2/2022 | Bullington et al. |
| 11,253,649 B2 | 2/2022 | Hopkins |
| 11,259,727 B2 | 3/2022 | Bullington et al. |
| 11,311,218 B2 | 4/2022 | Bullington et al. |
| 11,317,838 B2 | 5/2022 | Bullington et al. |
| 11,395,611 B2 | 7/2022 | Bullington et al. |
| 11,395,612 B2 | 7/2022 | Bullington et al. |
| 11,529,081 B2 | 12/2022 | Bullington et al. |
| 11,589,786 B2 | 2/2023 | Bullington et al. |
| 11,589,843 B2 | 2/2023 | Bullington et al. |
| 11,607,159 B2 | 3/2023 | Bullington et al. |
| 11,653,863 B2 | 5/2023 | Bullington et al. |
| 11,737,693 B2 | 8/2023 | Bullington et al. |
| 11,819,329 B2 | 11/2023 | Bullington et al. |
| 11,857,321 B2 | 1/2024 | Bullington et al. |
| 2001/0039058 A1 | 11/2001 | Iheme et al. |
| 2002/0002349 A1 | 1/2002 | Flaherty et al. |
| 2002/0004647 A1 | 1/2002 | Leong |
| 2002/0107469 A1 | 8/2002 | Bolan et al. |
| 2002/0183651 A1 | 12/2002 | Hyun |
| 2002/0193751 A1 | 12/2002 | Theeuwes et al. |
| 2003/0013991 A1 | 1/2003 | Stone |
| 2003/0040708 A1 | 2/2003 | Rogers et al. |
| 2003/0055381 A1 | 3/2003 | Wilkinson |
| 2003/0069543 A1 | 4/2003 | Carpenter et al. |
| 2003/0105414 A1 | 6/2003 | Leong |
| 2003/0208151 A1 | 11/2003 | Kraus et al. |
| 2004/0009542 A1 | 1/2004 | Dumont et al. |
| 2004/0010228 A1 | 1/2004 | Swenson et al. |
| 2004/0054283 A1 | 3/2004 | Corey et al. |
| 2004/0054333 A1 | 3/2004 | Theeuwes et al. |
| 2004/0127816 A1 | 7/2004 | Galvao |
| 2004/0147855 A1 | 7/2004 | Marsden |
| 2005/0004524 A1 | 1/2005 | Newby et al. |
| 2005/0148993 A1 | 7/2005 | Mathias et al. |
| 2005/0154368 A1 | 7/2005 | Lim et al. |
| 2005/0161112 A1 | 7/2005 | Ehwald et al. |
| 2005/0199077 A1 | 9/2005 | Prybella et al. |
| 2005/0240161 A1 | 10/2005 | Crawford |
| 2005/0245885 A1 | 11/2005 | Brown |
| 2005/0273019 A1 | 12/2005 | Conway et al. |
| 2005/0277848 A1 | 12/2005 | Graf |
| 2005/0281713 A1 | 12/2005 | Hampsch et al. |
| 2006/0096877 A1 | 5/2006 | Khajavi et al. |
| 2006/0111667 A1 | 5/2006 | Matsuura et al. |
| 2006/0155212 A1 | 7/2006 | Madonia |
| 2006/0251622 A1 | 11/2006 | Suzuki et al. |
| 2006/0287639 A1 | 12/2006 | Sharp |
| 2007/0083162 A1 | 4/2007 | O'Reagan et al. |
| 2007/0088279 A1 | 4/2007 | Shue et al. |
| 2007/0100250 A1 | 5/2007 | Kline |
| 2007/0119508 A1 | 5/2007 | West et al. |
| 2007/0287948 A1 | 12/2007 | Sakiewicz |
| 2008/0086085 A1 | 4/2008 | Brown |
| 2008/0108954 A1 | 5/2008 | Mathias et al. |
| 2008/0114304 A1 | 5/2008 | Nalesso et al. |
| 2008/0167577 A1 | 7/2008 | Weilbacher et al. |
| 2008/0185056 A1 | 8/2008 | Diodati et al. |
| 2008/0200837 A1 | 8/2008 | Frazier et al. |
| 2008/0254471 A1 | 10/2008 | Bordano |
| 2008/0255523 A1 | 10/2008 | Grinberg |
| 2008/0312576 A1 | 12/2008 | Mckinnon et al. |
| 2008/0319346 A1 | 12/2008 | Crawford et al. |
| 2009/0050213 A1 | 2/2009 | Biddell et al. |
| 2009/0076441 A1 | 3/2009 | Sebban |
| 2009/0192447 A1 | 7/2009 | Andersen et al. |
| 2009/0227896 A1 | 9/2009 | Alvin Tan et al. |
| 2009/0301317 A1 | 12/2009 | Andrews |
| 2009/0306601 A1 | 12/2009 | Shaw et al. |
| 2010/0010372 A1 | 1/2010 | Brown et al. |
| 2010/0042048 A1 | 2/2010 | Christensen |
| 2010/0057004 A1 | 3/2010 | Christensen et al. |
| 2010/0094171 A1 | 4/2010 | Conway et al. |
| 2010/0152681 A1 | 6/2010 | Mathias |
| 2010/0234768 A1 | 9/2010 | Uchiyama et al. |
| 2010/0268118 A1 | 10/2010 | Schweiger |
| 2010/0286513 A1 | 11/2010 | Pollard, Jr. et al. |
| 2010/0306938 A1 | 12/2010 | Rogers et al. |
| 2011/0232020 A1 | 9/2011 | Rogers et al. |
| 2011/0306899 A1 | 12/2011 | Brown et al. |
| 2012/0004619 A1 | 1/2012 | Stephens et al. |
| 2012/0016266 A1 | 1/2012 | Burkholz |
| 2012/0035540 A1 | 2/2012 | Ferren et al. |
| 2012/0216359 A1 | 8/2012 | Rogers et al. |
| 2012/0216360 A1 | 8/2012 | Rogers et al. |
| 2012/0226239 A1 | 9/2012 | Green |
| 2012/0265099 A1 | 10/2012 | Goodnow, II et al. |
| 2012/0265128 A1 | 10/2012 | Kolln |
| 2013/0085514 A1 | 4/2013 | Lee et al. |
| 2013/0158506 A1 | 6/2013 | Harris et al. |
| 2014/0008366 A1 | 1/2014 | Genosar |
| 2014/0066880 A1 | 3/2014 | Prince et al. |
| 2014/0128775 A1 | 5/2014 | Andreae et al. |
| 2014/0150832 A1 | 6/2014 | Rogers et al. |
| 2014/0155782 A1* | 6/2014 | Bullington ......... A61B 10/0045 600/575 |
| 2014/0221873 A1 | 8/2014 | Hayakawa et al. |
| 2014/0261558 A1 | 9/2014 | Rogers et al. |
| 2014/0261581 A1 | 9/2014 | Rogers |
| 2015/0000061 A1 | 1/2015 | Rogers et al. |
| 2015/0011847 A1 | 1/2015 | Hayden |
| 2015/0018715 A1 | 1/2015 | Walterspiel |
| 2015/0025454 A1 | 1/2015 | Wetzel et al. |
| 2015/0025455 A1 | 1/2015 | Shetty et al. |
| 2015/0025456 A1 | 1/2015 | Shetty et al. |
| 2015/0246352 A1 | 9/2015 | Bullington et al. |
| 2015/0314105 A1 | 11/2015 | Gasparyan et al. |
| 2015/0359473 A1 | 12/2015 | Garrett et al. |
| 2016/0008579 A1 | 1/2016 | Burkholz et al. |
| 2016/0081606 A1 | 3/2016 | Russ et al. |
| 2016/0113560 A1 | 4/2016 | Bullington et al. |
| 2016/0174888 A1 | 6/2016 | Berthier et al. |
| 2016/0213294 A1 | 7/2016 | Patton |
| 2016/0367177 A1 | 12/2016 | Edelhauser et al. |
| 2017/0020427 A1 | 1/2017 | Rogers et al. |
| 2017/0020428 A1 | 1/2017 | Rogers et al. |
| 2017/0059552 A1 | 3/2017 | Campton et al. |
| 2017/0071519 A1 | 3/2017 | Gelfand et al. |
| 2017/0276679 A1 | 9/2017 | Chapman et al. |
| 2017/0361019 A1 | 12/2017 | Hopkins |
| 2018/0093077 A1 | 4/2018 | Harding et al. |
| 2018/0160958 A1 | 6/2018 | Baid |
| 2018/0177445 A1 | 6/2018 | Rogers et al. |
| 2018/0289894 A1 | 10/2018 | Hopkins |
| 2018/0321270 A1 | 11/2018 | Iwashita et al. |
| 2018/0353117 A1 | 12/2018 | Bullington et al. |
| 2018/0361003 A1 | 12/2018 | Dombrowski et al. |
| 2019/0000367 A1 | 1/2019 | Lundquist et al. |
| 2019/0049442 A1 | 2/2019 | Guirguis |
| 2019/0125315 A1 | 5/2019 | Bullington et al. |
| 2019/0150818 A1 | 5/2019 | Bullington et al. |
| 2019/0159711 A1 | 5/2019 | Rogers et al. |
| 2019/0209066 A1 | 7/2019 | Bullington et al. |
| 2019/0365303 A1 | 12/2019 | Bullington et al. |

(56) References Cited

U.S. PATENT DOCUMENTS

| | | | |
|---|---|---|---|
| 2020/0060595 | A1 | 2/2020 | Bullington et al. |
| 2020/0060596 | A1 | 2/2020 | Patton |
| 2020/0197925 | A1 | 6/2020 | Ivosevic et al. |
| 2020/0253524 | A1 | 8/2020 | Bullington et al. |
| 2020/0289039 | A1 | 9/2020 | Bullington et al. |
| 2021/0008280 | A1 | 1/2021 | Bullington et al. |
| 2021/0169387 | A1 | 6/2021 | Bullington et al. |
| 2021/0186392 | A1 | 6/2021 | Bullington et al. |
| 2021/0275068 | A1 | 9/2021 | Miazga et al. |
| 2021/0361206 | A1 | 11/2021 | Bullington et al. |
| 2022/0023539 | A1 | 1/2022 | Hopkins |
| 2022/0151525 | A1 | 5/2022 | Bullington et al. |
| 2022/0183600 | A1 | 6/2022 | Bullington et al. |
| 2022/0218248 | A1 | 7/2022 | Bullington et al. |
| 2022/0218249 | A1 | 7/2022 | Bullington et al. |
| 2022/0218250 | A1 | 7/2022 | Bullington et al. |
| 2022/0304600 | A1 | 9/2022 | Hammer |
| 2022/0304664 | A1 | 9/2022 | Hammer |
| 2022/0361786 | A1 | 11/2022 | Bullington et al. |
| 2022/0369970 | A1 | 11/2022 | Bullington et al. |
| 2022/0369971 | A1 | 11/2022 | Bullington et al. |
| 2022/0369972 | A1 | 11/2022 | Bullington et al. |
| 2023/0151526 | A1 | 5/2023 | Moon et al. |
| 2023/0151527 | A1 | 5/2023 | Bocchino et al. |
| 2023/0172502 | A1 | 6/2023 | Bullington et al. |
| 2023/0190157 | A1 | 6/2023 | Bullington et al. |
| 2023/0240571 | A1 | 8/2023 | Bullington et al. |
| 2023/0248281 | A1 | 8/2023 | Bullington et al. |
| 2023/0320702 | A1 | 10/2023 | Bullington et al. |
| 2023/0363674 | A1 | 11/2023 | Bullington et al. |
| 2024/0008780 | A1 | 1/2024 | Bullington et al. |
| 2024/0041369 | A1 | 2/2024 | Bullington et al. |
| 2024/0057908 | A1 | 2/2024 | Bullington et al. |
| 2024/0065590 | A1 | 2/2024 | Bullington et al. |

FOREIGN PATENT DOCUMENTS

| | | | |
|---|---|---|---|
| CN | 86103696 | A | 1/1987 |
| CN | 2115767 | U | 9/1992 |
| CN | 1713928 | A | 12/2005 |
| CN | 1784186 | A | 6/2006 |
| CN | 1901955 | A | 1/2007 |
| CN | 2907683 | Y | 6/2007 |
| CN | 1325126 | C | 7/2007 |
| CN | 101060871 | A | 10/2007 |
| CN | 101309641 | A | 11/2008 |
| CN | 101352357 | A | 1/2009 |
| CN | 101437450 | A | 5/2009 |
| CN | 101631498 | A | 1/2010 |
| CN | 101676001 | A | 3/2010 |
| CN | 101801445 | A | 8/2010 |
| CN | 102548524 | A | 7/2012 |
| CN | 102971040 | A | 3/2013 |
| CN | 103027727 | A | 4/2013 |
| CN | 101626803 | B | 8/2013 |
| CN | 103477201 | A | 12/2013 |
| CN | 104902817 | A | 9/2015 |
| CN | 104981203 | A | 10/2015 |
| CN | 105090005 | A | 11/2015 |
| CN | 105612346 | A | 5/2016 |
| DE | 7203008 | U | 5/1972 |
| DE | 2203858 | A1 | 5/1973 |
| DE | 2541494 | A1 | 3/1977 |
| DE | 2203858 | B2 | 10/1977 |
| DE | 2946660 | A1 | 5/1981 |
| DE | 3403957 | A1 | 8/1985 |
| DE | 29913417 | U1 | 12/2000 |
| DE | 10038026 | A1 | 2/2001 |
| DE | 10134913 | A1 | 2/2003 |
| DE | 10134913 | C2 | 6/2003 |
| DE | 10243129 | A1 | 4/2004 |
| DE | 102009057792 | B4 | 8/2016 |
| EP | 0207304 | A1 | 1/1987 |
| EP | 0264191 | A2 | 4/1988 |
| EP | 0448795 | A2 | 10/1991 |
| EP | 0329786 | B1 | 1/1993 |
| EP | 0565103 | A1 | 10/1993 |
| EP | 1144026 | B1 | 7/2004 |
| EP | 1219283 | B1 | 6/2005 |
| EP | 1980204 | A1 | 10/2008 |
| EP | 1381438 | B1 | 5/2012 |
| EP | 2692324 | A1 | 2/2014 |
| EP | 1487369 | B1 | 5/2017 |
| EP | 2986218 | B1 | 12/2017 |
| EP | 2178585 | B1 | 4/2021 |
| FR | 2110516 | A5 | 6/1972 |
| FR | 2691364 | B1 | 8/1999 |
| FR | 2833175 | B1 | 5/2004 |
| FR | 2851167 | B1 | 10/2005 |
| GB | 1506449 | A | 4/1978 |
| GB | 1562686 | A | 3/1980 |
| IE | 904353 | A1 | 10/1991 |
| IL | 128709 | A | 9/2004 |
| JP | S4846180 | A | 7/1973 |
| JP | S5397289 | A | 8/1978 |
| JP | S5789869 | A | 6/1982 |
| JP | S6458241 | A | 3/1989 |
| JP | H0363570 | A | 3/1991 |
| JP | H06500403 | A | 1/1994 |
| JP | H0716219 | A | 1/1995 |
| JP | H1156821 | A | 3/1999 |
| JP | H1176397 | A | 3/1999 |
| JP | 3231086 | B2 | 11/2001 |
| JP | 2002116201 | A | 4/2002 |
| JP | 2002528159 | A | 9/2002 |
| JP | 2005237617 | A | 9/2005 |
| JP | 2008149076 | A | 7/2008 |
| JP | 4382322 | B2 | 12/2009 |
| JP | 2010514501 | A | 5/2010 |
| JP | 2010189415 | A | 9/2010 |
| JP | 4573538 | B2 | 11/2010 |
| JP | 4861649 | B2 | 1/2012 |
| JP | 4869910 | B2 | 2/2012 |
| JP | 2015014552 | A | 1/2015 |
| JP | 2016523591 | A | 8/2016 |
| JP | 5997760 | B2 | 9/2016 |
| JP | 2016527939 | A | 9/2016 |
| JP | 6194415 | B2 | 9/2017 |
| JP | 2018525191 | A | 9/2018 |
| KR | 20120030087 | A | 3/2012 |
| KR | 101134279 | B1 | 4/2012 |
| TW | 200528066 | A | 9/2005 |
| WO | WO-8605568 | A1 | 9/1986 |
| WO | WO-9004351 | A1 | 5/1990 |
| WO | WO-9118632 | A1 | 12/1991 |
| WO | WO-9216144 | A1 | 10/1992 |
| WO | WO-9407415 | A1 | 4/1994 |
| WO | WO-9415665 | A1 | 7/1994 |
| WO | WO-9511712 | A1 | 5/1995 |
| WO | WO-9516395 | A1 | 6/1995 |
| WO | WO-9524176 | A1 | 9/1995 |
| WO | WO-9621853 | A1 | 7/1996 |
| WO | WO-9718845 | A1 | 5/1997 |
| WO | WO-9846136 | A1 | 10/1998 |
| WO | WO-9913925 | A1 | 3/1999 |
| WO | WO-9948425 | A1 | 9/1999 |
| WO | WO-9955232 | A1 | 11/1999 |
| WO | WO-0024313 | A1 | 5/2000 |
| WO | WO-0040291 | A1 | 7/2000 |
| WO | WO-0041624 | A1 | 7/2000 |
| WO | WO-0108546 | A2 | 2/2001 |
| WO | WO-0191829 | A2 | 12/2001 |
| WO | WO-0245813 | A1 | 6/2002 |
| WO | WO-02051520 | A1 | 7/2002 |
| WO | WO-03008012 | A2 | 1/2003 |
| WO | WO-03041767 | A1 | 5/2003 |
| WO | WO-03047660 | A1 | 6/2003 |
| WO | WO-03078964 | A2 | 9/2003 |
| WO | WO-03085395 | A1 | 10/2003 |
| WO | WO-2005068011 | A1 | 7/2005 |
| WO | WO-2006031500 | A2 | 3/2006 |
| WO | WO-2006117138 | A1 | 11/2006 |
| WO | WO-2007033319 | A1 | 3/2007 |
| WO | WO-2008101025 | A1 | 8/2008 |

(56) References Cited

FOREIGN PATENT DOCUMENTS

| WO | WO-2009094345 A1 | 7/2009 |
|---|---|---|
| WO | WO-2011030282 A1 | 3/2011 |
| WO | WO-2011069145 A2 | 6/2011 |
| WO | WO-2011123685 A2 | 10/2011 |
| WO | WO-2012012127 A2 | 1/2012 |
| WO | WO-2012114105 A1 | 8/2012 |
| WO | WO-2014058945 A1 | 4/2014 |
| WO | WO-2015134431 A1 | 9/2015 |
| WO | WO-2016054252 A1 | 4/2016 |
| WO | WO-2017019552 A1 | 2/2017 |
| WO | WO-2017041087 A1 | 3/2017 |
| WO | WO-2017133953 A1 | 8/2017 |
| WO | WO-2018094310 A1 | 5/2018 |
| WO | WO-2018125929 A1 | 7/2018 |
| WO | WO-2019113505 A1 | 6/2019 |
| WO | WO-2020163744 A1 | 8/2020 |
| WO | WO-2022203747 A1 | 9/2022 |

OTHER PUBLICATIONS

Barnard, D. R. & Arthur, M. M., "Fibronectin (cold insoluble globulin) in the neonate," Clinical and Laboratory Observations, 102(3): 453-455 (1983).
Baxter, "IV Tubing and Access Devices" authored by and published by Baxter, dated Nov. 6, 2006, 105 pages.
BD Saf-T-Intima Closed IV Catheter System, Becton, Dickinson and Company, 2015 Brochure. Retrieved from the Internet (Sep. 11, 2019) https://www.bd.com/en-us/offerings/capabilities/infusion-therapy/iv-catheters/bd-saf-tintima-closed-iv-catheter-system, 2 pages.
BD Vacutainer Passive Shielding Blood Collection Needle Brochure; Becton Dickinson and Company (2005), 2 pages.
Brecher, M. E. et al., "Bacterial Contamination of Blood Components," Clinical Microbiology Reviews, 18(1):195-204 (2005).
Calam, R. R., "Recommended 'Order of Draw' for Collecting Blood Specimens Into Additive-Containing Tubes," Letter to the Editor, Clinical Chemistry, 28(6):1399 (1982), 1 page.
Cartridge and Test Information, Abbott, Art: 714258-010 Rev. Date: Aug. 15, 2016, 6 pages.
Challiner, A. et al., Queen Alexandra Hospital, Portsmouth P06 3LY, "Venous/arterial blood management protection system," Correspondence, 1992, p. 169.
Claim Construction Order in *Retractable Technologies, Inc.*, and *Thomas Shaw v. Becton Dickinson & Co.*, Civil Action No. 2:07-CV-250 (OF) (Jan. 20, 2009). 32 pages.
De Korte, D. et al., "Diversion of first blood volume results in a reduction of bacterial contamination for whole-blood collections," Vox Sanguinis, 83:13-16 (2002).
De Korte, D. et al., "Effects of skin disinfection method, deviation bag, and bacterial screening on clinical safety of platelet transfusions in the Netherlands," Transfusion, 46: 476-485 (2006).
Declaration of Dr. Erik K. Antonsson, PH.D.. P.E., NAE (Mar. 21, 2023). 137 pages.
Edwards Lifesciences, "Conservation. Safety. Simplicity. Edwards VAMP and VAMP Jr. Systems," 2002 Brochure. Retrieved from the Internet (Sep. 11, 2019) https://www.medline.com/media/catalog/Docs/MKT/VAMPSYSTEMBROCHURE.PDF, 4 pages.
Ernst, D. J. et al., "NCCLS simplifies the order of draw: a brief history," MLO, 26-27 (2004).
Exhibit 01—Defendant's Invalidity Contentions, Invalidity Claim Chart—U.S. Pat. No. 9,855,001 vs Barnard NPL, Aug. 30, 2019, 8 pages.
Exhibit 02—Defendant's Invalidity Contentions, Invalidity Claim Chart—U.S. Pat. No. 9,855,001 vs BD Needle NPL, Aug. 30, 2019, 7 pages.
Exhibit 03—Defendant's Invalidity Contentions, Invalidity Claim Chart—U.S. Pat. No. 9,855,001 vs U.S. Pat. No. 6,626,884, Aug. 30, 2019, 11 pages.
Exhibit 04—Defendant's Invalidity Contentions, Invalidity Claim Chart—U.S. Pat. No. 9,855,001 vs U.S. Pat. Pub. No. 2005/161112, Aug. 30, 2019,22 pages.
Exhibit 05—Defendant's Invalidity Contentions, Invalidity Claim Chart—U.S. Pat. No. 9,855,001 vs U.S. Pat. No. 4,673,386, Aug. 30, 2019, 21 pages.
Exhibit 06—Defendant's Invalidity Contentions, Invalidity Claim Chart—U.S. Pat. No. 9,855,001 vs U.S. Pat. No. 4,904,240, Aug. 30, 2019, 15 pages.
Exhibit 07—Defendant's Invalidity Contentions, Invalidity Claim Chart—U.S. Pat. No. 9,855,001 vs Leukotrap NPL, Aug. 30, 2019, 38 pages.
Exhibit 09—Defendant's Invalidity Contentions, Invalidity Claim Chart—U.S. Pat. No. 9,855,001 vs U.S. Pat. No. 4,106,497, Aug. 30, 2019, 22 pages.
Exhibit 10—Defendant's Invalidity Contentions, Invalidity Claim Chart—U.S. Pat. No. 9,855,001 vs Stopcock-Syringe NPL, Aug. 30, 2019, 85 pages.
Exhibit 11—Defendant's Invalidity Contentions, Invalidity Claim Chart—U.S. Pat. No. 9,855,001 vs Ziegler NPL, Aug. 30, 2019, 8 pages.
Exhibit 12—Defendant's Invalidity Contentions, Invalidity Claim Chart—U.S. Pat. No. 10,028,689 vs Barnard NPL, Aug. 30, 2019, 12 pages.
Exhibit 13—Defendant's Invalidity Contentions, Invalidity Claim Chart—U.S. Pat. No. 10,028,689 vs U.S. Pat. No. 6,626,884, Aug. 30, 2019, 29 pages.
Exhibit 14—Defendant's Invalidity Contentions, Invalidity Claim Chart—U.S. Pat. No. 10,028,689 vs U.S. Pat. Pub. No. 2005/161112, Aug. 30, 2019,48 pages.
Exhibit 15—Defendant's Invalidity Contentions, Invalidity Claim Chart—U.S. Pat. No. 10,028,689 vs U.S. Pat. No. 4,673,386, Aug. 30, 2019, 44 pages.
Exhibit 16—Defendant's Invalidity Contentions, Invalidity Claim Chart—U.S. Pat. No. 10,028,689 vs U.S. Pat. No. 4,904,240, Aug. 30, 2019, 31 pages.
Exhibit 17—Defendant's Invalidity Contentions, Invalidity Claim Chart—U.S. Pat. No. 10,028,689 vs Leukotrap NPL, Aug. 30, 2019, 113 pages.
Exhibit 19—Defendant's Invalidity Contentions, Invalidity Claim Chart—U.S. Pat. No. 10,028,689 vs U.S. Pat. No. 4, 106,497, Aug. 30, 2019, 38 pages.
Exhibit 20—Defendant's Invalidity Contentions, Invalidity Claim Chart—U.S. Pat. No. 10,028,689 vs Stopcock-Syringe NPL, Aug. 30, 2019, 268 pages.
Exhibit 21—Defendant's Invalidity Contentions, Invalidity Claim Chart—U.S. Pat. No. 10,220,139 vs U.S. Pat. No. 6,626,884, Aug. 30, 2019, 35 pages.
Exhibit 22—Defendant's Invalidity Contentions, Invalidity Claim Chart—U.S. Pat. No. 10,220,139 vs U.S. Pat. Pub. No. 2005/161112, Aug. 30, 2019,46 pages.
Exhibit 23—Defendant's Invalidity Contentions, Invalidity Claim Chart—U.S. Pat. No. 10,220,139 vs U.S. Pat. No. 4,207,870, Aug. 30, 2019, 20 pages.
Exhibit 24—Defendant's Invalidity Contentions, Invalidity Claim Chart—U.S. Pat. No. 10,220,139 vs U.S. Pat. No. 6,506,182, Aug. 30, 2019, 15 pages.
Exhibit 25—Defendant's Invalidity Contentions, Invalidity Claim Chart—U.S. Pat. No. 10,220,139 vs U.S. Pat. No. 4,673,386, Aug. 30, 2019, 53 pages.
Exhibit 26—Defendant's Invalidity Contentions, Invalidity Claim Chart—U.S. Pat. No. 10,220,139 vs U.S. Pat. No. 4,904,240, Aug. 30, 2019, 39 pages.
Exhibit 27—Defendant's Invalidity Contentions, Invalidity Claim Chart—U.S. Pat. No. 10,220,139 vs Leukotrap NPL, Aug. 30, 2019, 115 pages.
Exhibit 29—Defendant's Invalidity Contentions, Invalidity Claim Chart—U.S. Pat. No. 10,220,139 vs U.S. Pat. No. 4, 106,497, Aug. 30, 2019, 45 pages.
Exhibit 30—Defendant's Invalidity Contentions, Invalidity Claim Chart—U.S. Pat. No. 10,220,139 vs Stopcock-Syringe NPL, Aug. 30, 2019, 246 pages.
Exhibit 31—Defendant's Invalidity Contentions, Invalidity Claim Chart—U.S. Pat. No. 10,220,139 vs U.S. Pat. No. 4,349,035, Aug. 30, 2019, 26 pages.

(56) References Cited

OTHER PUBLICATIONS

Exhibit 32—Defendant's Invalidity Contentions, Invalidity Claim Chart—U.S. Pat. No. 10,220,139 vs U.S. Pat. Pub. No. 2008/0145933A1, Aug. 30, 2019, 39 pages.
Exhibit 33—Defendant's Invalidity Contentions, Invalidity Claim Chart—U.S. Pat. No. 10,039,483 vs Barnard NPL, Aug. 30, 2019, 14 pages.
Exhibit 34—Defendant's Invalidity Contentions, Invalidity Claim Chart—U.S. Pat. No. 10,039,483 vs U.S. Pat. No. 6,626,884, Aug. 30, 2019, 22 pages.
Exhibit 35—Defendant's Invalidity Contentions, Invalidity Claim Chart—U.S. Pat. No. 10,039,483 vs U.S. Pat. Pub. No. 2005/161112, Aug. 30, 2019, 45 pages.
Exhibit 36—Defendant's Invalidity Contentions, Invalidity Claim Chart—U.S. Pat. No. 10,039,483 vs U.S. Pat. No. 4,673,386, Aug. 30, 2019, 47 pages.
Exhibit 37—Defendant's Invalidity Contentions, Invalidity Claim Chart—U.S. Pat. No. 10,039,483 vs U.S. Pat. No. 4,904,240, Aug. 30, 2019, 30 pages.
Exhibit 38—Defendant's Invalidity Contentions, Invalidity Claim Chart—U.S. Pat. No. 10,039,483 vs Leukotrap NPL, Aug. 30, 2019, 115 pages.
Exhibit 40—Defendant's Invalidity Contentions, Invalidity Claim Chart—U.S. Pat. No. 10,039,483 vs U.S. Pat. No. 4,106,497, Aug. 30, 2019, 45 pages.
Exhibit 41—Defendant's Invalidity Contentions, Invalidity Claim Chart—U.S. Pat. No. 10,039,483 vs Stopcock-Syringe NPL, Aug. 30, 2019, 214 pages.
Exhibit 42—Defendant's Invalidity Contentions, Invalidity Claim Chart—U.S. Pat. No. 10,039,483 vs U.S. Pat. Pub. No. 2008/0145933A1, Aug. 30, 2019, 38 pages.
Extended European Search Report for European Application No. 20167572.5, dated Sep. 30, 2020, 10 pages.
File History of U.S. Appl. No. 15/832,091, filed Dec. 5, 2017, 360 pages.
Final Rejection Office Action for U.S. Appl. No. 16/146,251 mailed on Jul. 13, 2022, 7 pages.
First Amended Complaint in *Magnolia Medical Technologies, Inc. v. Kurin, Inc.*, C.A. No. 19-cv-00097-CFC, Document 5 (Filed Mar. 7, 2019). 40 pages.
Gottlieb, T., "Hazards of Bacterial Contamination of Blood Products," Anaesth Intens Care, 21: 20-23 (1993).
Hall, K. K. et al., "Updated Review of Blood Culture Contamination," Clinical Microbiology Reviews, 19(4):788-802 (2006).
Hillyer, C. D. et al., "Bacterial Contamination of Blood Components Risks, Strategies, and Regulation," Hematology, 575-589 (2003).
International Search Report and Written Opinion for International Application No. PCT/US2015/018397, dated Aug. 11, 2015, 16 pages.
International Search Report and Written Opinion for International Application No. PCT/US2016/050380, dated Dec. 1, 2016, 6 pages.
International Search Report and Written Opinion for International Application No. PCT/US2020/017261, mailed May 14, 2020.
Kim, J. Y. et al., "The Sum of the Parts is Greater Than the Whole: Reducing Blood Culture Contamination," Annals of Internal Medicine, 154:202-203 (2011).
Kurin, Inc.'s Opening Post-Trial Brief Regarding indefiniteness in *Magnolia Medical Technologies, Inc. v. Kurin, Inc.*, C.A. No. 19-097 (CFC)(CJB), Document 463 (Filed Sep. 30, 2022), 25 pages.
Levin, P. D. et al., "Use of the Nonwire Central Line Hub to Reduce Blood Culture Contamination," Chest, 143(3):640-645 (2013).
Litigation Search Report CRU 3999 for Reexamination Application No. 90/019,177 dated Mar. 23, 2023, 95 pages.
Liumbruno, G. M. et al., "Reduction of the risk of bacterial contamination of blood components through diversion of the first part of the donation of blood and blood components," Blood Transfus, 7: 86-93 (2009).

Li, Y. et al., "Direct labeling and visualization of blood vessels with lipophilic carbocyanine dye Oil," Nature Protocols, 3(11): 1703-1708 (2008).
Magnolia's Answer Brief in Opposition to Kurin, Inc.'s Opening Post-Trial Brief Regarding Indefiniteness in *Magnolia Medical Technologies, Inc. v. Kurin, Inc.*, C.A. No. 19-097 (CFC)(CJB), Document 463 (Filed Sep. 30, 2022). 25 pages.
Mayer, G. A, "A Method for the Reliable Determination of Clotting Time in Whole Blood," Can Med Assoc J., 72(12): 927-929 (1955).
Mcdonald, C. P., "Interventions Implemented to Reduce the Risk of Transmission of Bacteria by Transfusion in the English National Blood Service," Transfus Med Hemother, 38:255-258 (2011).
Meissner, G. F. et al., "A Method Based on the Use of Whole Venous Blood in Capillary Tubes," American Journal of Clinical Pathology, 33(2): 29-31 (1963).
Murphy, M., "Better Blood Transfusion," Journal of the Intensive Core Society, 4(3): 78-80 (2003).
Napolitano, M. et al., "Quality control of bacterial contamination of blood components: the feasibility of diversion system testing," Blood Transfus, 2: 231-232 (2004).
Non-Final Office Action for U.S. Appl. No. 16/785,170 mailed on Sep. 14, 2022, 10 pages.
Norberg, A. et al., "Contamination Rates of Blood Cultures Obtained by Dedicated Phlebotomy vs Intravenous Catheter," JAMA, 289(6): 726-729 (2003).
Notice of Reasons for Rejection for Japanese Application No. 2020-075727, dated Jul. 21, 2021, with English translation, 37 pages.
Office Action for Canadian Application No. 2,875,118, dated Mar. 21, 2019, 5 pages.
Office Action for U.S. Appl. No. 14/636,485, dated Feb. 9, 2017, 2017, 8 pages.
Office Action for U.S. Appl. No. 14/636,485, dated Jul. 7, 2017, 8 pages.
Office Action for U.S. Appl. No. 15/257,185, dated Aug. 8, 2017, 4 pages.
Office Action for U.S. Appl. No. 15/925,159, dated May 14, 2019, 15 pages.
Office Action for U.S. Appl. No. 15/925,159, dated Nov. 26, 2018, 11 pages.
Office Action for U.S. Appl. No. 16/146,251, dated Dec. 27, 2021, 7 pages.
Opening Expert Report of Dr. Juan G. Santiago Regarding Infringement of U.S. Pat. Nos. 9,855,001 and 10,039,483 (Redacted) in *Magnolia Medical Technologies, Inc. v. Kurin, Inc.*, CA No. 19-00097-CFC (dated Jan. 15, 2021). 555 pages.
Order of Draw for Multiple Tube Collections, LabNotes, a newsletter from BD Diagnostics,—Preanalytical Systems, 17(1):3 (2007).
Original Claims of U.S. Appl. No. 14/712,431, filed May 14, 2015. 6 pages.
Page, C. et al., "Blood conservation devices in critical care: a narrative review," Annals of Intensive Care, 3:14 (2013), 6 pages.
Palavecino, E. L. et al., "Detecting Bacterial Contamination in Platelet Products," Clin. Lab., 52:443-456 (2006).
Pall Corp., "Leukotrap Filtration Systems for Whole Blood Derived Platelets: Leukotrap RC PL and Leukotrap PL Systems," 2005 Brochure, 2 pages.
Patton, R. G. et al., "Innovation for Reducing Blood Culture Contamination: Initial Specimen Diversion Technique," Journal of Clinical Microbiology, 48(12):4501-4503 (2010).
Perez, P. et al., "Multivariate analysis of determinants of bacterial contamination of whole-blood donations," Vox Sanguinis, 82:55-60 (2002).
Proehl, J. A. et al., "Clinical Practice Guideline: Prevention of Blood Culture Contamination, Full Version," 2012 ENA Emergency Nurses Resources Development Committee, Emergency Nurses Association (Dec. 2012), 14 pages.
Quilici, N. et al., "Differential Quantitative Blood Cultures in the Diagnosis of Catheter-Related Sepsis in Intensive Care Units," Clinical Infectious Diseases 25:1066-1070 (1997).
Redacted Plaintiff's Answering Brief in Opposition to Defendant's Motion for Summary Judgement (No. 3) of Noninfringement of All Asserted Claims Due to Lack of Sequestration in *Magnolia Medical*

(56) References Cited

OTHER PUBLICATIONS

*Technologies, Inc.* v. *Kurin, Inc.*, C.A. No. 19-97 (CFC)(CJB), Document 389 (Filed Jul. 14, 2021). 15 pages.
Reexamination Request Order—Granted, for U.S. Appl. No. 90/019,177, mailed Apr. 26, 2023, 16 pages.
Request for Ex Parte Reexamination Under 35 U.S.C. § 302 and 37 C.F.R. § 1.510 filed Mar. 22, 2023, 84 pages.
Schuur, J., "Blood Cultures: When Do they Help and When Do They Harm?" Brigham & Women's Hospital, Department of Emergency Medicine, (Jun. 21-23, 2012), 42 pages.
Sheppard, C. A et al., "Bacterial Contamination of Platelets for Transfusion: Recent Advances and Issues," LabMedicine, 36(12):767-770 (2005).
Shulman, G., "Quality of Processed Blood for Autotransfusion," The Journal of Extra-Corporeal Technology, 32(1): 11-19 (2000).
Sibley, C. D. et al., "Molecular Methods for Pathogen and Microbial Community Detection and Characterization: Current and Potential Application in Diagnostic Microbiology," Infection, Genetics and Evolution 12:505-521 (2012).
Stohl, S. et al., "Blood Cultures at Central Line Insertion in the Intensive Care Unit: Comparison with Peripheral Venipuncture," Journal of Clinical Microbiology, 49(7):2398-2403 (2011).
Tang, M. et al., "Closed Blood Conservation Device for Reducing Catheter-Related Infections in Children After Cardiac Surgery," Critical Care Nurse, 34(5): 53-61 (2014).
Vent Definition & Meaning—Merriam-Webster (https://www.merriam-webster.com/dictionary/vent, accessed Mar. 21, 2023). 16 pages.
Vent, n.2: Oxford English Dictionary (https://www.oed.com/view/Entry/222207?&print, accessed Feb. 16, 2023). 12 pages.
Verdict Form (Phase 2) (Redacted) in *Magnolia Medical Technologies, Inc.* v. *Kurin, Inc.*, CA No. 19-97-CFC (CJB), Document 443 (Filed Jul. 29, 2022). 5 pages.
Verdict Form (Redacted) in *Magnolia Medical Technologies, Inc.* v. *Kurin, Inc.*, C.A. No. 19- 97-CFC (CJB), Document 437 (Filed Jul. 26, 2022). 3 pages.
Wagner et al., "Diversion of Initial Blood Flow to Prevent Whole-Blood Contamination by Skin Surface Bacteria: an in vitro model," Transfusion, 40:335-338 (2000).
Wang, P. et al., "Strategies on Reducing Blood Culture Contamination," Reviews in Medical Microbiology, 23:63-66 (2012).
Weinbaum, F. I. et al., "Doing It Right the First Time: Quality Improvement and the Contaminant Blood Culture," Journal of Clinical Microbiology, 35(3): 563-565 (1997).
Weinstein, M.P., "Current Blood Culture Methods and Systems: Clinical Concepts, Technology, and Interpretation of Results," Clinical Infectious Diseases, 23: 40-46 (1996).
Weinstein, M.P. et al., "The Clinical Significance of Positive Blood Cultures in the 1990s: A Prospective Comprehensive Evaluation of the Microbiology, Epidemiology, and Outcome of Bacteremia and Fungemia in Adults," Clinical Infectious Diseases, 24:584-602 (1997).
Weinstein, M.P., "Minireview: Blood Culture Contamination: Persisting Problems and Partial Progress," Journal of Clinical Microbiology, 41(6): 2275-2278 (2003).
Ziegler, et al., "Controlled Clinical Laboratory Comparison of Two Supplemented Aerobic and Anaerobic Media Used in Automated Blood Culture Systems to Detect Bloodstream Infections," J. Clinical Microbiology, 36(3):657-661 (1998).
Zimmon, D. S. et al., "Effect of Portal Venous Blood Flow Diversion on Portal Pressure," J Clin Invest, 65(6): 1388-1397 (1980).
Zundert, A. V., "New Closed IV Catheter System," Acta Anaesth. Belg., 56: 283-285 (2005).
Arenas et al., "Asynchronous Testing of 2 Specimen-Diversion Devices to reduce Blood Culture Contamination: A Single-Site Product Supply Quality Improvement Project," J. Emergency Nursing, vol. 47, No. 2, pp. 256-264.e6 (Mar. 2021), 15 pages.
Bauman et al., "Don't Stick Me Again! Reducing Blood Culture Contamination," INOVA Fairfax Medical Campus, Emergency Department (2019), 1 page.
Bell et al., Effectiveness of a Novel Specimen Collection System in Reducing Blood Culture Contamination Rates, J. Emergency Nursing, vol. 44, No. 6, 570 (Nov. 2018), 6 pages.
Blakeney, "Reduction of Blood Culture Contaminations Using Initial Specimen Diversion Device," Beebe Healthcare (Jun. 2018), 1 page.
Brownfield et al., "Emergency Department Observes 83% Reduction in Blood Culture Contamination with Initial Specimen Diversion Technology Adoption," Am. J. Infection Control, vol. 49, S14, Ads 34 (Jun. 2021), 1 page.
Case 1: 19-cv-00097-CFC-CJB, *Magnolia Medical Technologies, Inc.*, Plaintiff v. *Kurin, Inc.*, Defendant; Memorandum Opinion, (Document 514) filed Aug. 4, 2023, 38 pages.
Case 1: 19-cv-00097-CFC-CJB, *Magnolia Medical Technologies, Inc.*, Plaintiff v. *Kurin, Inc.*, Defendant; Order, (Document 515) filed Aug. 4, 2023, 1 page.
Case 1: 19-cv-00097-CFC-CJB, *Magnolia Medical Technologies, Inc.*, Plaintiff v. *Kurin, Inc.*, Defendant; Order, (Document 516) filed Aug. 4, 2023, 2 pages.
Chang et al., "Impact of Blood Culture Diversion Device and Molecular Pathogen Identification on Vancomycin Use," San Antonio Military Medical Center (2016), 1 page.
Claim Construction Order, *Magnolia Medical Techs*. v. *Kurin*, Case No. 19-00097-CFC-CJB, at 3 (D. Del.) (May 20, 2020), 4 pages.
Declaration of Dr. Morten Jensen under 37 C.F.R. § 1.132, Oct. 10, 2023, 400 pages.
Doern et al., "A Comprehensive Update on the Problem of Blood Culture Contamination and a Discussion of Methods for Addressing the Problem," Clinical Microbiology, vol. 33, No. 1, e00009-19 (Jan. 2020), 21 pages.
Extended European Examination Report for EP Application No. 23173044.1, dated Oct. 27, 2023, 8 pages.
Extended European Search Report for European Application No. EP 2023029844.2 dated Mar. 20, 2024, 9 pages.
Geisler et al., "Model to Evaluate the Impact of Hospital-Based Interventions Targeting False-Positive Blood Cultures on Economic and Clinical Outcomes," J. Hospital Infection, vol. 102, No. 4, pp. 438-444 (Mar. 2019).
JP Application No. 2023-075104 Notice of Reasons for Rejection dated Feb. 29, 2024, mailed Mar. 5, 2024, with English Translation, 9 pages.
Lanteri et al., "Reduction of Blood Culture Contaminations in the Emergency Department," Department of Emergency Medicine, San Antonio Military Medical Center (2016), 1 page.
Nielsen et al., "Initial Specimen Diversion Device Reduces Blood Culture Contamination and Vancomycin Use in Academic Medical Centre," J. Hospital Infection, vol. 120:127-133 (Feb. 2022).
Non-Final Office Action for U.S. Appl. No. 17/136,882, dated Apr. 19, 2024, 8 pages.
Non-Final Office Action for U.S. Appl. No. 18/227,185 dated Apr. 18, 2024, 18 pages.
Office Action and Search report for Chinese Application No. CN202011295348 dated Nov. 29, 2023, 10 pages.
Office Action in Ex Parte Reexamination for U.S. Appl. No. 90/019,177, dated Aug. 9, 2023, 11 pages.
Povroznik, "Initial Specimen Diversion Device Utilization Mitigates Blood Culture Contamination Across Regional Community Hospital and Acute Care Facility," Am. J. Medical Quality, vol. 37, No. 5, 405 (Mar. 2022), 8 pages.
Rupp et al., "Reduction in Blood Culture Contamination Through Use of Initial Specimen Diversion Device," Clinical Infectious Diseases, vol. 65, No. 2, 201 (Jul. 15, 2017), 19 pages.
Skoglund et al., "Estimated Clinical and Economic Impact through Use of a Novel Blood Collection Device to Reduce Blood Culture Contamination in the Emergency Department: a Cost-Benefit Analysis," J Clin Microbiol. (Jan. 2019); 57(1):e01015-18, 10 pages.
Steed et al., "Study Demonstrates Reduction in Blood Culture Contamination Rates with Novel Blood Culture Collection Device," Clinical Lab Products Magazine (Feb. 2018), 2 pages.
Tompkins et al., "Getting to Zero: Impact of a Device to Reduce Blood Culture Contamination and False-Positive Central-Line-Associated Bloodstream Infection," Infection Control & Hospital Epidemiology, pp. 1-5 (Nov. 2022).

(56) References Cited

OTHER PUBLICATIONS

Tongma et al., "Significant Reduction of Blood Culture Contamination in the Emergency Department (ED) Using the Steripath® Blood Diversion Device," Open Forum Infectious Diseases, vol. 4, Supp. 1, 2035 (Oct. 2017), 1 page.
U.S. Appl. No. 18/399,007 Non-Final Office Action dated Mar. 7, 2024, 8 pages.
U.S. Appl. No. 18/407,010 Non-Final Office Action dated Mar. 13, 2024, 8 pages.
Zimmerman et al., "Reducing Blood Culture Contamination Using an Initial Specimen Diversion Device," Am. J. Infection Control, vol. 47, No. 7, pp. 822-826 (Jan. 2019).

\* cited by examiner

APPARATUS AND METHODS FOR MAINTAINING STERILITY OF A SPECIMEN CONTAINER

CROSS-REFERENCE TO RELATED APPLICATIONS

This application is a continuation of U.S. patent application Ser. No. 15/925,159 entitled, "Apparatus and Methods for Maintaining Sterility of a Specimen Container," filed Mar. 19, 2018, which is a divisional of U.S. patent application Ser. No. 15/257,185 entitled, "Apparatus and Methods for Maintaining Sterility of a Specimen Container," filed Sep. 6, 2016, now U.S. Pat. No. 9,950,084, which claims priority to and the benefit of U.S. Provisional Patent Application Ser. No. 62/213,875 entitled, "Apparatus and Methods for Maintaining Sterility of a Specimen Container," filed Sep. 3, 2015, the disclosure of each of which is incorporated herein by reference in its entirety.

BACKGROUND

Embodiments described herein relate generally to the parenteral procurement of bodily-fluid samples, and more particularly to systems and methods for parenterally-procuring bodily-fluid samples with reduced contamination from microbes or other contaminants exterior to the bodily-fluid source that can potentially distort the results of diagnostic testing in a healthcare setting.

Health care practitioners routinely perform various types of microbial as well as other broad diagnostic tests on patients using parenterally-obtained bodily-fluids. As advanced diagnostic technologies evolve and improve, the speed and value of information that can be provided to clinicians continues to improve. As such, ensuring that the bodily-fluid sample to be analyzed is collected in a fashion that maintains specimen integrity similarly ensures that analytical diagnostic results are representative of the in vivo conditions of a patient. Examples of diagnostic technologies that are reliant on high quality, non-contaminated bodily-fluid samples include but are not limited to microbial detection, molecular diagnostics, genetic sequencing (e.g., DNA, RNA), and the like. When biological matter, cells external to the intended source for sample procurement, and/or other external contaminants are inadvertently included in the bodily-fluid sample that is to be analyzed, the opportunity for an adulterated specimen driving a potentially inaccurate patient diagnosis may occur.

In some instances, patient samples (e.g., bodily-fluids) are tested for the presence of one or more potentially undesirable microbes, such as bacteria, fungi, or yeast (e.g., *Candida*). Microbial testing may include incubating patient samples in one or more sterile and/or non-sterile vessels containing culture media or other types of solutions that are conducive to microbial growth and/or other real-time diagnostic approaches including molecular polymerase chain reaction-based (PCR-based) and/or other technologies (e.g. magnetic resonance, automated microscopy, spatial clone isolation, etc.) used to rapidly detect and identify organisms. Generally, when microbes tested for are present in the patient sample, the microbes flourish over time in the culture medium. These organisms may also be identified by other advanced diagnostic testing technologies (e.g., molecular diagnostics, PCR, genetic testing/sequencing, magnetic resonance, automated microscopy, spatial clone isolation, etc.). In the case of employing a culture medium, after an amount of time (e.g., a few hours to several days—which can be longer or shorter depending on the diagnostic technology employed), organism growth can be detected by automated, continuous monitoring. For example, in some instances, such automated monitoring can detect carbon dioxide produced by organism growth. The presence of microbes in the culture medium (as indicated by observation of carbon dioxide) and/or via other detection methods suggests the presence of the same microbes in the patient sample which, in turn, suggests the presence of the same microbes in the bodily-fluid of the patient from which the sample was obtained. Accordingly, when microbes are determined to be present in the culture medium (or more generally in the sample used for testing), the patient may be prescribed one or more antibiotics or other treatments specifically designed to treat or otherwise remove the undesired microbes from the patient.

Generally, patient bodily-fluid samples are collected in various settings and are then transported to a laboratory-type environment for processing and analysis. For example, the settings for collecting the patient sample(s) could include an outpatient clinic, a hospital (including emergency department, intensive care unit (ICU), medical/surgical floor, or the like) or a commercial setting (including a drugstore or any other commercial enterprise that assists with collection of bodily-fluid sample(s)). In all settings, typically, protocols are developed, implemented, and monitored to ensure the quality of the collection, handling, preparation, transportation, etc. of a patient's bodily-fluid sample(s). Generally, practitioners attempt to ensure the integrity of the patient specimen(s), understanding that if the sample is adulterated and/or contains matter that is not representative of the patient's in vivo condition, a diagnostic error and ensuing inaccurate treatment decision(s) may occur.

In some instances, patient samples, nonetheless, can become contaminated during procurement. For example, some equipment used in phlebotomy procedures can include multiple fluidic interfaces (e.g., patient to needle, peripheral IV to catheter, needle/tubing to sample vessels, etc.) that can each introduce points of potential contamination. Additionally, the equipment used to procure, transfer, transport, and/or otherwise contain a patient sample are typically connected and/or otherwise placed in fluid communication via manual intervention (e.g., a doctor, phlebotomist, nurse, etc. handles and/or manipulates the equipment). Since the interfaces of the equipment are not consistently preassembled and/or sterilized as a single fluidically coupled system, external contaminants (e.g., microbes, dermally-residing organisms, cells from the patient that are not from the intended source of bodily-fluid to be tested, etc.) can be introduced to the patient sample via multiple sources (e.g. ambient air, contaminants on surfaces of tables and/or counters in patient room, microbes transferred from linens or clothing, skin deposited on collection supplies from a healthcare worker during assembly and/or sample procurement or transfer, cells from another source within the patient, and/or the like). In some instances, the contaminants can lead to a positive microbial and/or other diagnostic test result, thereby falsely indicating the presence of such microbes or other cells and/or other biological matter in vivo. Such inaccurate results are a concern when attempting to diagnose or treat a suspected illness or condition. For example, false positive results from microbial tests may result in the patient being unnecessarily subjected to one or more anti-microbial therapies, which may cause serious side effects to the patient including, for example, death, as well as produce an unnecessary burden and expense to the healthcare system.

As such, a need exists for improved systems and methods for disinfection of specimen container(s) that reduce microbial and/or any other types of contamination associated with the collection of bodily-fluid test samples by, for example, disinfecting equipment and/or fluidic interfaces to ensure the integrity of the patient sample(s) that are collected and analyzed in diagnostic processes to minimize and/or substantially eliminate false positive as well as false negative diagnostic results.

SUMMARY

Apparatus and methods for parenterally-procuring bodily-fluid samples with reduced contamination from microbes exterior to the bodily-fluid source and/or other undesirable external contaminants or biological matter are described herein. In some embodiments, an apparatus includes a fluid reservoir, a sterilization member, and a transfer adapter. The fluid reservoir has an inlet surface and is configured to receive a volume of bodily-fluid transferred from a patient. The sterilization member operably couples to the fluid reservoir and defines at least a portion of a substantially sterile environment. The sterilization member is configured to be transitioned between a first configuration, in which the sterilization member obstructs the inlet surface and maintains the inlet surface in the substantially sterile environment, and a second configuration, in which the inlet surface is unobstructed. The transfer adapter is configured to be placed in fluid communication with a portion of a patient. The transfer adapter is configured to move relative to the sterilization member from a first position to a second position. A surface of the transfer adapter is configured to contact the sterilization member as the transfer adapter moves to the second position to transition the sterilization member from the first configuration to the second configuration. The fluid reservoir is placed in fluid communication with the transfer adapter when the transfer adapter is in the second position.

DETAILED DESCRIPTION

Figure 1:
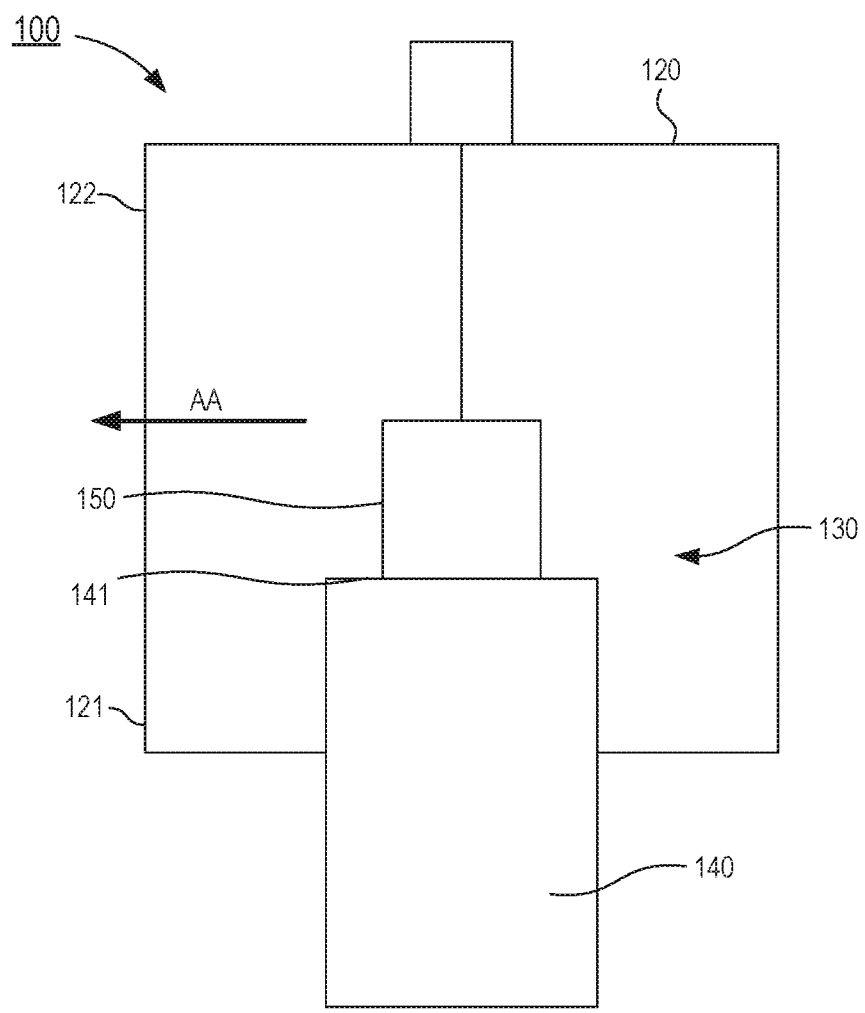
FIG. 1 is a schematic illustration of a bodily-fluid collection device according to an embodiment.

In some embodiments, an apparatus includes a fluid reservoir, a sterilization member, and a transfer adapter. The fluid reservoir has an inlet surface and is configured to receive a volume of bodily-fluid transferred from a patient. The sterilization member operably couples to the fluid reservoir and defines at least a portion of a substantially sterile environment. The sterilization member is configured to be transitioned between a first configuration, in which the sterilization member obstructs the inlet surface and maintains the inlet surface in the substantially sterile environment, and a second configuration, in which the inlet surface is unobstructed. The transfer adapter is configured to be placed in fluid communication with a portion of a patient. The transfer adapter is configured to move relative to the sterilization member from a first position to a second position. A surface of the transfer adapter is configured to contact the sterilization member as the transfer adapter moves to the second position to transition the sterilization member from the first configuration to the second configuration. The fluid reservoir is placed in fluid communication with the transfer adapter when the transfer adapter is in the second position.

In some embodiments, a system for parenterally-procuring bodily-fluid samples with reduced contamination from microbes exterior to the bodily-fluid source includes a sample reservoir, a handle, and an adapter. The handle is configured to be placed in fluid communication with a patient. The handle has a coupler, a fluid reservoir, and an actuator. The fluid reservoir is disposed within the handle and configured to receive a volume of bodily-fluid from the patient. The actuator is configured to be transitioned between a first configuration, in which the coupler is fluidically isolated from the fluid reservoir, and a second configuration, in which the coupler is in fluid communication with the fluid reservoir. The adapter is configured to be coupled to the coupler of the handle. The adapter is at least temporarily coupled to a sterilization member and to the sample reservoir such that an inlet surface of the sample reservoir is maintained in a substantially sterile environment collectively defined by the adapter and the sterilization member prior to the adapter being coupled to the coupler of the handle. The sterilization member is at least partially removed from the adapter when the adapter is coupled to the coupler of the handle.

In some embodiments, a method for parenterally-procuring bodily-fluid samples with reduced contamination from microbes exterior to the bodily-fluid source includes establishing fluid communication between a patient and a first fluid reservoir, which in turn, is in selective fluid communication with a transfer adapter. A volume of bodily-fluid is withdrawn from the patient and into the first fluid reservoir. A second fluid reservoir is coupled to the to the transfer adapter. The second fluid reservoir has an inlet surface and is coupled to a sterilization member configured to at least temporarily obstruct the inlet surface. The sterilization member is moved relative to the inlet surface such that the inlet surface is unobstructed by the sterilization member as the second fluid reservoir is coupled to the transfer adapter. The second fluid reservoir is placed in fluid communication with the transfer adapter when the portion of the second fluid reservoir is coupled to the transfer adapter and the inlet surface is unobstructed by the sterilization member. Fluid communication between the first fluid reservoir and the second fluid reservoir is established and a volume of bodily-fluid is transferred from the first fluid reservoir to the second fluid reservoir.

In some embodiments, an apparatus includes a sterilization and/or disinfection member at least temporarily coupled to a sample reservoir. The sample reservoir includes an inlet port that is configured to be fluidically coupled to a transfer device to receive a volume of bodily-fluid directly from a patient or indirectly from the patient via an intermediary bodily-fluid collection device. The sterilization and/or disinfection member is configured to be placed in contact with the transfer device and transitioned from a first configuration, in which the sterilization and/or disinfection member fluidically isolates the inlet port of the fluid reservoir, to a second configuration, in which at least a portion of the sterilization and/or disinfection member is spaced apart from the sample reservoir. The sample reservoir is configured to be placed in fluid communication with the transfer device via the inlet port when the sterilization and/or disinfection member is in the second configuration.

In some embodiments, a sterilization and/or disinfection member is coupled to a sample reservoir during a manufacturing process in a position that prevents the clinician from collecting and/or transferring a bodily-fluid sample into a fluid reservoir(s) without engaging the sterilization and/or disinfection member to at least substantially sterilize a connection therebetween, which in turn, facilitates fluid communication of a bodily-fluid sample between the patient and the collection vessel. By ensuring that substantially no external contaminants and/or biological matter (e.g., skin cells, tumor cells, organ tissue, etc.) external to the target bodily-fluid source are captured in the sample vessel, diagnostic results can improve with increased consistency. With accurate diagnostic results, clinicians can derive an accurate treatment/action plan, thereby reducing the likelihood of misdiagnosing a patient, prescribing unnecessary treatment, holding the patient in a clinical and/or hospital setting for an undue and/or unnecessary period of time, and/or the like, which in turn, can substantially reduce a risk of the patient developing a further ailment (e.g., antibiotic complications, adverse drug reactions, hospital-acquired infection, and/or the like) as well as substantially reduce costs to hospital and/or other healthcare institutions, third party payers and the healthcare systems as a whole.

As used in this specification, the singular forms "a," "an" and "the" include plural referents unless the context clearly dictates otherwise. Thus, for example, the term "a member" is intended to mean a single member or a combination of members, "a material" is intended to mean one or more materials, or a combination thereof.

As referred to herein, "bodily-fluid" can include any fluid obtained from a body of a patient, including, but not limited to, blood, cerebrospinal fluid, urine, bile, lymph, saliva, synovial fluid, serous fluid, pleural fluid, amniotic fluid, and the like, or any combination thereof.

As used herein, the term "set" can refer to multiple features or a singular feature with multiple parts. For example, when referring to set of walls, the set of walls can be considered as one wall with distinct portions, or the set of walls can be considered as multiple walls. Similarly stated, a monolithically constructed item can include a set of walls. Such a set of walls can include, for example, multiple portions that are in discontinuous from each other. A set of walls can also be fabricated from multiple items that are produced separately and are later joined together (e.g., via a weld, an adhesive or any suitable method).

As used herein, the words "proximal" and "distal" refer to the direction closer to and away from, respectively, a user who would place the device into contact with a patient. Thus, for example, the end of a device first touching the body of the patient would be the distal end, while the opposite end of the device (e.g., the end of the device being manipulated by the user) would be the proximal end of the device.

As used herein, the term "disinfecting agent" refers to a chemical or combination of chemicals used to disinfect and/or to substantially sterilize or maintain the sterility of a surface. A disinfecting agent can be in any suitable form (e.g., gaseous, aqueous, or solid). In some embodiments, a disinfecting agent can be an antiseptic or the like that can be used to kill, destroy, and/or otherwise substantially neutralize negative effects from microbes such as, for example, germs, bacteria, viruses, and/or other target microorganisms. In some embodiments, a disinfecting agent can be in an aqueous form and substantially suspended by a porous substrate. In other embodiments, a surface of a substrate such as a wipe or diaphragm can be impregnated by and/or coated with a disinfecting agent. A non-limiting list of disinfecting agents can include, for example, alcohol (e.g., ethanol, 1-propanol, 2-proponal, isopropanol, and/or the like), quaternary ammonium compounds ((e.g., benzalkonium chloride (BAC), cetyl trimethylammonium bromide (CTMB), cetylpyridinium chloride (Cetrim (CPC)), benzethonium chloride (BZT) and/or the like), boric acid, chlorhexidine gluconate, hydrogen peroxide, iodine, octenidine dihydrochloride, phenol, polyhexanide (e.g., polyhexamethylene biguanide (PHMB)), sodium bicarbonate, silver compounds (e.g., silver nitrate, silver proteinate, chlorhexidine-silver-sulfadiazine, and/or the like), and/or any other suitable disinfectant or antiseptic, and/or a combination thereof. Moreover, any of the disinfecting agents can be used with, for example, a binding agent, a suspension agent, a surfactant, and/or the like.

FIG. 1 is a schematic illustration of a bodily-fluid collection device 100, according to an embodiment. Generally, the bodily-fluid collection device 100 (also referred to herein as "collection device") is configured to disinfect and/or otherwise maintain the sterility of one or more interfaces prior to defining a fluidic coupling to reduce external contaminants residing on the interfaces. Once disinfected, the one or more interfaces can be fluidically coupled to allow a flow of bodily-fluid that is substantially free of external contaminants to flow from a patient to a fluid reservoir either directly or via an intermediary device.

The collection device 100 includes a transfer adapter 120, a fluid reservoir 140, and a sterilization and/or disinfection member 150. The transfer adapter 120 has a proximal end portion 121 and a distal end portion 122, and defines an inner volume 130 therebetween. The transfer adapter 120 can be any suitable shape, size, or configuration. For example, the transfer adapter 120 can be substantially cylindrical, including a set of annular walls that define at least a portion of the inner volume 130. In other embodiments, the transfer adapter 120 can be polygonal such as rectangular, pentagonal, octagonal, etc. Moreover, as shown in FIG. 1, the transfer adapter 120 (and/or a set of walls of the transfer adapter 120) can house and/or receive at least a portion of the fluid reservoir 140 and the sterilization and/or disinfection member 150. Although not shown in FIG. 1, in some embodiments, the transfer adapter 120 can include and/or can be coupled to a puncture member, port, and/or any other suitable transfer device configured to fluidically couple the transfer adapter 120 to an inner volume (not shown) of the fluid reservoir 140 (e.g., a needle that can puncture a port, septum, or portion of the fluid reservoir 140).

The proximal end portion 121 of the transfer adapter 120 can be substantially open to movably receive at least a portion of the fluid reservoir 140. In other words, at least a portion of the fluid reservoir 140 can be inserted through the proximal end portion 121 of the transfer adapter 120 to dispose that portion of the fluid reservoir 140 within the inner volume 130. As described in further detail herein, once the portion of the fluid reservoir 140 is disposed within the inner volume 130 of the transfer adapter 120, the fluid reservoir 140 can be moved from a first position in which the sterilization and/or disinfection member 150 obstructs, covers, engages, disinfects, and/or otherwise substantially maintains the sterility of a port of the fluid reservoir 140 to a second position in which the sterilization and/or disinfection member 150 is at least partially disengaged from the fluid reservoir 140 to allow access to the port.

Although not shown in FIG. 1, the distal end portion 122 of the transfer adapter 120 can be physically and fluidically coupled to any suitable lumen-defining device (e.g., as a catheter, cannula, needle, trocar, or the like), collection device, transfer device, diversion device, and/or the like. For example, in some embodiments, the distal end portion 122 of the transfer adapter 120 can include a port such as a Luer Lok® that can be physically and fluidically coupled to a device configured to receive a flow of bodily-fluids from a patient.

In some embodiments, the transfer adapter 120 can be physically and fluidically coupled to a transfer device that includes and/or is coupled to a peripheral intravenous (IV) needle or a peripheral IV catheter, which places the transfer device in fluid communication with a portion of the patient. In other embodiments, the transfer adapter 120 can be placed in fluid communication with any suitable intermediary device, which contains and/or receives a bodily-fluid collected from a patient in a separate and/or independent step. In some embodiments, the intermediary device can be a collection device, a diversion device, a syringe-based collection device and/or the like such as those described in U.S. Pat. No. 8,535,241 entitled, "Fluid Diversion Mechanism for Bodily-Fluid Sampling," filed Sep. 17, 2013 (the "'241 patent"); U.S. Pat. No. 9,060,724 entitled, "Fluid Diversion Mechanism for Bodily-Fluid Sampling," filed May 29, 2013 (the "'724 patent"); U.S. Pat. No. 9,204,864 entitled, "Fluid Diversion Mechanism for Bodily-Fluid Sampling," filed Jul. 29, 2013 (the "'864 patent"); U.S. Patent Publication No. 2014/0155782 entitled, "Sterile Bodily-Fluid Collection Device and Methods," filed Dec. 4, 2013 (the "'782 publication"); and/or U.S. Pat. No. 9,155,495 entitled, "Syringe-Based Fluid Diversion Mechanism for Bodily-Fluid Sampling," filed Dec. 2, 2013 (the "'495 patent"), the disclosures of which are incorporated herein by reference in their entireties. In addition, the transfer adapter 120 can include a puncture member or the like (as described above) in fluid communication with such a transfer device, which in turn, can puncture a portion, surface, and/or port of the fluid reservoir 140 to establish fluid flow path between the patient and the fluid reservoir 140. Although described as being physically and fluidically coupled to a transfer device, in other embodiments, the transfer adapter 120 can be monolithically formed with a transfer device. In still other embodiments, the transfer adapter 120 can be operably coupled to a transfer device via any suitable intervening structure (e.g., via sterile flexible tubing, one or more cannulas, one or more intermediate devices, one or more fluid reservoirs, and/or the like).

Although not shown in FIG. 1, the transfer adapter 120 can include one or more seals and/or disinfection members removably coupled to a surface of the transfer adapter 120, which, prior to use, can fluidically isolate the inner volume 130 from a volume outside of the transfer adapter 120. For example, in some embodiments, the proximal end portion 121 of the transfer adapter 120 can include a seal and/or disinfection member that can be removably coupled to a proximal surface of the transfer adapter 120 to substantially cover an opening defined by the proximal end portion 121. Such a seal can be, for example, a housing, a cap, a relatively thin sheet or film, Tyvek® material, an elastomeric member (e.g., a plunger or stopper), and/or the like. As such, the seal can fluidically isolate the inner volume 130 to substantially maintain the sterility of the inner volume 130 prior to use. In some embodiments, the transfer adapter 120 can include any of the seals and/or disinfection members described in U.S. Patent Publication No. 2015/0246352 entitled, "Apparatus and Methods for Disinfection of a Specimen Container," filed Mar. 3, 2015, the disclosure of which is incorporated herein by reference in its entirety.

As described above, the fluid reservoir 140 is configured to be placed in fluid communication with the transfer adapter 120 to, for example, receive a volume of bodily-fluid from a patient. In some embodiments, the fluid reservoir 140 includes a surface 141 that can be pierced, punctured, and/or otherwise placed in an open configuration to place an inner volume of the fluid reservoir 140 in fluid communication with a volume outside of the fluid reservoir 140. For example, in some embodiments, the surface 141 can include and/or can define a frangible portion, a port, a septum, and/or the like that can be pierced, for example, by a puncture member included in the transfer adapter 120 to place the inner volume of the fluid reservoir 140 in fluid communication with transfer adapter 120 and any suitable device coupled thereto, as described in further detail herein.

The fluid reservoir 140 can be any suitable shape, size, and/or configuration that can receive and/or store a volume of a bodily-fluid. For example, in some embodiments, the fluid reservoir 140 can be any suitable reservoir described in U.S. Pat. No. 8,197,420 ("the '420 patent"), entitled, "Systems and Methods for Parenterally Procuring Bodily-Fluid Samples with Reduced Contamination," filed on Dec. 13, 2007, the disclosure of which is incorporated herein by reference in its entirety. In some embodiments, the fluid reservoir 140 can define a negative pressure and/or otherwise can be substantially evacuated. For example, in some embodiments, the fluid reservoir 140 can be a BacT/ALERT® SN or a BacT/ALERT® FA (manufactured by BIOMERIEUX, INC.), a BD Vacutainer® or a BD Microtainer® (manufactured Becton, Dickinson, and Company (BD)), a Nanotainer™ (manufactured by Theranos), and/or any suitable reservoir, syringe, vial, microvial, microliter vial, container, microcontainer, or the like.

In some embodiments, the fluid reservoir 140 can be any suitable sample or culture bottle such as, for example, an aerobic or anaerobic culture bottle containing a culture medium. In such embodiments, a bodily-fluid sample volume can be delivered and/or transferred into the a culture bottle (e.g., the fluid reservoir 140) and after a given time, incubation period, or the like, microbes contained in the bodily-fluid sample can flourish or grow within the culture medium. After the incubation period, the bodily-fluid sample can be tested to determine quantitative and/or qualitative information associated with such microbial growth within the culture medium. In some instances, for example, the bodily-fluid samples can be tested via real-time diagnostics including molecular PCR-based technologies, genetic testing/diagnostics, and/or any other suitable test. In some instances, results of such testing can be indicative of the presence of Gram-Positive bacteria, Gram-Negative bacteria, fungi, yeast (e.g., *Candida*), and/or any other contaminants or organisms contained within the bodily-fluid sample, which in turn, is indicative of their presence within the patient. As described above, however, contaminants or microbes external to the body of the patient that are transferred into the inner volume of fluid reservoir 140 and/or otherwise entrained in the flow of the bodily-fluid sample can result in false positive or false negative results when testing bodily-fluid sample. Thus, disposing the sterilization and/or disinfection member 150 about a fluidic interface of the fluid reservoir 140 (e.g., at least a portion of the surface 141) prior to use can reduce a likelihood of such contaminants being transferred into the fluid reservoir 140, as described in further detail herein.

The sterilization and/or disinfection member 150 can be any suitable sterilization and/or disinfection member and/or mechanism that is at least temporarily coupled to a portion of the fluid reservoir 140 to at least temporarily maintain a sterility of the portion of the fluid reservoir 140. In some embodiments, the sterilization and/or disinfection member 150 can disinfect the portion of the fluid reservoir 140 to remove contaminants and/or the like. The sterilization and/or disinfection member 150 (also referred to herein as "sterilization member") can be, for example, a pad, a swab, a diaphragm, a sponge, a wipe, a cap, a foil, and/or the like that can include and/or the can at least partially house a disinfecting agent. In some embodiments, the sterilization member 150 can be a diaphragm or the like that can have at least one surface that is substantially impregnated with a disinfecting agent such as those described above. In some embodiments, the sterilization member 150 can include and/or can define a portion that is substantially porous, for example, to act as a substrate for the disinfection agent. In other embodiments, the sterilization member 150 can include a surface that is formed from a disinfecting material such as, for example, a silver compound.

In some embodiments, the sterilization member 150 can be a sheet, foil, cap, membrane, diaphragm, and/or the like that can form a substantially fluid tight seal with a portion of the fluid reservoir 140. For example, the sterilization member 150 can be coupled to, in contact with, and/or otherwise disposed about at least a portion of the surface 141 of the fluid reservoir 140 such that at least the portion of the surface 141 is maintained in a substantially sterile environment prior to use. For example, in some embodiments, such a sterilization member 150 can be coupled to the fluid reservoir 140 during a manufacturing process performed in a substantially sterile environment. In some embodiments, a disinfecting agent can be disposed within the volume at least partially circumscribed by a seal formed by the sterilization member 150 (e.g., ethylene oxide gas, gamma radiation or the like can be used to create a sterile environment within the inner volume).

In use, a user (e.g., a doctor, nurse, technician, physician, phlebotomist, etc.) can manipulate the collection device 100 to at least indirectly couple the transfer adapter 120 to a lumen-defining device, transfer device, collection device, diversion device, etc. such as, for example, a standard winged butterfly needle, a syringe, a peripheral IV catheter, and/or the like. In some embodiments, such a device can be any of those described in the '241 patent, the '724 patent, the '348 publication, the '782 publication, and/or the '419 publication. In some instances, such a device can be placed in communication with a patient prior to being coupled to the transfer adapter 120. In other instances, the transfer adapter 120 can be coupled to, for example, a needle or cannula prior to being inserted (e.g., percutaneously) into the patient. With the transfer adapter 120 in fluid communication with the patient, the user can manipulate the collection device 100 to insert at least a portion of the fluid reservoir 140 into the proximal end portion 121 of the transfer adapter 120. In some embodiments, prior to inserting the fluid reservoir 140, the user can manipulate the collection device 100 to remove, for example, a seal that substantially covers the proximal end 121 of the transfer adapter 120, as described above.

The user can move the fluid reservoir 140 relative to the transfer adapter 120 to place the fluid reservoir 140 in a first position within the inner volume 130, thereby placing the collection device 100 in a first configuration. In some instances, the sterilization member 150 can be placed in contact with a portion of the transfer adapter 120 such as an inner surface and/or any suitable feature extending from the inner surface when the collection device 100 is in the first configuration. For example, as described above, in some embodiments, the inner surface of the transfer adapter 120 can include a surface feature, contour, protrusion, slot, cutting member, peeling member, and/or the like configured to engage the sterilization member 150 as the fluid reservoir 140 is inserted and/or moved within the inner volume 130 of the transfer adapter 120. In some instances, the user can maintain the fluid reservoir 140 in the first position for a predetermined time (which in some embodiments, is facilitated by physical design characteristics that prevent the user from bypassing the first position) to ensure the sterilization member 150 is engaged with and/or otherwise in contact with a desired portion of the transfer adapter 120 prior to moving the fluid reservoir 140 from the first position to a second position within the transfer adapter 120. In other embodiments, the fluid reservoir 140 need not be held in the first position for the predetermined time. That is to say, in some embodiments, the user can move the fluid reservoir 140 relative to the transfer adapter 120 (or vice versa) in a substantially continuous manner to move the fluid reservoir 140 through the first position and into the second position.

Once the fluid reservoir 140 has been placed at or near a desired position within the transfer adapter 120, a portion of the surface 141 (e.g., a portion including a port, septum, seal, etc.) can be exposed and/or otherwise unobstructed by the sterilization member 150. In other words, placing the fluid reservoir 140 in a desired position within the transfer adapter 120 can transition the sterilization member 150 from a first configuration, in which the sterilization member 150 engages the surface 141 to substantially maintain the sterility of at least a portion of the surface 141, to a second configuration, in which at least a portion of the sterilization member 150 is disengaged from the surface 141. Specifically, the transfer adapter 120 can remove at least a portion of the sterilization member 150 from contact with the surface 141 as the fluid reservoir 140 is placed in the second position, as indicated by the arrow AA in FIG. 1.

With the sterilization member 150 in, for example, the second configuration, a user can then manipulate the transfer adapter 120 and/or the fluid reservoir 140 to place the fluid reservoir 140 in fluid communication with the transfer adapter 120, as described in detail above. Thus, the collection device 100 can be used to maintain the sterility of a fluidic interface associated with the surface 141 of the fluid reservoir 140 to reduce the likelihood of contamination from microbes disposed on the surface 141. By having the sterilization member 150 coupled to the fluid reservoir 140 prior to use, contamination of a sample of bodily-fluid can be reduced that might otherwise result from insufficient disinfection by a user. In addition, having the transfer adapter 120 automatically remove the sterilization member 150 as the fluid reservoir 140 is moved relative to the transfer adapter 120 can ensure compliance with a substantially consistent sterilization and/or disinfection process, which in turn, can reduce inaccurate test results, costs, and time associated with collecting and testing a sample volume.

In some embodiments, the collection device 100 and/or the transfer adapter 120 can be included in and/or can form at least a portion of a preassembled and/or all-in-one collection device. In such embodiments, the preassembled and/or all-in-one collection device can include, for example, any suitable number of fluid reservoirs (e.g., one fluid reservoir, two fluid reservoirs, three fluid reservoirs, four fluid reservoirs, or more) that can be preassembled with and/or incorporated in (e.g., unitarily formed with) a transfer device including a sterilization and/or disinfection member such as those described herein. By way of example, in some embodiments, the collection device 100 (and/or any suitable portion thereof) can be included in and/or can otherwise form a portion of a preassembled and/or all-in-one collection device such as those described in '782 publication incorporated by reference above.

While described above as maintaining at least a portion of the surface 141 of the fluid reservoir 140 in a substantially sterile environment, in some embodiments, the sterilization member 150 can be configured to disinfect the surface 141 of the fluid reservoir 140. That is to say, the sterilization member 150 can be used to remove contaminants from the surface 141 of the fluid reservoir 140 (i.e., to disinfect the surface 141 of the fluid reservoir 140). The sterilization and/or disinfection members described herein, therefore, are not intended to be limited to either function and, for simplicity, are referred to henceforth as "sterilization members."

Figure 2:
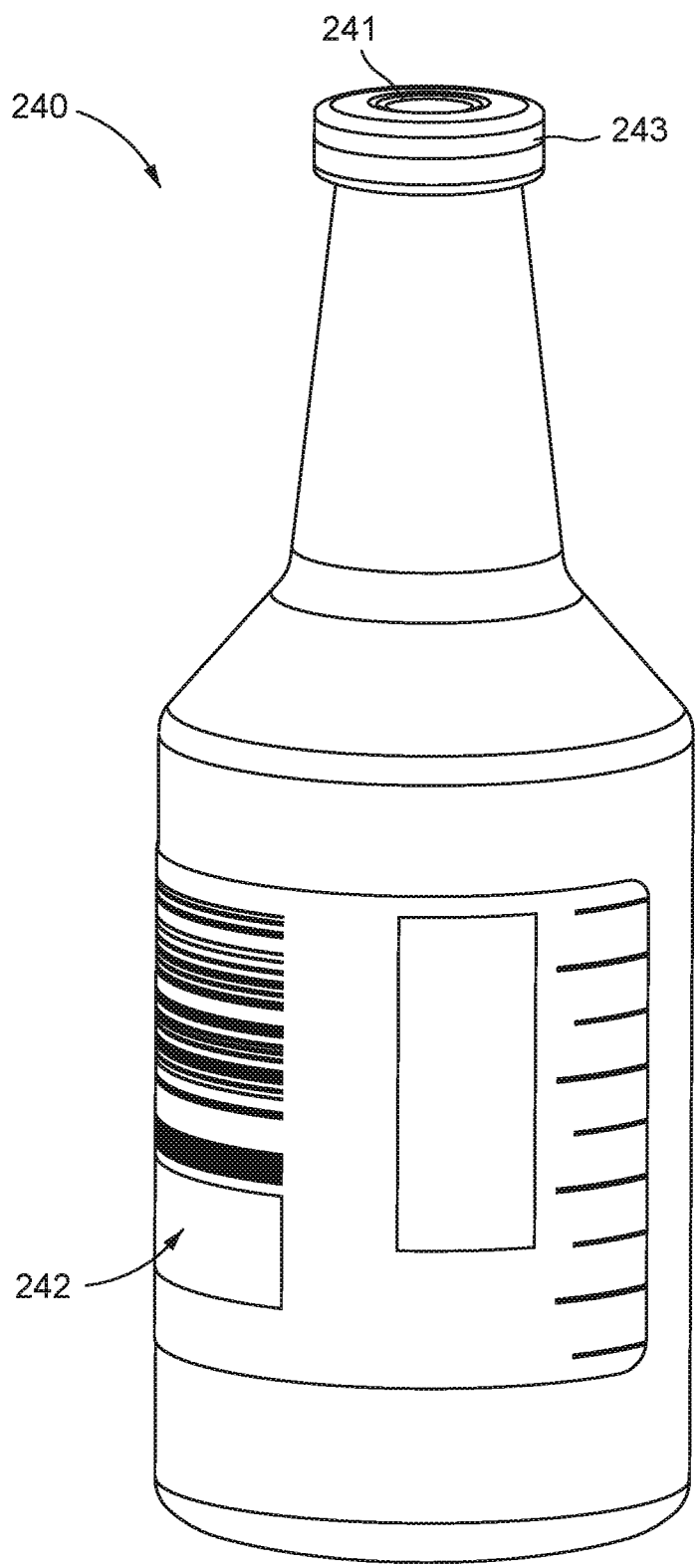
FIG. 2 is a perspective view of a sample reservoir according to an embodiment.

Referring to FIG. 2, a fluid reservoir 240 or sample container is illustrated according to an embodiment. In some instances, the fluid reservoir 240 can be used and/or included in, for example, the collection device 100 described above. Thus, while not shown in FIG. 2, the fluid reservoir 240 can be coupled to and/or can include a sterilization member 240 configured, for example, to maintain a sterility of a portion of the fluid reservoir 240 (e.g., a proximal surface) prior to use. Moreover, the fluid reservoir 240 can be positioned within and/or can engage a transfer adapter (e.g., such as the transfer adapter 120) and can be moved relative thereto to 1) automatically disengage at least a portion of the sterilization member, for example, from the proximal surface and 2) place the fluid reservoir 240 in fluid communication with the transfer adapter, as described in further detail herein with respect to specific embodiments.

The fluid reservoir 240 can be any suitable reservoir for containing a bodily-fluid, including, for example, a single use disposable collection reservoir, a vacuum based collection reservoir (e.g., maintaining negative pressure conditions that can produce a suction or vacuum force), a sample reservoir as described in the '420 patent, and/or the like. While shown as having a bottle shape or the like, the fluid reservoir 240 can be any suitable bottle, tube, vial, microvial, container, syringe, etc. In some embodiments, the reservoir 240 can be an aerobic culture bottle or an anaerobic culture bottles. That is to say, the fluid reservoir 240 can include an aerobic or anaerobic culture medium disposed within an inner volume defined by the fluid reservoir 240, as described in detail above with reference to the fluid reservoir 140. Moreover, the culture medium disposed therein can be associated with one or more tests, procedures, and/or actions configured to, for example, detect the presence of certain microbes that are known to thrive in that medium. In other embodiments, the fluid reservoir 240 can include common additives such as heparin, citrate, ethylenediaminetetraacetic acid (EDTA), oxalate, and/or the like that are used to preserve specific characteristics and/or qualities of a bodily-fluid sample (e.g., blood) prior to diagnostic analysis.

In the embodiment shown in FIG. 2, the fluid reservoir 240 includes a proximal surface 241, a proximal rim 243, and a label 242. The proximal surface 241 can include and/or can otherwise form a port, septum, frangible portion or the like, which can be transitioned from a substantially sealed configuration to a substantially unsealed configuration to place an inner volume of the fluid reservoir in fluid communication with a volume outside of the fluid reservoir 240, as described in detail above. In other words, the proximal surface 241 can be, for example, an inlet surface. The proximal rim 243 can be, for example, a flange, a rib, a rolled portion, and/or the like. Although not shown in FIG. 2, the proximal rim 243 of the fluid reservoir 240 can be removably coupled to a sterilization member such as those described herein. In some embodiments, such a sterilization member, for example, can be coupled to the proximal rim 243 during a manufacturing process or the like such that at least a portion of the proximal surface 241 is maintained in a substantially sterile environment prior to use, as described in further detail herein.

As shown in FIG. 2, the label 242 is disposed about a portion of the fluid reservoir 240. The label 242 can be and/or can include a tag or indicia associated with one or more characteristics of the fluid reservoir 240. For example, the label 242 can include a code portion such as, for example, a serial number, bar code, a quick response (QR) code, a radio-frequency identification (RFID) tag, a near field communication (NFC) tag, and/or the like. In this manner, the code portion can provide a user (e.g., a doctor, phlebotomist, nurse, technician, etc.) with information associated with the fluid reservoir 240 such as, for example, the type of culture medium or additive (as described above) disposed therein, the amount (e.g., volume, mass, density, etc.) of the culture medium or additive (as described above) disposed therein, a volume of bodily-fluid that the fluid reservoir 240 should receive, a tolerance value, the type of tests to be performed on the bodily-fluid sample disposed therein, temperature, and/or the like. Thus, the user can determine, inter alia, the amount or the volume of bodily-fluid that he or she should transfer into the fluid reservoir 240.

In some embodiments, the label 242 can include a volumetric indicator portion or the like that can provide a visual indicator associated with the bodily-fluid disposed in the fluid reservoir 240. For example, the volumetric indicator portion can include a set of evenly spaced lines, tic marks, dashes, arrows, markers, and/or any other suitable gradation or indicia that can be associated with a specific volume of the fluid reservoir 240 if filled to that point. In some embodiments, the fluid reservoir 240 can be substantially transparent, allowing the user to visualize the sample disposed therein. For example, a user can visually assess the volume of the bodily-fluid disposed in the fluid reservoir 240 by determining at what point along the indicator portion the meniscus of the bodily-fluid aligns. In some embodiments, a device can be coupled to the fluid reservoir 240 that is configured to verify and/or otherwise indicate a volume of bodily-fluid transferred into the fluid reservoir such as, for example, those described in U.S. patent application Ser. No. 15/146,967 entitled, "Devices and Methods for Verifying a Sample Volume," filed May 5, 2016, the disclosure of which is incorporated herein by reference in its entirety. In some such embodiments, verifying and/or otherwise indicating a volume of bodily-fluid transferred into the fluid reservoir (e.g., the fluid reservoir 240) can facilitate the transfer of a desired and/or predetermined volume of the bodily-fluid into the fluid reservoir, which in turn, can limit false test results otherwise associated with an undesirable volume of the bodily-fluid (e.g., too much bodily-fluid or too little bodily-fluid for a given test or tests).

Although the fluid reservoir 240 is specifically described above, in other embodiments, the fluid reservoir 240 can be any suitable shape, size, and/or configuration. For example, while the fluid reservoir 240 is shown and described as including the label 242 configured to provide a user with information associated with the fluid reservoir 240, in other embodiments, a fluid reservoir without a label and/or other identifying portion can be used.

Figure 3:
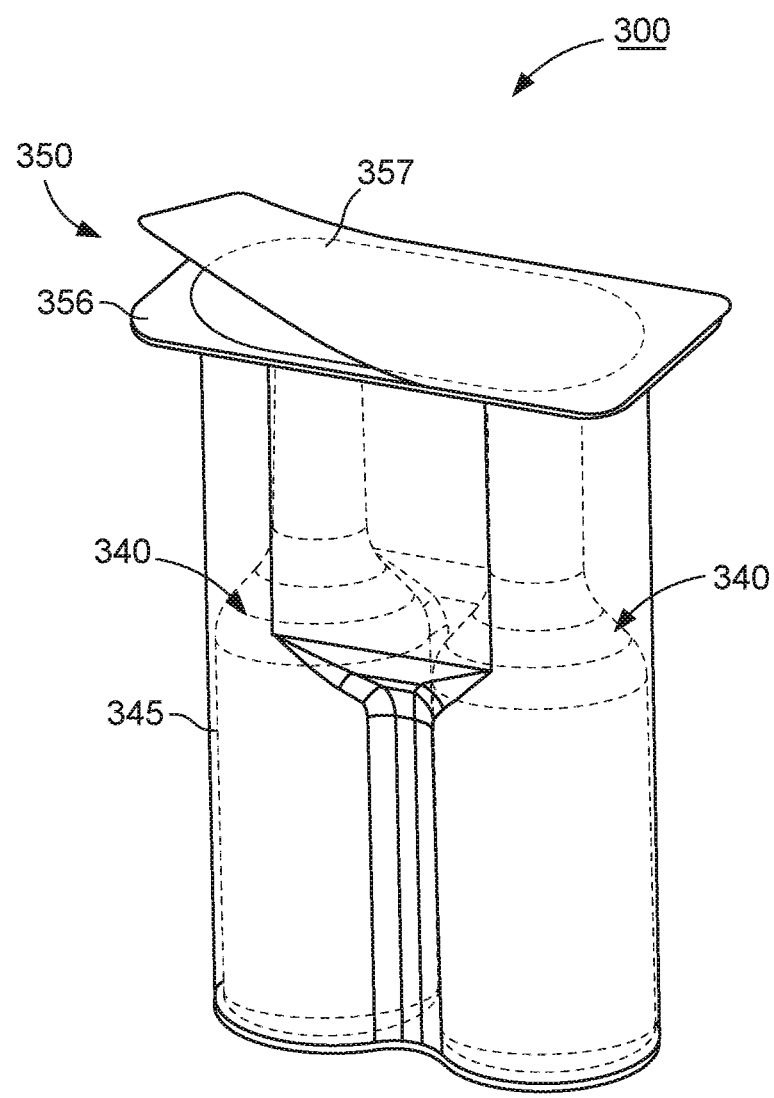
FIG. 3 is a perspective view of a portion of a bodily-fluid collection device according to an embodiment.
Figure 4:
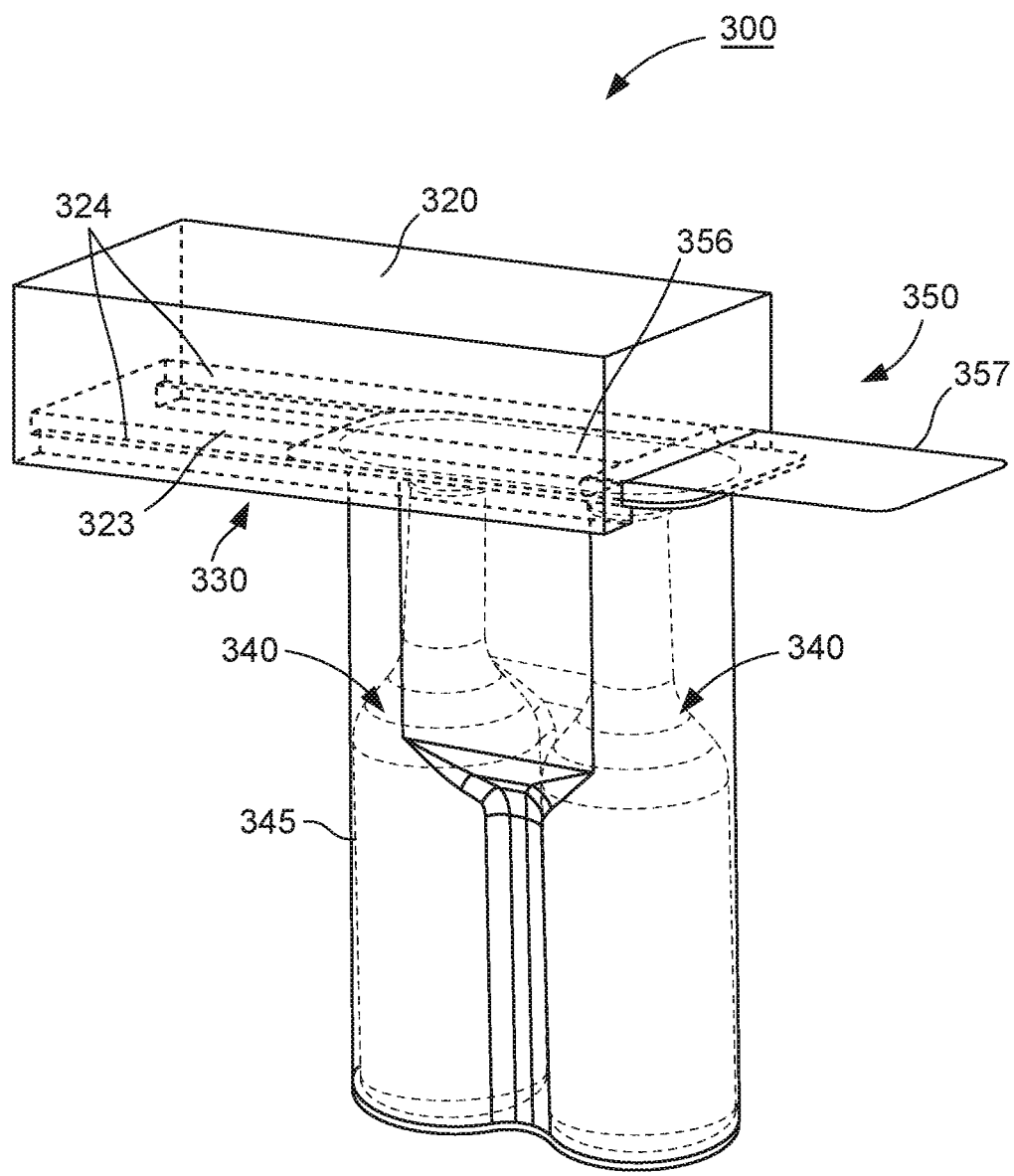
FIG. 4 is a perspective view of a sterilization and/or disinfection member, a sample reservoir, and a transfer adapter included in the bodily-fluid collection device of FIG. 3.

As described above, in some embodiments, the fluid reservoir 240 can be coupled to and/or can include a sterilization member that can be at least partially disengaged from the fluid reservoir 240 when the fluid reservoir 240 is positioned within a transfer adapter or device. For example, FIGS. 3 and 4 illustrate at least a portion of a collection device 300 according to an embodiment. The collection device 300 (or portion thereof) includes a transfer adapter 320 configured to receive a portion of at least one fluid reservoir 340 and at least one sterilization member 350. More specifically, at least a portion of the one or more fluid reservoirs 340 can be inserted into the transfer adapter 320, which can be operable to transition the at least one sterilization members 350 from a first configuration, in which the one or more sterilization members 350 substantially maintain the sterility of a portion of the one or more fluid reservoirs 340, to a second configuration in which the one or more sterilization members 350 are at least partially disengaged from the one or more fluid reservoirs 340 to allow the fluid reservoirs 340 to be placed in fluid communication with the transfer adapter 320, as described in further detail herein.

The collection device 300 (or portion thereof) as shown in FIG. 3, includes a reservoir housing 345 that contains, houses, and/or otherwise receives two fluid reservoirs 340 (e.g., a first fluid reservoir 340 and a second fluid reservoir 340). In other embodiments, any number of fluid reservoirs 340 can be contained within the housing 345. The fluid reservoirs 340 can be any suitable shape, size, and/or configuration. For example, in some embodiments, the fluid reservoirs 340 are substantially similar to and/or the same as the fluid reservoir 240 described above with reference to FIG. 2. Thus, the fluid reservoirs 340 are not described in further detail herein.

The housing 345 can be any suitable shape, size, and/or configuration. For example, in some embodiments, the housing 345 can have a size and/or shape that is associated with a size and/or shape of the fluid reservoir to be disposed therein. More particularly, the housing 345 defines an inner volume that is sufficient to receive at least the first and second fluid reservoir 340. As shown in FIG. 3, the housing 345 is coupled to the sterilization member 350, which is configured to at least temporarily fluidically isolate the inner volume of the housing 345 from a volume outside of the housing 345. For example, the housing 345 can be an enclosure that defines one or more openings defined by a sidewall or the like through which the fluid reservoirs 340 are inserted to be disposed within the inner volume. As shown, the sterilization member 350 is coupled to the sidewall defining the opening to at least temporarily seal the inner volume of the housing 345. For example, the sterilization member 350 can be coupled to and/or in contact with a surface of the sidewall such that the surface of the sidewall and the sterilization member 350 collectively define a fluid tight seal. In some embodiments, for example, the sterilization member 350 can be coupled to the surface via an adhesive, a standard medical sealing process using, for example, Tyvek, ultrasonic weld, or the like. In this manner, the inner volume of the housing 345 is substantially fluidically isolated from a volume outside of the housing 345.

In some embodiments, the fluid reservoirs 340 can be disposed in the housing 345 and the sterilization member 350 can be coupled to the housing 345 during manufacturing. In such embodiments, for example, the housing 345 can be substantially sterilized using standard medical sterilization practices (e.g. ethylene oxide, gamma radiation, e-beam, and/or the like) to facilitate maintenance of a sterile environment. Similarly, the fluid reservoirs 340 can be substantially sterilized and disposed in the inner volume of the housing 345 while the housing 345 and the fluid reservoirs 340 are in the sterile environment. Likewise, the sterilization member 350 can be substantially sterilized and coupled to the housing 345, after the fluid reservoirs 340 have been disposed therein, while the housing 345, the fluid reservoirs 340, and the sterilization member 350 are disposed in the sterile environment. Thus, while the sterilization member 350 is coupled to the housing 345 and in an unused configuration, the inner volume of the housing 345 (containing the fluid reservoirs 340) is a substantially sterile volume and/or environment. For example, in some embodiments, housing 345, fluid reservoirs 340, sterilization member 350 can be assembled (as described above) in a sterile environment such as ethylene oxide gas or the like. Moreover, by sealing the housing 345 with the sterilization member 350, the fluid reservoirs 340 within the inner volume of the housing 345 are maintained in, for example, an ethylene oxide gas environment until the housing 345 is unsealed.

The sterilization member 350 can be any shape, size, and/or configuration suitable for coupling to the housing 345. For example, the sterilization member 350 can be one or more films, foils, sheets, membranes, diaphragms, and/or the like. More particularly, the sterilization member 350 can include a first portion 356 that is removably coupled to a second portion 357. The first portion 356 can be, for example, a base configured to be coupled to the housing 345. As such, the first portion 356 can be formed from a relatively stiff material that can provide structural integrity for the sterilization member 350 to be coupled to the housing 345. The second portion 357 can be removably coupled to the first portion 356 and can be formed from a relatively flexible material to allow the second portion 357 to deform, bend, fold, peel, and/or otherwise at least partially disengage from the first portion 356. Furthermore, a surface of the sterilization member 350 (e.g., of the first portion 356) in contact with the surface of the housing 345 can have and/or can define an area that is greater than an area defined by the surface of the housing 345. In other words, the sterilization member 350 can form a flange or the like that extends beyond a perimeter of the housing 345, as shown in FIG. 3 and as described in further detail herein.

Prior to use, the arrangement of the sterilization member 350 is such that the second portion 357 is coupled to the first portion 356 to form a substantially fluid tight seal and/or interface. In some embodiments, for example, a perimeter of the second portion 357 (or an area near a perimeter) can be coupled to an associated perimeter of the first portion 356 via an adhesive or ultrasonic weld. In other embodiments, substantially the entirety of a surface of the second portion 357 can be adhered to substantially the entirety of a surface of the first portion 356. In still other embodiments, the second portion 357 can be coupled to the first portion 356 in any suitable manner. Moreover, the second portion 357 is coupled to the first portion 356 in such a manner that the first portion 356 and the second portion 357 collectively form a substantially sterile area. For example, in some embodiments, a substantially sterile area can be circumscribed by a seal defined by the coupling of the second portion 357 to the first portion 356. In some embodiments, the second portion 357 can be coupled to the first portion 356 via an adhesive, which in turn, is impregnated with and/or otherwise includes a sterilizing agent such as those described above. Thus, the sterility of an area of the first portion 356 of the sterilization member 350 aligned with and/or covering, for example, the opening of the housing 345 is maintained prior to use.

The transfer adapter 320 can be any suitable transfer adapter. For example, in some embodiments, the transfer adapter 320 can be substantially similar to the transfer adapter 120 described above with reference to FIG. 1. Thus, aspects of the transfer adapter 320 are not described in further detail herein. As shown in FIG. 4, the transfer adapter 320 includes an inner surface 323 that defines an inner volume 330 configured to receive a portion of the housing 345 and at least a portion of the sterilization member 350. Although not shown in FIG. 4, the transfer adapter 320 can include a puncture member, a port, a transfer member, and/or the like configured to establish fluid communication between the transfer adapter 320 and the fluid reservoirs 340.

The inner surface 323 defines a set of channels 324 configured to engage a portion of the sterilization member 350 as the housing 345 is inserted into the inner volume 330. More particularly, the channels 324 can slidably receive a portion of the sterilization member 350 that extends beyond the perimeter of the housing 345 (as described above) and can define a substantially linear range of motion of the housing 345 and the sterilization member 350 relative to the transfer adapter 320. In addition, the arrangement of the channels 324 can be such that as the sterilization member 350 is inserted into the channels 324 and the housing 345 is moved relative to the transfer adapter 320, a portion of the inner surface of the transfer adapter 320 defining the channels 324 peels, removes, decouples, and/or otherwise disengages the second portion 357 of the sterilization member 350 from the first portion 356 of the sterilization member 350, thereby exposing a surface of the first portion 356 that is aligned with and/or otherwise covers at least a portion of the opening defined by the housing 345.

For example, in use, a user can place the transfer adapter 320 in fluid communication with a lumen-defining device, transfer device, collection device, diversion device, and/or the like, which in turn, is in fluid communication with a portion of the body of a patient or an intermediary device containing a bodily-fluid, as described in detail above with reference to the transfer adapter 120. Moreover, the housing 345, the fluid reservoirs 340, and the sterilization member 350 can be in a first configuration in which the sterilization member 350 seals the inner volume of the housing 345 such that the fluid reservoirs 340 disposed therein are maintained in a substantially sterile environment. The user can manipulate the transfer adapter 320 and/or the housing 345 to insert the portion of the sterilization member 350 into the channels 324. As the user inserts the portion of the sterilization member 350 into the channels 324, the portion of the inner surface 323 that defines the channels 323 is placed in contact with the sterilization member 350. As the housing 345 is moved relative to the transfer adapter 320, the portion of the inner surface 323 disengages, peels, and/or otherwise decouples the second portion 357 of the sterilization member 350 from the first portion 356 of the sterilization member 350. As such, the substantially sterile surface of the first portion 356 that is aligned with and/or otherwise covers at least a portion of the opening defined by the housing 345 is exposed.

Once the user places the housing 345—and thus, the fluid reservoirs 340 disposed therein—in a desired position relative to the transfer adapter 320, the user can manipulate the collection device 300 (or portion thereof) to place the transfer adapter 320 in fluid communication with at least one of the fluid reservoirs 340. For example, in some embodiments, the user can actuate an actuator configured to advance a puncture member or the like through a surface of the fluid reservoir 340, thereby placing at least one of the fluid reservoirs 340 in fluid communication with the patient. Thus, at least one of the fluid reservoirs 340 can receive a flow of bodily-fluid from the patient or an intermediary device containing a bodily-fluid.

The arrangement of the collection device 300 (or portion thereof) is such that the sterility of the fluid reservoirs 340 within the housing 345 and the surface of the first portion 356 of the sterilization member 350 is maintained until a time relatively shortly before the transfer adapter 320 is placed in fluid communication with the fluid reservoirs 340. Similarly, although not shown in FIGS. 3 and 4, the transfer adapter 320 can include and/or can be coupled to any suitable sterilization member or mechanism that can be configured to maintain the sterility of, for example, a puncture member or other transfer means until a time relatively shortly before the transfer adapter 320 is placed in fluid communication with the fluid reservoirs 340. Thus, by maintaining the sterility of a fluidic interface between the transfer adapter 320 and the fluid reservoirs 340 until a relatively short time before placing the transfer adapter 320 in fluid communication with the fluid reservoirs, the probability of external contaminants being transferred into the bodily-fluid sample received by the fluid reservoirs 340 can be reduced. Moreover, pre-sterilizing fluidic interfaces and automatically exposing those fluidic interfaces just before establishing fluid communication between the transfer adapter 320 and the fluid reservoir 340 can increase compliance with sterilization protocols and ease of performing the procedure, as well as reduce costs and inadvertent mistakes.

Figure 5:
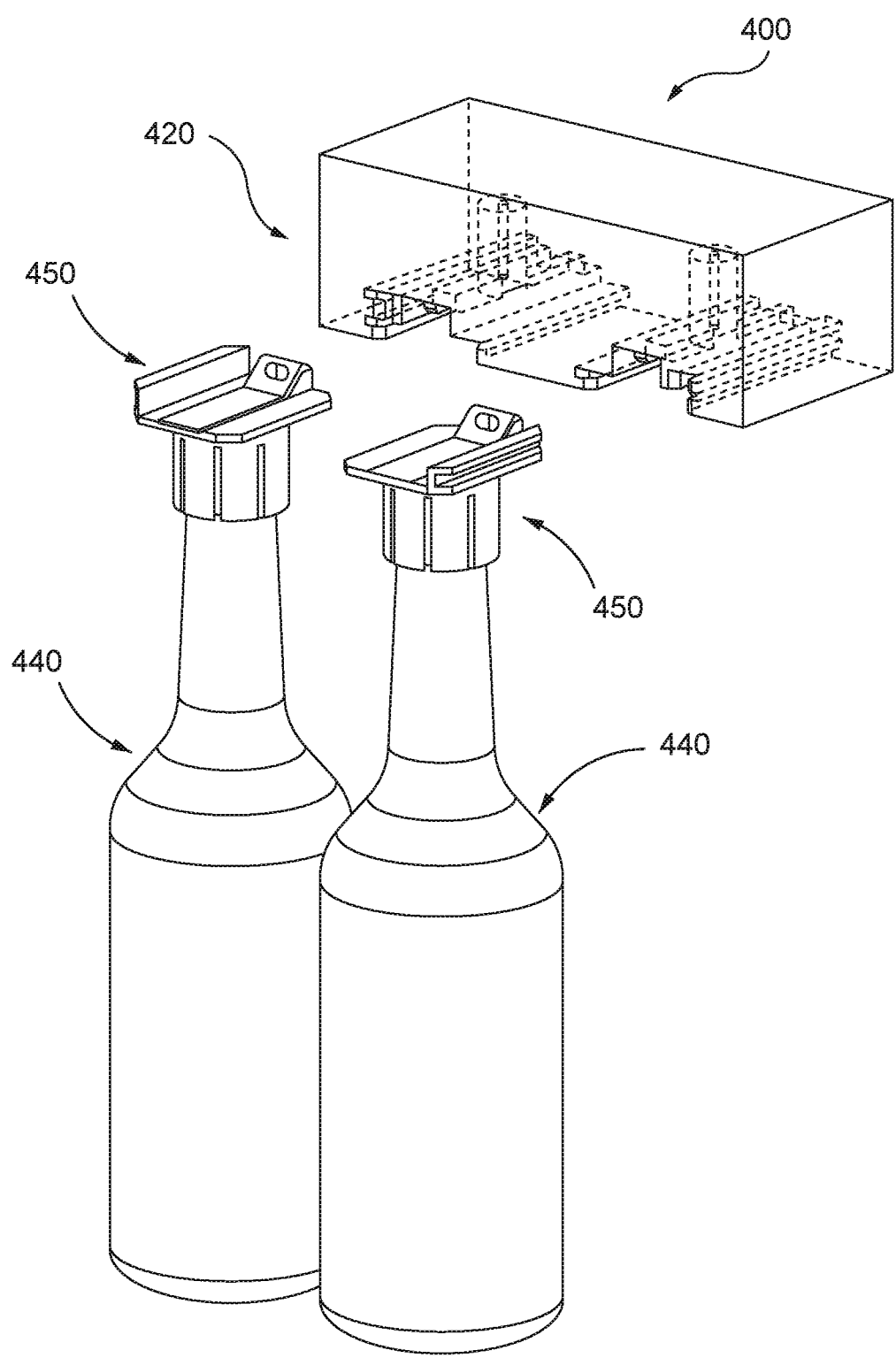
FIG. 5 is a perspective view of a portion of a bodily-fluid collection device in a first configuration, according to an embodiment.

Although the collection device 300 is shown and described above as including the housing 345 within which the fluid reservoirs 340 are disposed and to which the sterilization member 350 is coupled, in other embodiments, fluid reservoirs need not be disposed within a housing and can be coupled directly to a sterilization member. For example, FIGS. 5-10 illustrate at least a portion of a collection device 400 according to another embodiment. As shown in FIG. 5, the collection device 400 includes a transfer adapter 420, at least one fluid reservoir 440, and at least one sterilization member 450.

Some aspects of the collection device 400 can be similar in form and function to associated aspects of the collection devices 100, 200, and/or 300 (and/or components thereof) described above. For example, the embodiment shown in FIGS. 5-10 illustrates two fluid reservoirs 440, each of which can be similar to or substantially the same as the fluid reservoir 240 described above with reference to FIG. 2. Thus, aspects of the collection device 400 similar in form and function to associated and/or corresponding aspects of the collection devices, and/or components thereof, described above are not described in further detail herein. Moreover, while the collection device 400 is shown in FIG. 5 as including the two fluid reservoirs 440 and two sterilization members 450, in other embodiments, the collection device 400 can include a transfer adapter configured to receive one fluid reservoir and one sterilization member. In still other embodiments, the collection device 400 can include a transfer adapter configured to receive more than two fluid reservoirs and more than two sterilization members. In addition, in the embodiment shown in FIGS. 5-10, the two fluid reservoirs 440 can be substantially the same unless otherwise indicated and the two sterilization members 450 can be substantially the same unless otherwise indicated. Thus, a discussion of a single fluid reservoir (e.g., the fluid reservoir 440) and a single sterilization member (e.g., the sterilization member 450) can similarly apply to any number of fluid reservoirs and any number of sterilization members, respectively, included in the collection device 400.

Figure 6:
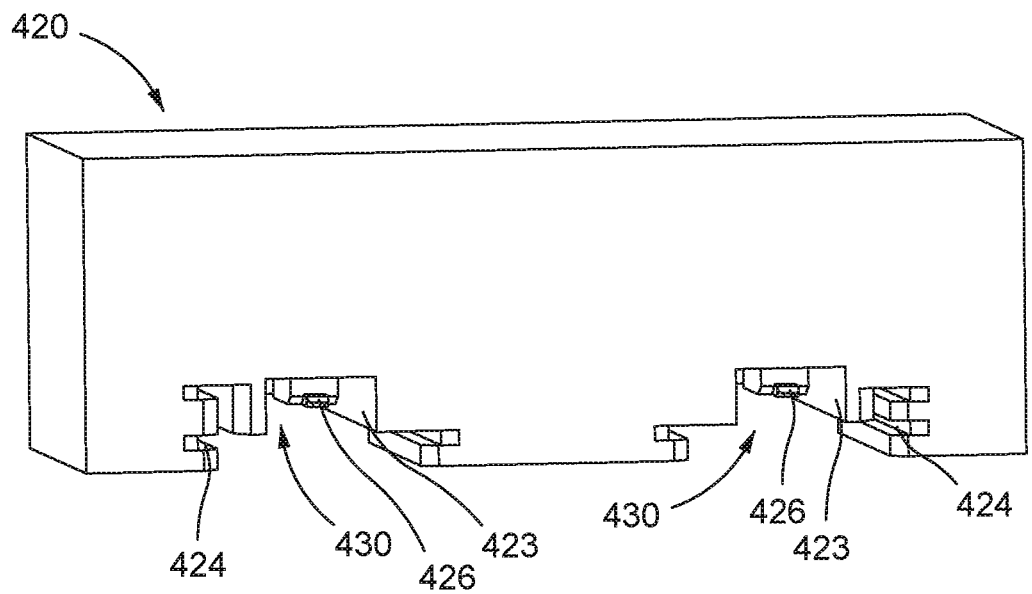
FIG. 6 is a perspective view of at least a portion of a transfer adapter included in the portion of the bodily-fluid collection device of FIG. 5.

The transfer adapter 420 of the collection device 400 can be any suitable transfer adapter. For example, in some embodiments, the transfer adapter 420 can be substantially similar to the transfer adapter 120 described above with reference to FIG. 1. Thus, aspects of the transfer adapter 420 are not described in further detail herein. As shown in FIGS. 5 and 6, the transfer adapter 420 includes an inner surface 423 that defines an inner volume 430 configured to receive a portion of the fluid reservoir 440 and at least a portion of the sterilization member 450. Although not shown in FIGS. 5 and 6, the transfer adapter 420 can include a puncture member, a port, a transfer member, and/or the like configured to establish fluid communication between the transfer adapter 420 and the fluid reservoirs 440.

The inner surface 423 defines a set of channels 424 configured to engage a portion of the sterilization member 450 as the fluid reservoir 440 is inserted into the inner volume 430. For example, the channels 424 can slidably receive a portion of the sterilization member 450 to guide the sterilization member 450 and/or the fluid reservoir 440 to which it is coupled as the fluid reservoir 440 is moved relative to the transfer adapter 420, as described in further detail herein. In addition, the transfer adapter 420 and/or the inner surface 423 thereof includes an engagement portion 426 configured to engage a seal 457 or the like of the sterilization member 450 as the sterilization member 450 is moved relative to the transfer adapter 420 (e.g., as the portion of the sterilization member 450 is moved within the channels 424 as a result of the fluid reservoir 440 being moved relative to the transfer adapter 420). For example, the engagement portion 426 can extend from the inner surface 423 and can include a protrusion, tab, flange, etc. configured to be placed in contact with a portion of the seal 457 of the sterilization member 450. Moreover, the engagement portion 426 is operable in transitioning the sterilization member 450 from a first configuration to a second configuration, as described in further detail herein.

The sterilization member 450 of the collection device 400 can be any suitable sterilization member and/or mechanism. In the embodiment shown in FIGS. 5-10, for example, the sterilization member 450 is a cap or the like coupled to a portion of the fluid reservoir 440. More particularly, the sterilization member 450 defines an inner volume 451 within which a portion of the fluid reservoir 440 is disposed. In some embodiments, for example, the sterilization member 450 can be coupled to the fluid reservoir 440 during a manufacturing process (e.g., as described above with reference to the fluid reservoirs 340 and sterilization member 350). In other embodiments, the sterilization member 450 can be coupled to the fluid reservoir 440 prior to use (e.g., by a user). Moreover, when the sterilization member 450 is coupled to the fluid reservoir 440, the sterilization member 450 is configured to maintain a fluidic interface of the fluid reservoir 440 (e.g., a surface, port, etc.) in a substantially sterile environment prior to use, as described in further detail herein. For example, in some embodiments, the sterilization member 450 can include and/or can be coupled to a pad, a swab, a sponge or porous material, and/or the like that can include a disinfecting agent such as those described herein. In some embodiments, at least a surface of the sterilization member 450 can be impregnated with a disinfecting agent such as, those described above. In some embodiments, the sterilization members 450 can include and/or can define a portion that is substantially porous, for example, to act as a substrate for the disinfection agent. In this manner, the sterilization member 450 can be disposed about a portion of the fluid reservoir 440 to maintain the sterility of the portion of the fluid reservoir 440 prior to use.

Figure 7:
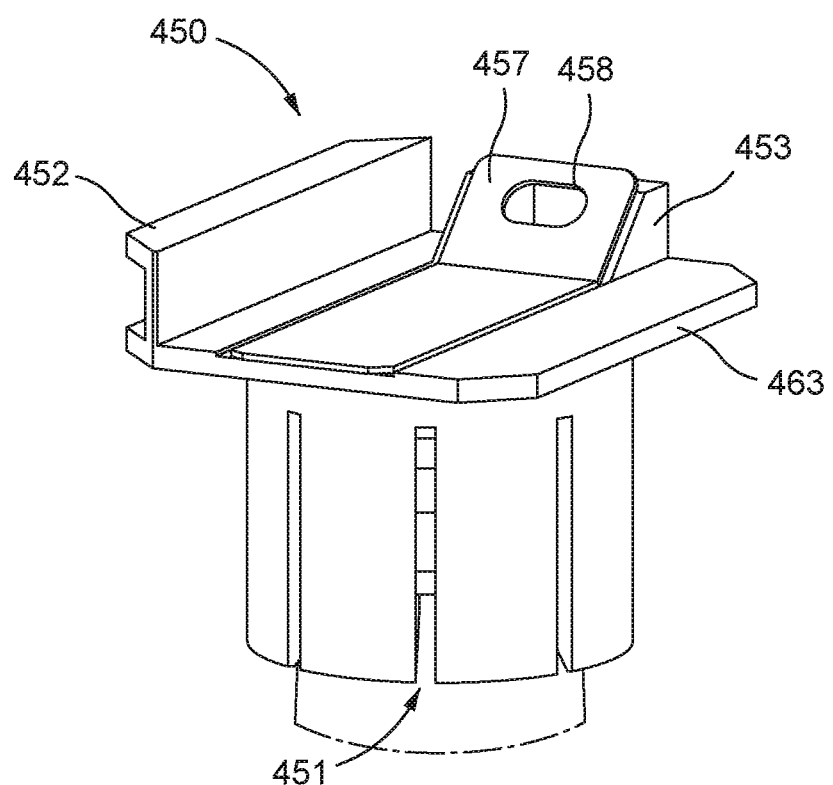
FIG. 7 is a perspective view of a sterilization and/or disinfection member included in the portion of the bodily-fluid collection device of FIG. 5.

As shown in FIG. 7, the sterilization member 450 includes a flange 463 having a guide portion 452 and a ramp portion 453. The flange 463 extends from the sterilization member 450 such that at least a portion of the flange 463 can be inserted in the channels 424 as the sterilization member 450 is moved within the inner volume 430. Moreover, a portion of the guide portion 452 can, for example, orient the sterilization member 450 relative to the transfer adapter 420 as the sterilization member 450 is inserted into the inner volume 430. For example, as shown in FIG. 7, the guide portion 452 can extend from the flange 463 and can include, for example, two protrusions, ribs, tabs, bends, etc. configured to be inserted into a portion of the channels 424 of the inner surface 423 having a similar configuration. In other words, the channels 424 defined by the inner surface 423 of the transfer adapter 420 are configured to receive an associated sterilization member 450 in a predetermined orientation and/or the like. In some embodiments, the arrangement of the guide portion 452 can be associated with a particular type of fluid reservoir. For example, in some embodiments, a sterilization member can include and/or can have a guide portion disposed on a first side and can be coupled to, for example, an aerobic culture bottle. Conversely, the sterilization member can include and/or can have a guide portion disposed on a second side, opposite the first side, and can be coupled to, for example, an anaerobic culture bottle. In other embodiments, a sterilization member need not be associated with predetermined type of fluid reservoir.

As described above, the sterilization member 450 includes the seal 457. In the embodiment shown in FIGS. 5-10, the seal 457 can be a sheet, foil, tape, and/or the like at least temporarily coupled to a surface of the flange 463 and configured to maintain at least a portion of the surface of the flange 463 in a substantially sterile configuration prior to use. Moreover, as shown, for example, in FIGS. 9-10, the sterilization member 450 can include and/or define an opening 455 or port, which is substantially covered, obstructed, or otherwise in contact with the seal 457. In other words, the seal 457 is at least temporarily coupled to a surface of the sterilization member 450 to at least temporarily fluidically isolate the opening 455 defined by the sterilization member 450, as described in further detail herein.

Figure 8:
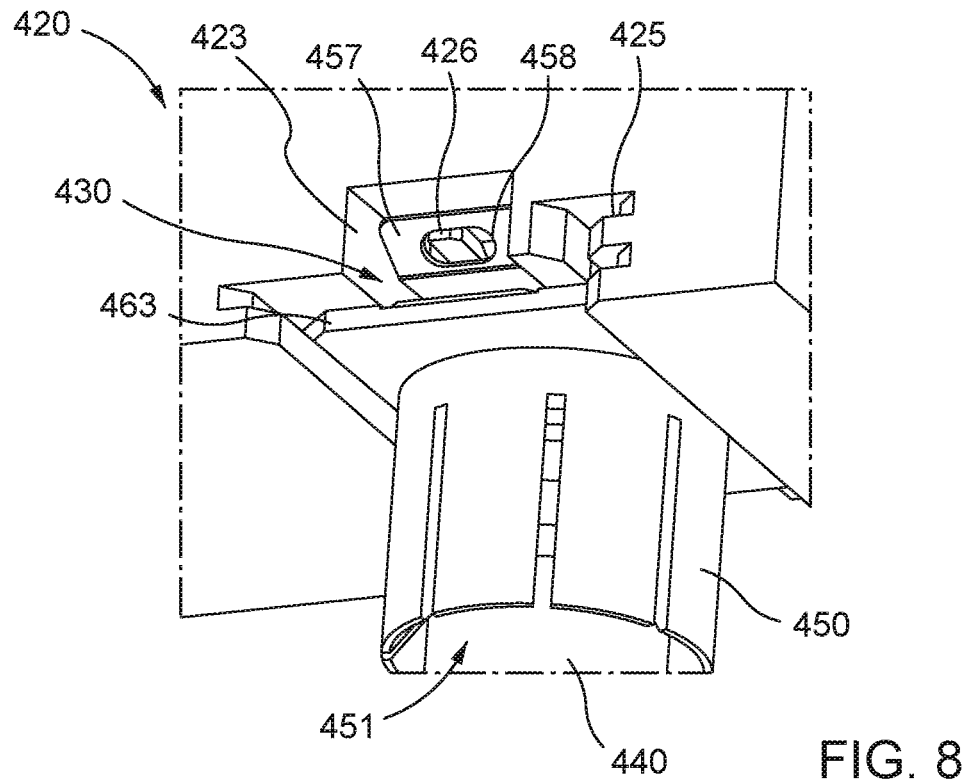
FIG. 8 is a perspective view of a portion of the bodily-fluid collection device of FIG. 5.
Figure 9:
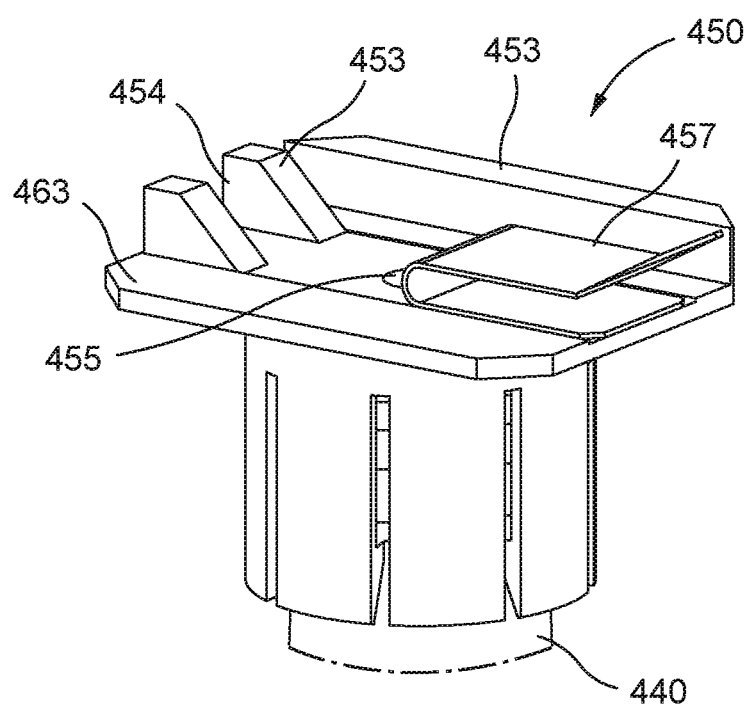
FIG. 9 is a perspective view of the sterilization and/or disinfection member of FIG. 7, in a second configuration.

As shown in FIGS. 7-9, a portion of the seal 457 defines an aperture and is disposed on the ramp portion 453 of the flange 463. The arrangement of the portion of the seal 457 and the ramp portion 453 is such that, as the sterilization member is moved within the inner volume 430, the portion of the seal 457 disposed on and/or otherwise in contact with the ramp portion 453 of the sterilization member 450 is placed in contact with the engagement portion 426 of the inner surface 423 of the transfer adapter 420. The engagement portion 426, therefore, is operable in transitioning the sterilization member 450 from the first configuration (see e.g., FIGS. 5-7) to the second configuration (see e.g., FIGS. 8-10), as described in further detail herein.

In use, a user can place the transfer adapter 420 in fluid communication with a lumen-defining device, transfer device, collection device, diversion device, and/or the like, which in turn, is in fluid communication with a portion of the body of a patient (or intermediary device containing a bodily-fluid, as described in detail above with reference to the transfer adapter 120. Moreover, the fluid reservoirs 440 and the sterilization member 450 can be in a first configuration in which the sterilization member 450 maintains the sterility of at least the portion of the fluid reservoir 440 (e.g., a fluidic interface such as a surface or port).

The user can manipulate the transfer adapter 420 and/or the fluid reservoir 440 to insert the portion of the sterilization member 450 into the channels 424, as described above with reference to the collection device 300. As the user inserts the portion of the sterilization member 450 into the channels 424, the engagement portion 426 of the inner surface 423 is placed in contact with the portion of the seal 457 of the sterilization member 450. More specifically, the ramp portion 453 of the sterilization member 450 defines a channel 454 or slot that exposes the portion of the seal 457 defining the aperture 458. As such, movement of the sterilization member 450 (and fluid reservoir 440) within the inner volume 430 disposes the engagement portion 426 (or a protrusion extending therefrom) in the aperture 458 defined by the portion of the seal 457, as shown in FIGS. 8 and 10.

Figure 10:
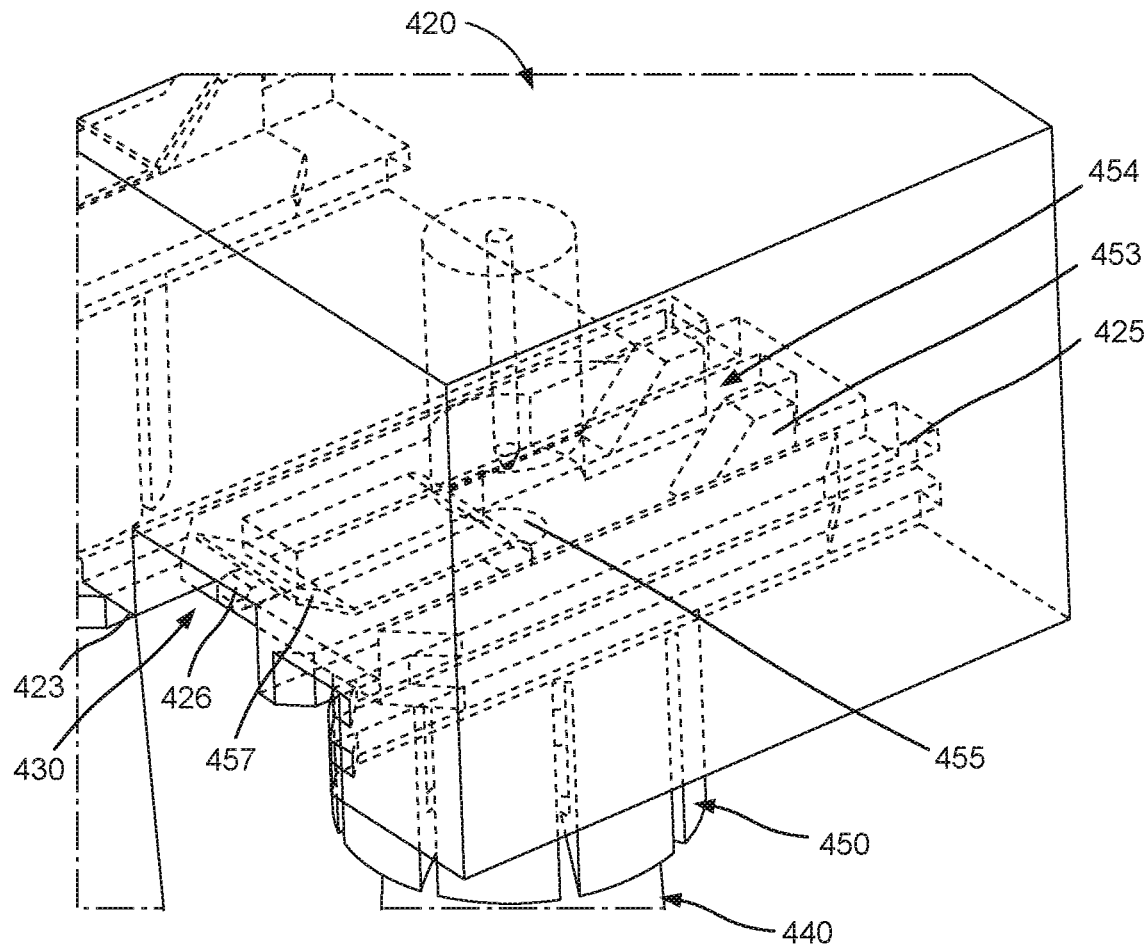
FIG. 10 is a perspective view of a portion of the bodily-fluid collection device of FIG. 5, in a second configuration.

With the engagement portion 426 disposed in the aperture 458, further movement of the sterilization member 450 advances the sterilization member 450 relative to the engagement portion 426 of the transfer adapter 420, which in turn, removes, disengages, peels, and/or otherwise decouples at least a portion of the seal 457 from the sterilization member 450, as shown in FIGS. 8-10. Expanding further, with the engagement portion 426 disposed in the aperture 458 of the seal 457, at least a portion of the seal 457 is maintained in a substantially fixed position relative to the transfer adapter 420 as the sterilization member 450 is moved within the inner volume 430. Thus, such an arrangement removes, disengages, peels, and/or otherwise decouples a portion of the seal 457 from the surface of the sterilization member 450. Moreover, as shown in FIGS. 9 and 10, when the sterilization member 450 is disposed in a desired position relative to the transfer adapter 420, the seal 457 is sufficiently removed from the surface of the sterilization member 450 such that the opening 455 or port is exposed.

Once the user places the sterilization member 450—and thus, the fluid reservoirs 440 coupled thereto—in the desired position relative to the transfer adapter 420, the user can manipulate the collection device 400 (or portion thereof) to place the transfer adapter 420 in fluid communication with at least one of the fluid reservoirs 440. For example, in some embodiments, the user can actuate an actuator configured to advance a puncture member or the like through the opening 455 of the sterilization member 450 and through a surface or port of the fluid reservoir 440, thereby placing at least one of the fluid reservoirs 440 in fluid communication with the patient or an intermediary device containing a bodily-fluid. While not shown, in other embodiments, coupling the collection device 400 to the fluid reservoirs 440 can automatically facilitate access such that bodily-fluid flow begins as soon as physical coupling is complete. Thus, the fluid reservoir 440 can receive a flow of bodily-fluid from the patient or intermediary device containing bodily-fluid.

As described above with reference to the collection device 300, the arrangement of the collection device 400 (or portion thereof) is such that the sterility of at least the portion of the fluid reservoir 440 in contact with the sterilization member 450 is maintained until a time relatively shortly before the transfer adapter 420 is placed in fluid communication with the fluid reservoir 440. Thus, by maintaining the sterility of a fluidic interface between the transfer adapter 420 and the fluid reservoir 440 until a relatively short time before placing the transfer adapter 420 in fluid communication with the fluid reservoirs 440, the probability of external contaminants being transferred into the bodily-fluid sample received by the fluid reservoir 440 can be reduced. Moreover, pre-sterilizing fluidic interfaces and automatically exposing those fluidic interfaces just before establishing fluid communication between the transfer adapter 420 and the fluid reservoir 440 can increase compliance with sterilization protocols and ease of performing the procedure, as well as reduce costs and inadvertent mistakes.

Figure 11:
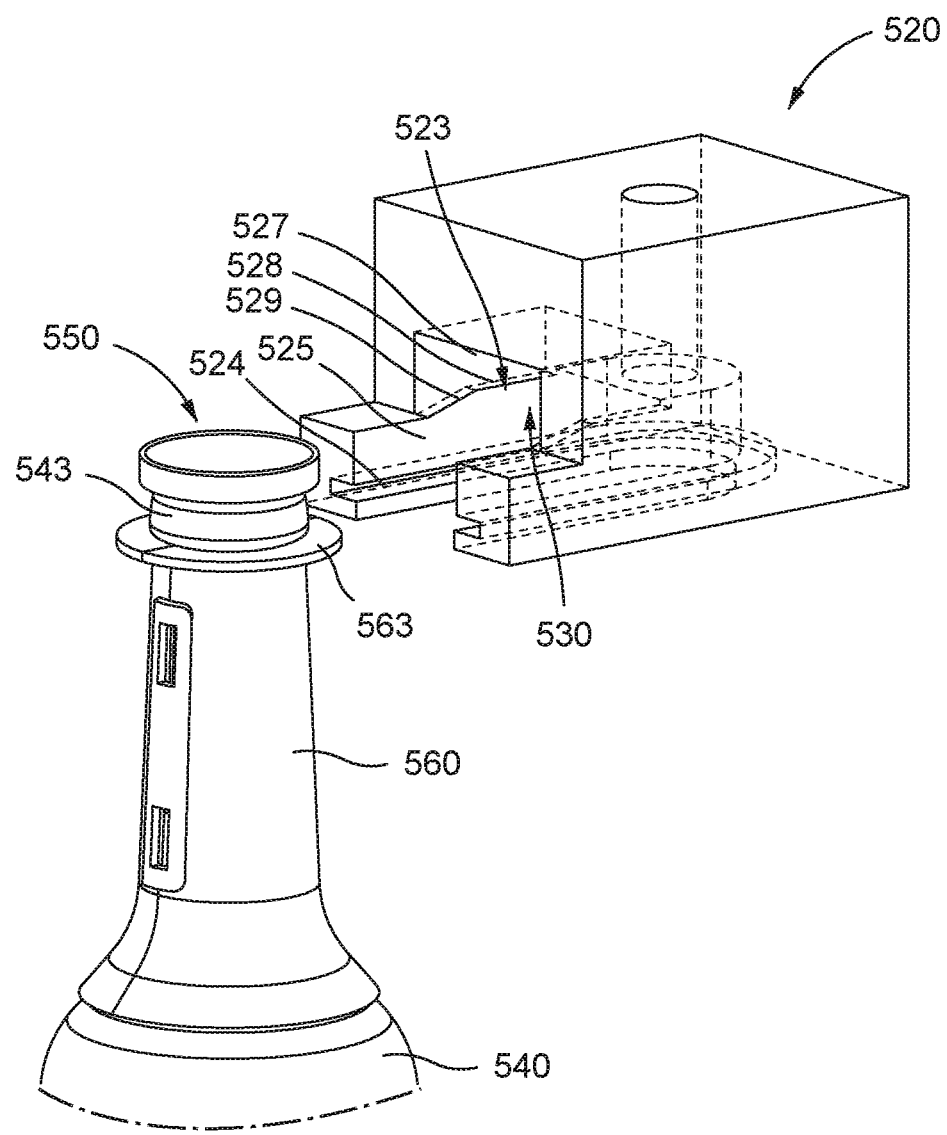
FIG. 11 is a perspective view of a portion of a bodily-fluid collection device in a first configuration, according to an embodiment.

Referring now to FIGS. 11-14, a collection device 500 is illustrated according to another embodiment. As shown in FIG. 11, the collection device 500 includes a transfer adapter 520, a fluid reservoir 540, and a sterilization member 550. Some aspects of the collection device 500 can be similar in form and function to associated aspects of the collection devices 100, 200, 300, and/or 400 (and/or components thereof) described above. For example, the embodiment shown in FIGS. 11-14 illustrates the fluid reservoir 540, which can be similar to or substantially the same as the fluid reservoir 240 described above with reference to FIG. 2. Thus, aspects of the collection device 500 similar in form and function to associated and/or corresponding aspects of the collection devices, and/or components thereof, described above are not described in further detail herein.

The transfer adapter 520 of the collection device 500 can be any suitable transfer adapter. For example, in some embodiments, the transfer adapter 520 can be substantially similar in form and/or function to the transfer adapters 120, 220, 320, and/or 420 described above. Thus, aspects of the transfer adapter 520 are not described in further detail herein. As shown in FIG. 11, the transfer adapter 520 includes an inner surface 523 that defines an inner volume 530 configured to receive a portion of the fluid reservoir 540 and the sterilization member 550. Although not shown in FIGS. 11-14, the transfer adapter 520 can include a puncture member, a port, a transfer member, and/or the like configured to establish fluid communication between the transfer adapter 520 and the fluid reservoirs 540. For example, in some embodiments, the transfer adapter 520 can include a puncture member such as a sheathed needle or the like that can pierce or puncture a surface 541 of the fluid reservoir 540 (see e.g., FIG. 14) to establish fluid communication between the transfer adapter 520 and the fluid reservoir 540.

The inner surface 523 includes a first portion 525 and a second portion 527. The first portion 525 defines a set of channels 524 configured to engage a portion of the sterilization member 550 as the fluid reservoir 540 is inserted into the inner volume 530, as described above with reference to the transfer adapter 320 and 420. For example, the channels 524 can slidably receive a portion of the sterilization member 550 to guide the sterilization member 550 and/or the fluid reservoir 540 to which it is coupled when the fluid reservoir 540 is moved relative to the transfer adapter 520, as described in further detail herein.

As shown, for example, in FIG. 11, the first portion 525 of the inner surface 523 has a width defined between opposite sides of the first portion 525 that is less than a width defined between opposite sides of the second portion 525. Moreover, the first portion 525 of the inner surface 523 has a depth that is greater than a depth of the second portion 527 of the inner surface 523. This arrangement of the inner surface 523 forms an edge surface 528 or corner that is associated with a difference between the width of the first portion 525 and the width of the second portion 527. The edge surface 528 extends along the depth of the second portion 527 and includes, for example, a ramp portion 529 or the like. As described in further detail herein, a portion of the sterilization member 550 is configured to be placed in contact with the edge surface 528 when the sterilization member 550 is inserted into the inner volume.

The sterilization member 550 of the collection device 500 can be any suitable sterilization member and/or mechanism. In the embodiment shown in FIGS. 11-14, for example, the sterilization member 550 is a cap or the like coupled to a portion of the fluid reservoir 540. For example, the sterilization member 550 can be formed from a relatively flexible material and can be coupled to a proximal rim 543 of the fluid reservoir 540 via a friction fit, press fit, threaded coupling, and/or the like. As described above, the sterilization member 550 is configured to be coupled to the fluid reservoir 540 to obstruct and/or fluidically isolate the surface 541 of the fluid reservoir 540. For example, in some embodiments, the sterilization member 550 can be coupled to the fluid reservoir 540 during a manufacturing process (e.g., as described above with reference to the fluid reservoirs 340 and sterilization member 350). In other embodiments, the sterilization member 550 can be coupled to the fluid reservoir 540 prior to use (e.g., by a user). Moreover, when the sterilization member 550 is coupled to the fluid reservoir 540, the sterilization member 550 is configured to maintain the surface 541 (e.g., a fluidic interface, port, etc.) of the fluid reservoir 540 in a substantially sterile environment prior to use, as described in detail above.

Figure 12:
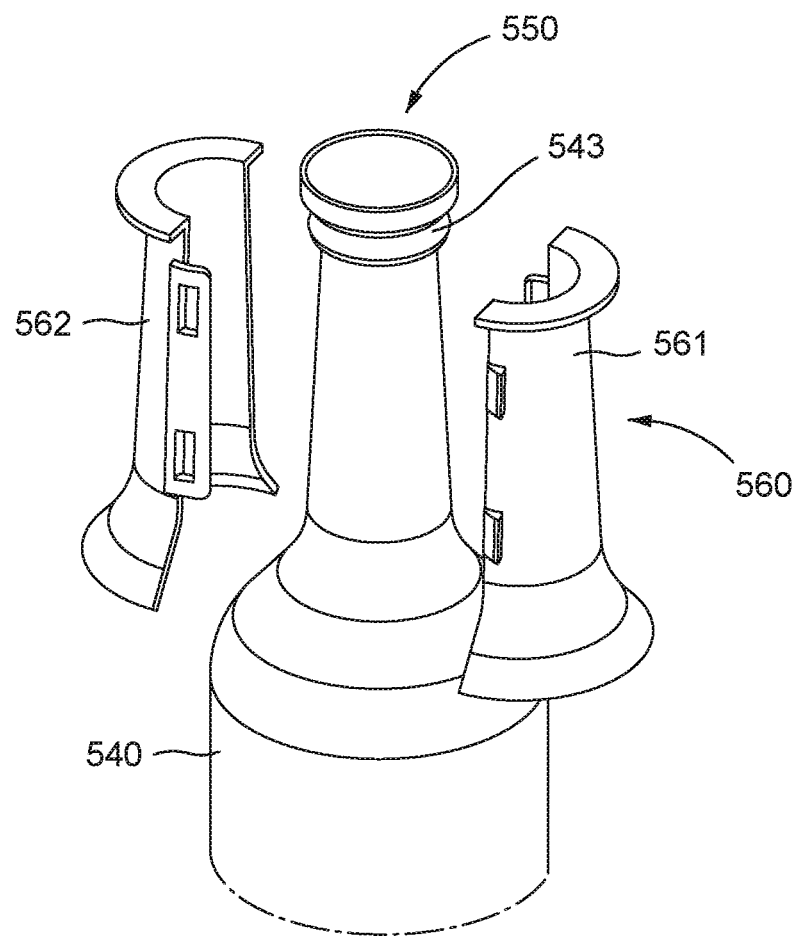
FIG. 12 is a partially exploded view of a sterilization and/or disinfection member and a sample reservoir included in the bodily-fluid collection device of FIG. 11.

As shown in FIGS. 11 and 12, the sterilization member 550 includes a collar 560 or the like having a first portion 561 and a second portion 562. The first portion 561 and the second portion 562 of the collar 560 can be positioned about a portion of the fluid reservoir 560 and coupled (e.g., via a snap fit, interference fit, etc.) to couple the collar 560 to the fluid reservoir 540. Moreover, as shown in FIGS. 11-14, the collar 560 forms a flange 563 or the like configured to be inserted into the channels 524 of the transfer adapter 520 as the sterilization member 550 is moved within the inner volume 530, as described in detail above. In this manner, the flange 563 can, for example, orient and/or direct the sterilization member 550 relative to the transfer adapter 520 as the sterilization member 550 is inserted into the inner volume 530.

Figure 13:
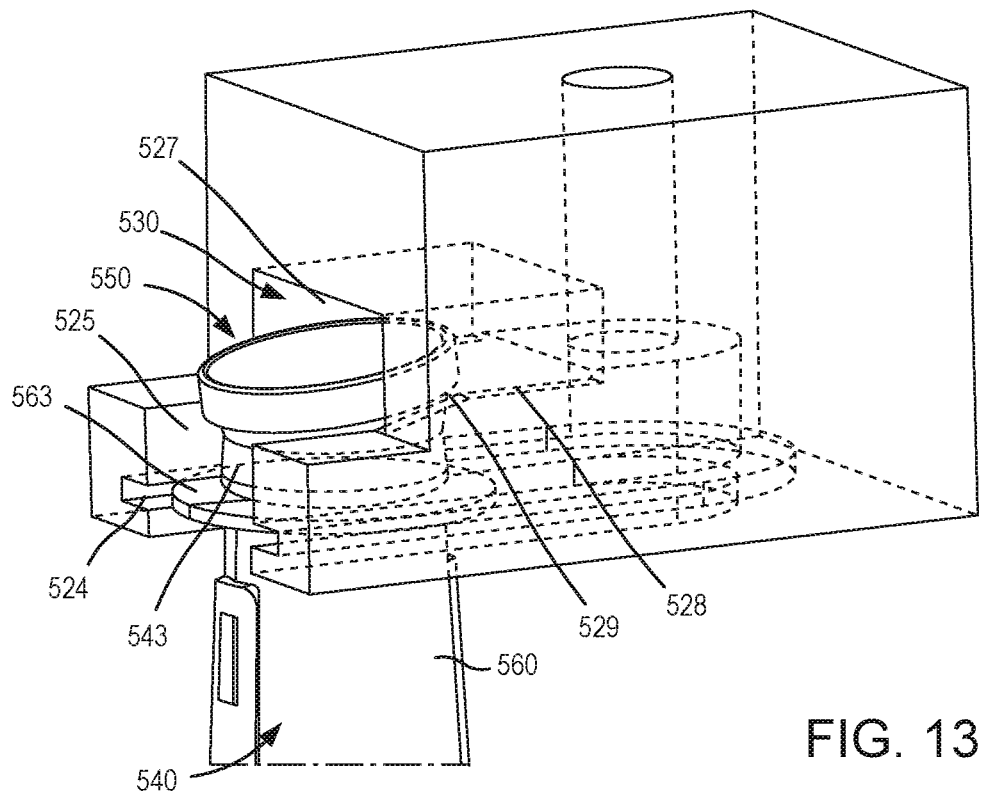
FIGS. 13 and 14 are perspective views of the bodily-fluid collection device of FIG. 11 as the bodily-fluid collection device is transitioned from a first configuration to a second configuration.

In use, a user can place the transfer adapter 520 in fluid communication with a lumen-defining device, transfer device, collection device, diversion device, and/or the like, which in turn, is in fluid communication with a portion of the body of a patient (or intermediary device containing a bodily-fluid, as described in detail above with reference to the transfer adapter 120. Moreover, the fluid reservoir 540 and the sterilization member 550 can be in a first configuration in which the sterilization member 550 obstructs, covers, and/or otherwise fluidically isolates the surface 541 of the fluid reservoir to substantially maintain the sterility of the surface 541. The user can manipulate the transfer adapter 520 and/or the fluid reservoir 540 to insert the flange 563 of the collar 560 into the channels 524, as described above, for example, with reference to the collection device 300. As the user inserts the portion of the sterilization member 550 into the inner volume 530 of the transfer adapter 520, sterilization member 550 is placed in contact with the edge surface 528, as shown in FIG. 13. In some embodiments, coupling the collar 560 about the fluid reservoir 540 and disposing the flange 563 in the channels 524 places the sterilization member 550 in a predetermined position (e.g., height) relative to the transfer adapter 520. For example, the predetermined position can be a position in which the sterilization member 550 is placed in contact with the edge surface 528. Thus, as the sterilization member 550 is advanced relative to the transfer adapter 520, the sterilization member 550 is placed in contact with the ramp portion 529 of the edge surface 528, as shown in FIG. 13.

Figure 14:
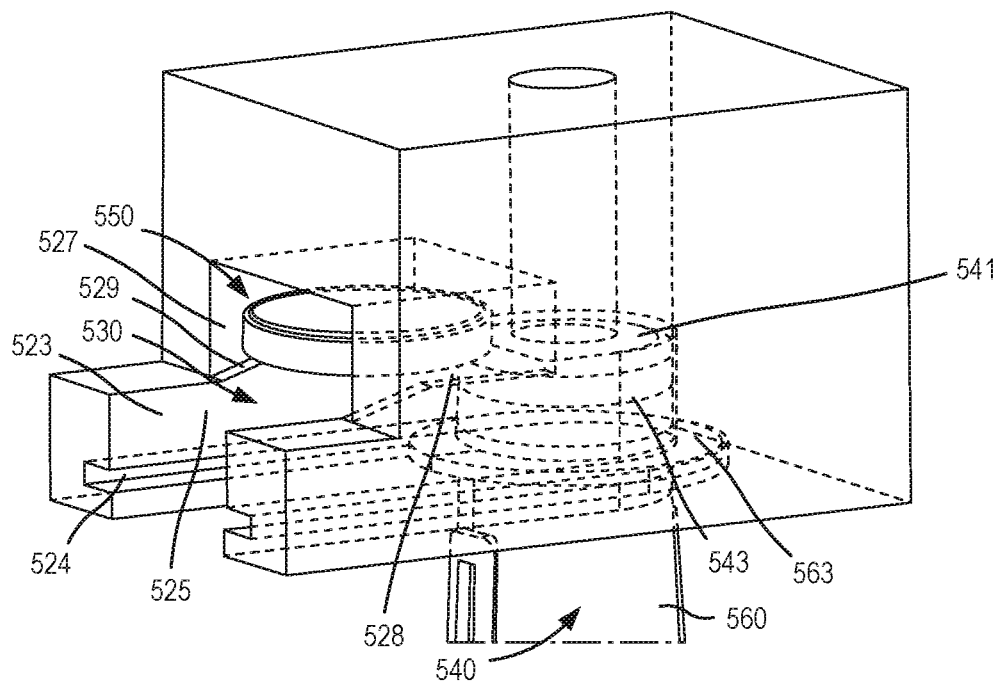

With the sterilization member 550 in contact with the ramp portion 529 of the edge surface 528, further movement of the sterilization member 550 into the inner volume 530 advances the sterilization member 550 relative to the ramp portion 529, which in turn, removes, disengages, peels, and/or otherwise decouples the sterilization member 550 from the fluid reservoir 540, as shown in FIG. 14. As such, the sterilization member 550 is in contact with the edge surface 528 and disposed within a portion of the inner volume 530 defined by the second portion 527 of the inner surface 523. With the sterilization member 550 decoupled from the fluid reservoir 540, the fluid reservoir 540 can be moved within the inner volume 530 relative to the sterilization member 550 and placed in a desired position. For example, the fluid reservoir 540 can be advanced within the inner volume 530 to a depth that is substantially beyond the second portion 527 of the inner surface 523, as shown in FIG. 14.

With the sterilization member 550 decoupled from the fluid reservoir 540, the surface 541 of the fluid reservoir 540 is substantially exposed. In some embodiments, the desired position of the fluid reservoir 540 within the transfer adapter 520 can substantially align a portion of the surface 541 (e.g., a port or other fluidic interface) with a transfer member (e.g., a puncture member such as a sheathed needle or the like). Thus, with the fluid reservoir 540 in the desired position relative to the transfer adapter 520, the user can manipulate the collection device 500 (or portion thereof) to place the transfer adapter 520 in fluid communication with the fluid reservoir 540. For example, in some embodiments, the user can actuate an actuator configured to advance a puncture member or the like through a port or fluidic interface of the surface 541 of the fluid reservoir 540, thereby placing the fluid reservoir 540 in fluid communication with the patient. While not shown, in other embodiments, the physical process of coupling the collection device 500 to the fluid reservoir 540 via the transfer adapter 520 automatically facilitates a flow path for bodily-fluid without specific user manipulation. Thus, the fluid reservoir 540 can receive a flow of bodily-fluid from the patient or intermediary device containing a bodily fluid.

As described above with reference to the collection device 300, the arrangement of the collection device 500 (or portion thereof) is such that the sterility of at least the surface 541 of the fluid reservoir 540 is maintained until a time relatively shortly before the transfer adapter 520 is placed in fluid communication with the fluid reservoir 540. Thus, by maintaining the sterility of a fluidic interface between the transfer adapter 520 and the fluid reservoir 540 until a relatively short time before placing the transfer adapter 520 in fluid communication with the fluid reservoirs, the probability of external contaminants being transferred into the bodily-fluid sample received by the fluid reservoir 540 can be reduced. Moreover, pre-sterilizing fluidic interfaces and automatically exposing those fluidic interfaces just before establishing fluid communication between the transfer adapter 520 and the fluid reservoir 540 can increase compliance with sterilization protocols and ease of performing the procedure, as well as reduce costs and inadvertent mistakes.

Figure 15:
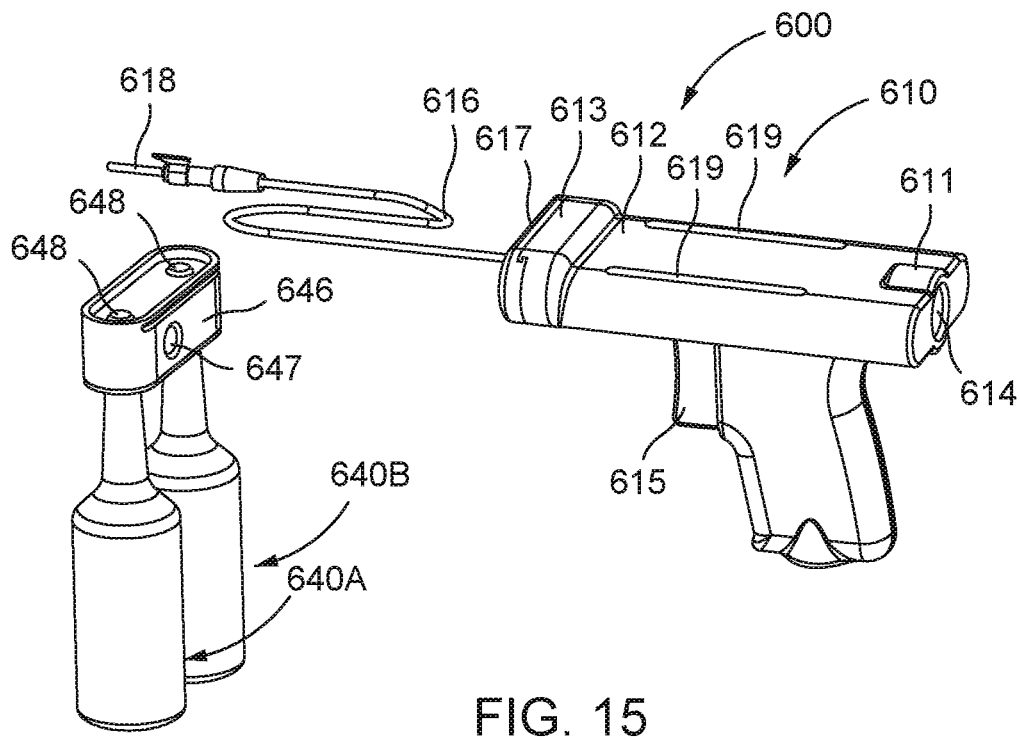
FIGS. 15-17 are perspective views of a bodily-fluid collection device in a first, a second, and a third configuration, respectively, according to an embodiment.
Figure 16:
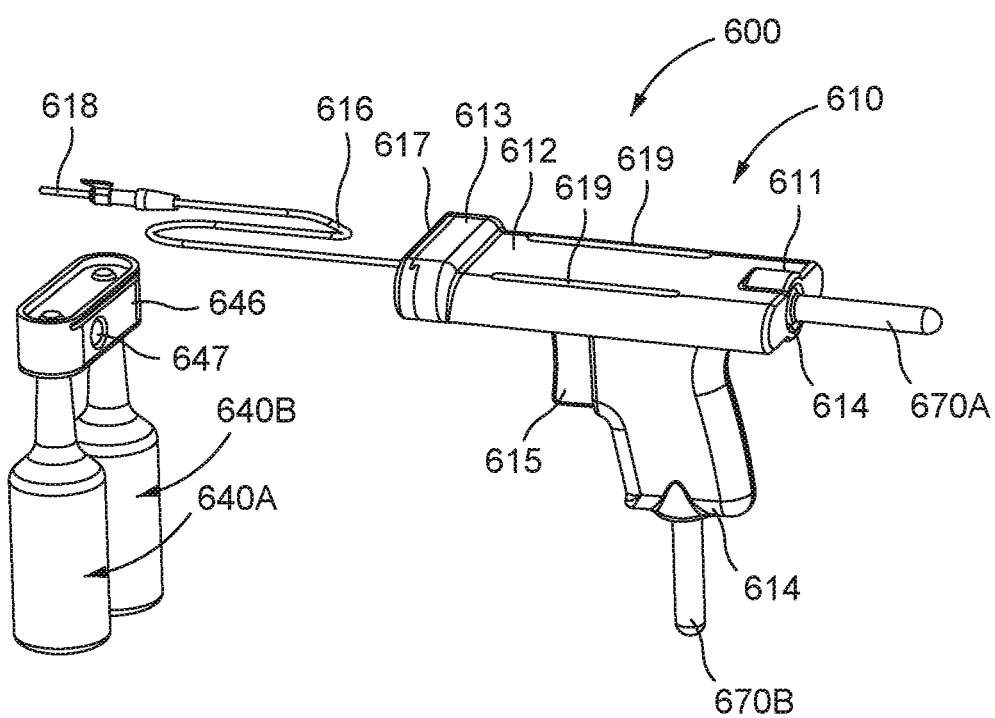
Figure 17:
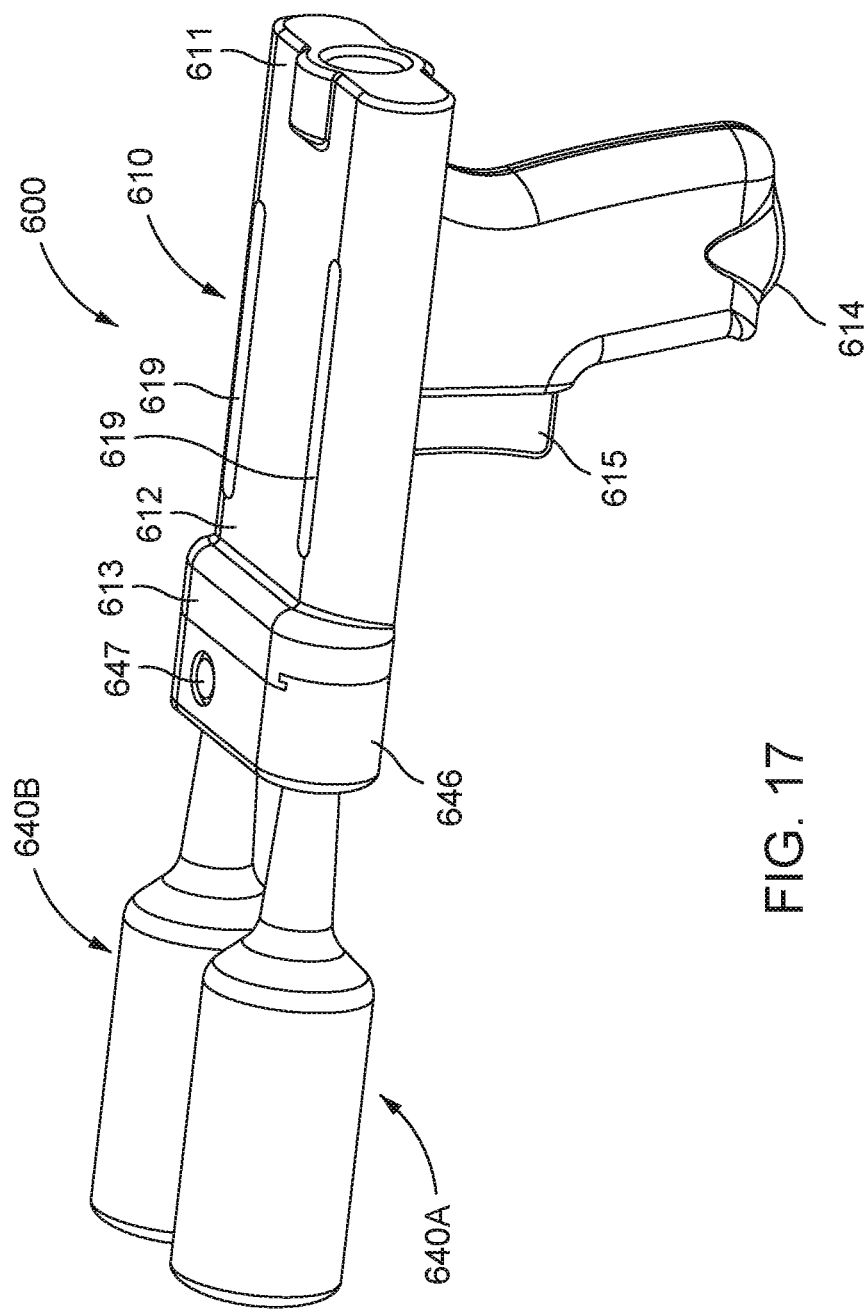

As described above, the transfer adapters 120, 220, 320, 420, and 520 can be included in and/or coupled to any suitable device configured to receive a fluid of bodily-fluid from a patient. Such devices can be any suitable collection device, transfer device, diversion device, and/or the like. For example, FIGS. 15-17 illustrate a collection device 600 according to an embodiment. The collection device 600 can be any suitable device configured to withdraw and/or receive bodily-fluid from a patient. Moreover, the collection device 600 can be used in conjunction with any of the transfer adapters, sterilization members, and/or fluid reservoirs described herein. In other embodiments, the arrangement of the collection device 600 can minimize fluid interfaces or the like, which in turn, can reduce a likelihood of a sample becoming contaminated by external contaminants.

As shown in FIGS. 15-17, the collection device 600 includes and/or forms a handle 610 having a proximal end portion 611 and a distal end portion 612. The distal end portion 612 of the handle 610 can include and/or can be coupled to any suitable port 614 or the like configured to be placed in fluid communication with one or more fluid reservoirs. For example, as shown in FIG. 16, the proximal end portion 611 of the handle 610 includes at least two ports 614 configured to be physically and fluidically coupled to one or more fluid reservoirs 670A and 670B. The fluid reservoirs 670A and/or 670B can be, for example, evacuated reservoirs such as a Vacutainer® or the like. In some embodiments, the fluid reservoirs 670A and/or 670B can be configured to receive a pre-sample volume of bodily-fluid that can contain, for example, dermally-residing microbes, external contaminants or the like. In other embodiments, the fluid reservoirs 670A and/or 670B can receive a sample volume of bodily-fluid, which subsequently can be used in any suitable testing process or the like.

The distal end portion 612 includes a coupler 613 or the like configured to be physically and fluidically coupled to any suitable transfer adapter such as, for example, those described herein. In other embodiments, the coupler 613 can form an integrated transfer adapter or the like. As such, the coupler 613 is configured to be at least indirectly physically and fluidically coupled to any suitable device and/or mechanism configured to transfer bodily-fluid to and/or from the collection device 600, as described in further detail herein.

The handle 610 also includes a system actuator 615 configured to initiate, modulate, divert, and/or otherwise control a flow of the bodily-fluid through the handle 610. Although not shown in FIGS. 15-17, the handle 610 can include any suitable internal component, mechanism, reservoir, or the like configured to facilitate the transfer of bodily-fluid through the handle 610. For example, in some embodiments, the system actuator 615 can be coupled to and/or otherwise include any suitable device, mechanism, assembly, member, etc. operable in selectively limiting, controlling, regulating, diverting, etc. a flow of the bodily-fluid. Specifically, although not shown in FIGS. 15-17, the handle 610 can include any suitable flow control mechanism that can control a flow of the bodily-fluid into and/or from one or more fluid reservoirs 619 disposed within the handle 610. In some embodiments, such a flow control mechanism can be any of those described in the '241 patent, the '724 patent, the '864 patent, and/or the '495 patent, each of which is incorporated by reference above. In some embodiments, such fluid reservoirs 619 can be, for example, evacuated containers or the like such as a Vacutainer®. In other embodiments, the system actuator 615 can include a plunger or the like that can move inside a fluid reservoir to increase an inner volume of the fluid reservoir. The increase in volume can produce a negative pressure within the inner volume of the fluid reservoir, which in turn, can draw bodily-fluid into the fluid reservoir. In some embodiments, actuating the system actuator 615 can be operable in diverting a pre-sample volume of bodily-fluid into a pre-sample reservoir (not shown) and once transferred, sequestering the pre-sample volume of bodily-fluid within the pre-sample reservoir. In this manner, a subsequent volume of bodily-fluid withdrawn from the patient into the fluid reservoirs 619 can be substantially free from dermally-residing microbes, external microbes or other contaminants sequestered in the pre-sample reservoir. In some embodiments, actuating the system actuator 615 can be operable in diverting a pre-sample volume of bodily-fluid into, for example, at least one of the fluid reservoirs 670A and/or 670B.

The coupler 613 of the handle 610 can be coupled to any suitable device. For example, as shown in FIGS. 15 and 16, the coupler 613 is coupled to a lumen-defining device 616 such as sterile flexible tubing. The lumen-defining device 616 can include a needle 618 or cannula disposed at a first end of the lumen-defining device 616 that is configured to puncture or pierce the skin of a patient to place the lumen-defining device 616 in fluid communication with the patient. While not shown, in other embodiments, the lumen-defining device 616 can be substantially similar to standard peripheral IV catheter, which can facilitate access to a patient's bloodstream and/or other bodily-fluid source. The lumen-defining device 616 also includes an adapter 617 at a second end that can physically and fluidically couple the lumen-defining device 616 to the coupler 613 of the handle 610. The adapter 617 and the coupler 613 can be coupled in any suitable manner such as, for example, a press fit, a friction fit, a set of tabs, and/or the like. In some embodiments, the coupler 613 can define a set of channels or the like within which a portion of the adapter 617 can be inserted. In such embodiments, the portion of the adapter 617 can be inserted in to the channels of the coupler 613 and slid therein to a desired position relative to the handle 610. As described above with reference to the housing 345, in some embodiments, the adapter 617 can include a sterilization member or the like that can be transitioned, for example, from a first configuration, in which the sterility of an interface of the adapter 617 is maintained, to a second configuration, in which at least a portion of the sterilization member is removed from the adapter 617. Moreover, coupling the adapter 617 to the coupler 613 can place the handle 610 in fluid communication with the lumen-defining device 616. Thus, bodily-fluid can be transferred from a patient to the fluid reservoirs 619 disposed within the handle 610 in response to, for example, a user actuating the system actuator 615.

In a similar manner, the coupler 613 can be at least indirectly coupled to one or more fluid reservoirs 640A and/or 640B. For example, as shown in FIG. 17, the adapter 617 coupled to the lumen-defining device 616 can be removed from the coupler 613 and an adapter 646 coupled to the fluid reservoirs 640A and 640B can be coupled to the coupler 613. In some embodiments, the adapter 646 can be coupled to the coupler 613 in a substantially similar manner as described with reference to the adapter 617. Thus, when the adapter 646 is coupled to the coupler 613, the fluid reservoirs 640A and/or 640B can be placed in fluid communication with, for example, one or more fluid reservoirs within the handle 610.

As shown in FIG. 17, the adapter 646 is coupled to and/or disposed about at least a portion of the fluid reservoirs 640A and 640B. In some embodiments, the adapter 646 can be similar in form and/or function to, for example, the housing 345 shown in FIGS. 3 and 4. In this manner, the adapter 646 can include a sterilization member or the like configured to define at least a portion of a sterile environment within which at least the portion of the fluid reservoirs 640A and 640B can be disposed, as described above with reference to the housing 345 and the sterilization member 350 of FIGS. 3 and 4.

In some embodiments, the adapter 646 can include an actuator 647, which can direct a flow of bodily-fluid from the fluid reservoir(s) 619 within the handle 610 and through the adapter 646 when actuated. In other words, the actuator 647 of the adapter 646 can selectively place the fluid reservoirs 640A and/or 640B in fluid communication with the coupler 613 of the handle 610. In some embodiments, coupling the adapter 646 to the coupler 613 can automatically establish fluid communication between the fluid reservoirs 640A and/or 640B and the handle 610. For example, in some embodiments, the coupler 613 can include one or more puncture members configured to puncture a portion of the adapter 646 and the fluid reservoir(s) 640A and 640B when the adapter 646 is coupled thereto. In other embodiments, the coupling of the adapter 646 to the coupler 613 at least partially removes and/or decouples a sterilization member such that an inlet surface, interface, and/or the like of the fluid reservoir(s) 640A and/or 640B is unobstructed. In such embodiments, the puncture members of the coupler 613 need not puncture a portion of the adapter 646 in conjunction with and/or prior to puncturing, for example, an inlet surface of the fluid reservoirs 640A and/or 640B. Thus, bodily-fluid stored within the fluid reservoir(s) 619 in the handle 610 can be transferred to the fluid reservoirs 640A and/or 640B, which in turn, can be used in any suitable testing and/or analysis process.

In some instances, reducing a number of fluidic interfaces along a fluid flow path can reduce a likelihood of contaminants being transferred into a volume of bodily-fluid flowing within the fluid flow path. Thus, the modular arrangement of the collection device 600 can result in a reduction of contaminants in the bodily-fluid that is ultimately transferred into the fluid reservoirs 640A and/or 640B. Although not shown in FIGS. 15-17, any of the components (e.g., the coupler 613 and/or the adapters 617 and 646) can include any suitable sterilization member such as those described above. As such, the sterility of the fluidic interfaces can be maintained until the collection device 600 is placed in a configuration associated with transferring a bodily-fluid to and/or from the handle 610. Additionally, at least some or all of the components depicted in FIGS. 15-17 can be pre-assembled during a manufacturing process and sterilized using standard medical techniques (e.g. ethylene oxide, gamma radiation, e-beam or the like) to maintain sterility of the enclosed collection device and/or sample reservoirs.

FIGS. 18-21 illustrate a collection device 700 according to another embodiment. The collection device 700 can be any suitable device configured to withdraw and/or receive bodily-fluid from a patient. Moreover, the collection device 700 can be used in conjunction with any of the transfer adapters, sterilization members, and/or fluid reservoirs described herein. In some embodiments, the arrangement of the collection device 700 can minimize fluid interfaces or the like, which in turn, can reduce a likelihood of a sample becoming contaminated by external contaminants. Some aspects of the collection device 700 can be substantially similar in form and/or function to the associated aspects of the collection device 600 described above with reference to FIGS. 15-17. Thus, such similar aspects are not described in further detail herein.

As shown in FIGS. 18-21, the collection device 700 includes and/or forms a handle 710 having a proximal end portion 711 and a distal end portion 712. The handle 710 also includes a system actuator 715 configured to initiate, modulate, divert, and/or otherwise control a flow of the bodily-fluid through the handle 710 and one or more fluid reservoirs 719 configured to receive and at least temporarily store a volume of bodily-fluid. Although not shown in FIGS. 18-21, the handle 710 can include any suitable internal component, mechanism, device, or the like configured to facilitate the transfer of bodily-fluid through the handle 710, as described in detail above with reference to the handle 610.

The proximal end portion 711 of the handle 710 can include and/or can be coupled to any suitable port or the like configured to be placed in fluid communication with the fluid reservoir(s) 719 disposed within the handle 710, as described above with reference to the handle 610. The distal end portion 712 includes a coupler 713 or the like configured to be physically and fluidically coupled to any suitable transfer adapter such as, for example, those described herein. In other embodiments, the coupler 713 can form an integrated transfer adapter or the like. As such, the coupler 713 is configured to be at least indirectly physically and fluidically coupled to any suitable device and/or mechanism configured to transfer bodily-fluid to and/or from the collection device 700, as described in further detail herein.

Figure 18:
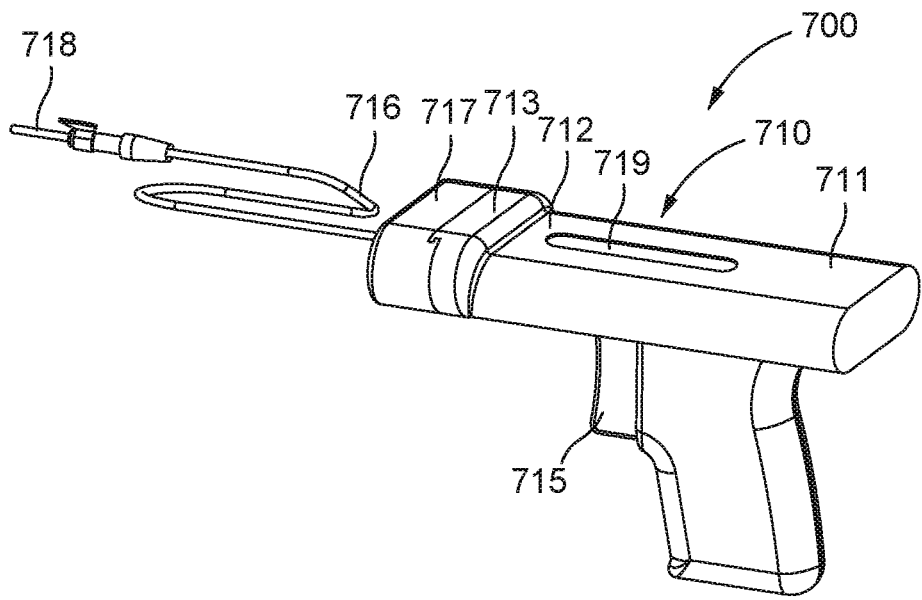
FIGS. 18-20 are perspective views of a bodily-fluid collection device in a first, a second, and a third configuration, respectively, according to another embodiment.
Figure 19:
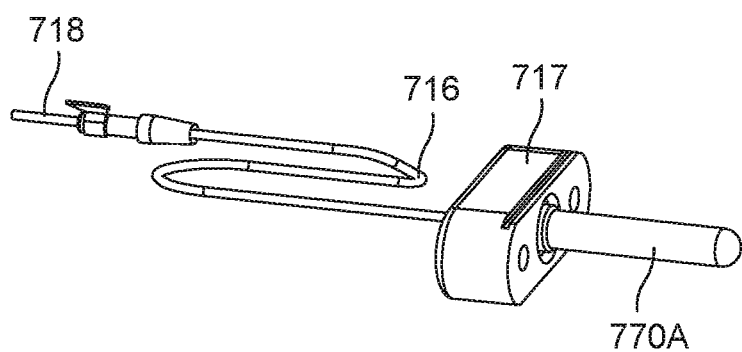

The coupler 713 of the handle 710 can be coupled to any suitable device. For example, as shown in FIGS. 18 and 19, the coupler 713 is coupled to a lumen-defining device 716 such as sterile flexible tubing. The lumen-defining device 716 can include a needle 718 or cannula disposed at a first end of the lumen-defining device 716 that is configured to puncture or pierce the skin of a patient to place the lumen-defining device 716 in fluid communication with the patient. While not shown, in other embodiments, the lumen-defining device 716 can be substantially similar to standard peripheral IV catheter, which can facilitate access to a patient's bloodstream and/or other bodily-fluid source. The lumen-defining device 716 also includes an adapter 717 at a second end configured to be physically and fluidically coupled to the coupler 713 of the handle 710. The adapter 717 and the coupler 713 can be coupled in any suitable manner such as, for example, a press fit, a friction fit, a set of tabs, and/or the like. In some embodiments, the coupler 713 can define a set of channels or the like within which a portion of the adapter 717 can be inserted. As described in detail above with reference to the collection device 600, coupling the adapter 717 to the coupler 713 can place the handle 710 in fluid communication with the lumen-defining device 716. Thus, bodily-fluid can be transferred from a patient to the fluid reservoir(s) 719 in response to, for example, a user actuating the system actuator 715.

As shown in FIG. 19, a fluid reservoir 770A (e.g., an external fluid reservoir and/or a pre-sample reservoir) can be coupled to the adapter 717 prior to the adapter 717 being coupled to the coupler 713 and/or after the adapter 717 is removed from the coupler 713. In other words, the fluid reservoir 770A can be a pre-sample reservoir or the like configured to receive a pre-sample volume of bodily-fluid. In some instances, transferring a volume of bodily-fluid to the fluid reservoir 770A prior to coupling the adapter 717 to the coupler 713 can, for example, entrain contaminants within the flow of bodily-fluid, which in turn, can be sequestered in the fluid reservoir 770A. In such instances, once a desired volume of bodily-fluid is transferred into the fluid reservoir 770A, the fluid reservoir 770A can be removed from the adapter 717, which can then be coupled to the coupler 713. Thus, by sequestering a first volume of bodily-fluid in the fluid reservoir 770A, a subsequent volume of bodily-fluid transferred to one or more fluid reservoir(s) 719 disposed within the handle 710 can be substantially free from dermally-residing microbes, external contaminants, or the like. In other embodiments, the fluid reservoir 770A can receive a volume of bodily-fluid that can be used for additional testing and/or the like.

Figure 20:
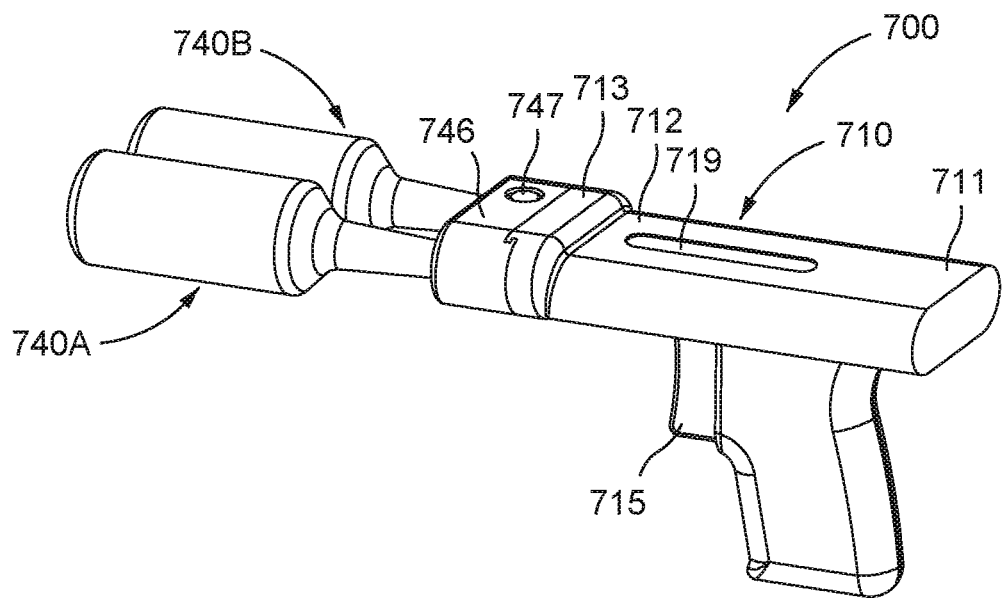

As described above with reference to the collection device 600, after a volume of bodily-fluid is transferred to the fluid reservoir(s) 719 disposed within the handle 710, the coupler 713 can be at least indirectly coupled to one or more fluid reservoirs 740A and/or 740B (e.g., external fluid reservoirs and/or sample reservoirs). For example, as shown in FIG. 20, the adapter 717 coupled to the lumen-defining device 716 can be removed from the coupler 713 and an adapter 746 coupled to the fluid reservoirs 740A and 740B can be coupled to the coupler 713. In some embodiments, the adapter 746 can be coupled to the coupler 713 in a substantially similar manner as described with reference to the adapter 717. In some embodiments, the adapters 717 and/or 746 can include and/or can be at least temporarily coupled to a sterilization member configured to maintain the sterility of, for example, an interface of the adapters 717 and/or 746 prior to being coupled to the coupler 713, as described above with reference to the adapters 617 and 646.

When the adapter 746 is coupled to the coupler 713, the fluid reservoirs 740A and/or 740B can be placed in fluid communication with, for example, the one or more fluid reservoirs 719 within the handle 710. As described above, the adapter 746 can include an actuator 747 that can direct a flow of bodily-fluid from the fluid reservoir(s) 719 within the handle 710 and through the adapter 746 when actuated. In other words, the actuator 747 of the adapter 746 can selectively place the fluid reservoirs 740A and/or 740B in fluid communication with the coupler 713 and/or the fluid reservoirs 719 within the handle 710. Thus, bodily-fluid stored within the fluid reservoir(s) 719 in the handle 710 can be transferred to the fluid reservoirs 740A and/or 740B, which in turn, can be used in any suitable testing and/or analysis process, as described above with reference to the collection device 600.

Figure 21:
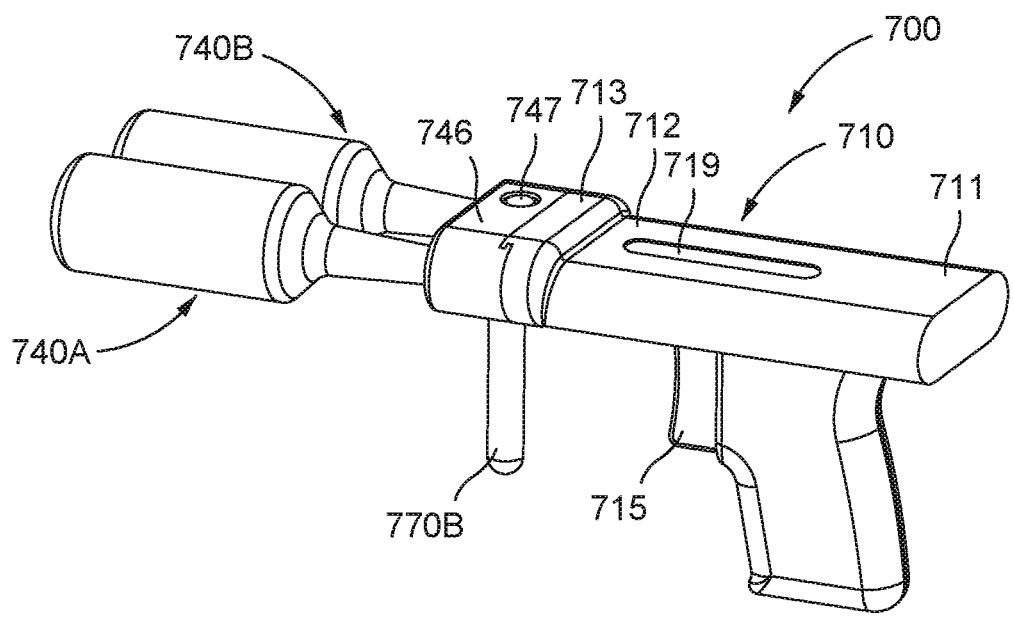
FIG. 21 is a perspective view of the bodily-fluid collection device of FIG. 18 in, for example, in an optional fourth configuration.

As shown in FIG. 21, in some embodiments, an additional reservoir 770B can be physically and fluidically coupled to the adapter 746. For example, in some instances, a relatively large volume of bodily-fluid can be withdrawn from the patient, which can, for example, allow for the additional fluid reservoir 770B to be coupled to the adapter 746. Thus, a volume of the bodily-fluid can be transferred into the additional fluid reservoir 770B that can subsequently be used for additional testing or the like. Moreover, in some embodiments, the actuator 747 included in the adapter 746 can be configured to control a flow of bodily fluid from the reservoir(s) disposed within the handle 710 to the fluid reservoirs 740A, 740B, and/or 770B.

Figure 22:
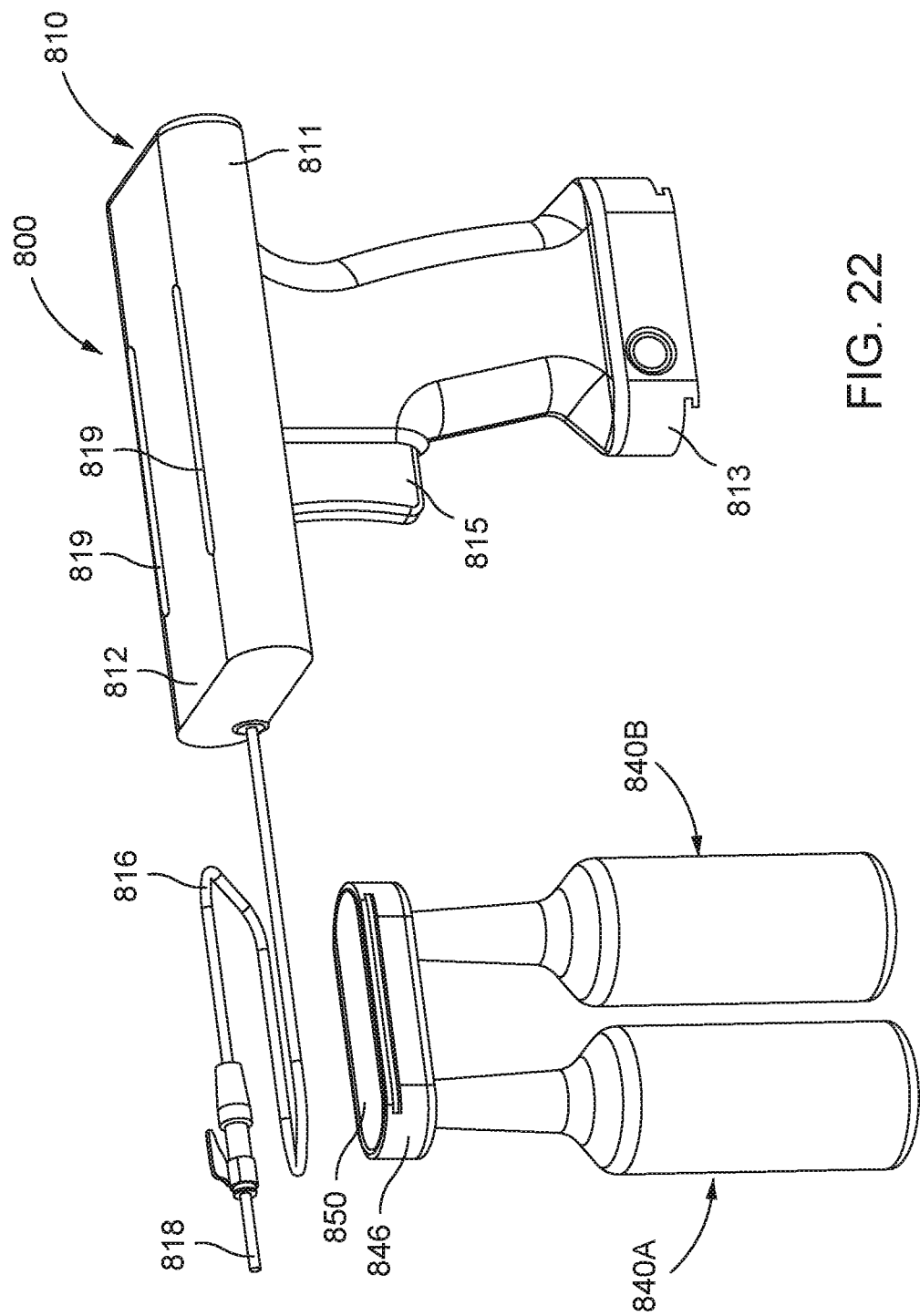
FIGS. 22-24 are perspective views of a bodily-fluid collection device in a first, a second, and a third configuration, respectively, according to another embodiment.
Figure 23:
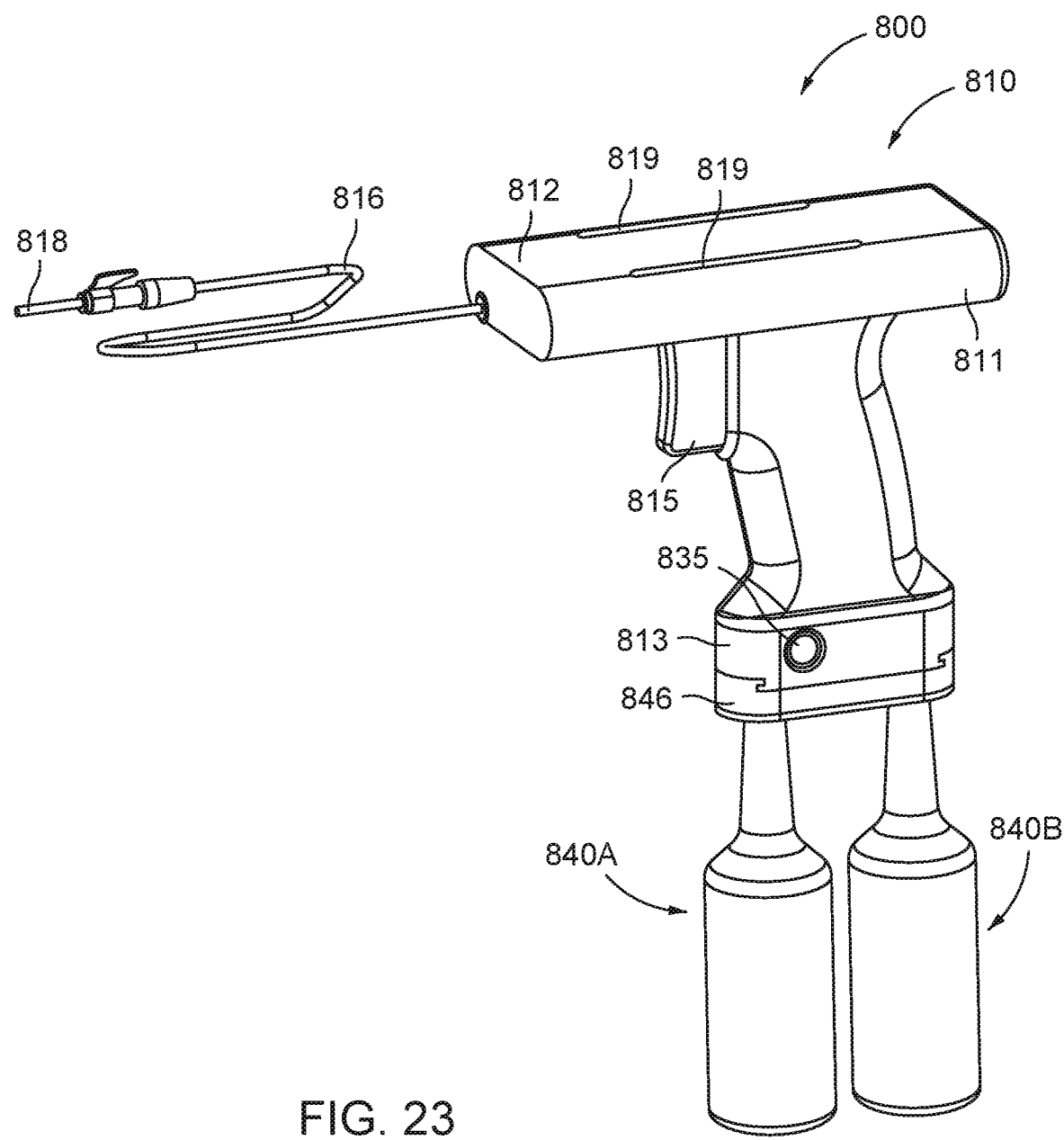
Figure 24:
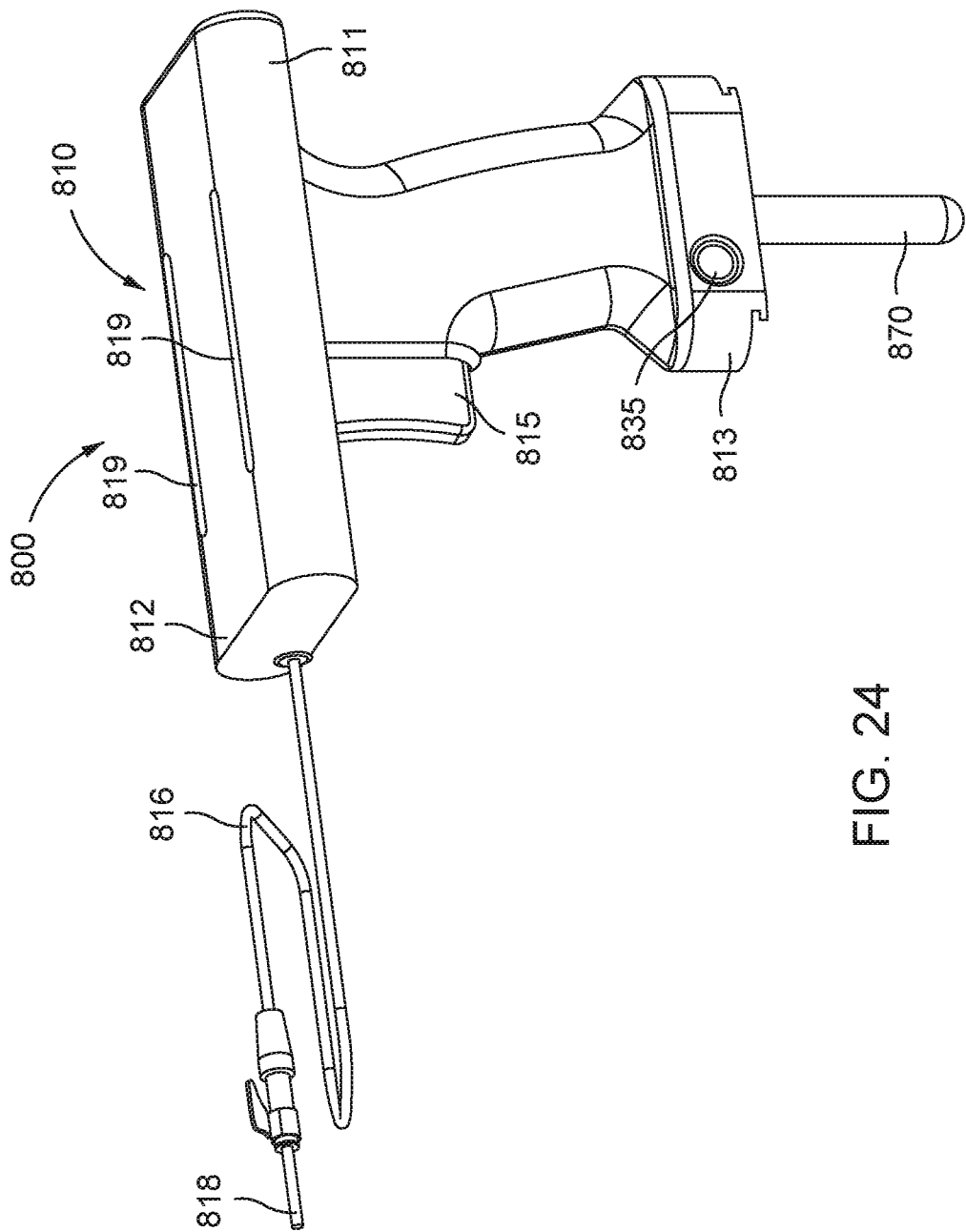

FIGS. 22-24 illustrate a collection device 800 according to another embodiment. The collection device 800 can be any suitable device configured to withdraw and/or receive bodily-fluid from a patient. Moreover, the collection device 800 can be used in conjunction with any of the transfer adapters, sterilization members, and/or fluid reservoirs described herein. In some embodiments, the arrangement of the collection device 800 can minimize fluid interfaces or the like, which in turn, can reduce a likelihood of a sample becoming contaminated by external contaminants. Some aspects of the collection device 800 can be substantially similar in form and/or function to the associated aspects of the collection device 600 and/or 700 described above with reference to FIGS. 15-17 and FIGS. 18-21, respectively. Thus, such similar aspects are not described in further detail herein.

The collection device 800 includes and/or forms a handle 810 having a proximal end portion 811 and a distal end portion 812. The proximal end portion 811 of the handle 810 can include and/or can be coupled to any suitable port or the like configured to be placed in fluid communication with one or more fluid reservoirs, as described above with reference to the handle 610. As shown, the distal end portion 812 of the handle 810 is physically and fluidically coupled to a lumen-defining device 816 such as sterile flexible tubing. The lumen-defining device 816 can include a needle 818 or cannula disposed at a first end of the lumen-defining device 816 that is configured to puncture or pierce the skin of a patient to place the lumen-defining device 816 in fluid communication with the patient. A second end of the lumen-defining device 816 is fixedly coupled to the distal end portion 812 of the handle 810. That is to say, the lumen-defining device 816 can be integrated into the handle 810 and/or otherwise not coupled to an adapter, which in turn, would otherwise be coupled to a coupler of the handle 810 (e.g., as described above with reference to the lumen-defining devices 616 and 716). Thus, as described in detail above with reference to the collection devices 600 and 700, the lumen-defining device 816 can transfer bodily-fluid from a patient to one or more fluid reservoir(s) 819 disposed within the handle 810, as described in further detail herein.

The handle 810 also includes a coupler 813 and a system actuator 815. The system actuator 815 is configured to initiate, modulate, divert, and/or otherwise control a flow of the bodily-fluid through the handle 810. Although not shown in FIGS. 22-24, the handle 810 can include any suitable internal component, mechanism, device, fluid reservoir, or the like configured to facilitate the transfer of bodily-fluid through the handle 810, as described in detail above with reference to the handle 610. Thus, actuating the system actuator 815 can transfer bodily-fluid from a patient, through the lumen-defining device 816, and into the one or more fluid reservoirs 819 disposed within the handle 810.

As described above with reference to the collection devices 600 and 700, the coupler 813 is configured to be physically and fluidically coupled to any suitable transfer adapter such as, for example, those described herein. In other embodiments, the coupler 813 can form an integrated transfer adapter or the like. While the couplers 613 and 713 are shown and described above as being included in and/or disposed at a distal end portion 612 and 712, respectively, of the handles 610 and 710, respectively, in the embodiment shown in FIGS. 22-24, the coupler 813 can be disposed at or near the proximal end portion 811 of the handle 810 and/or at any other suitable location along the handle 810 (e.g., along a top surface of the handle 810, a bottom surface of the handle 810, and/or along a side surface of the handle 810).

The coupler 813 is configured to be physically and fluidically coupled (at least indirectly) to any suitable device and/or mechanism configured to transfer bodily-fluid to and/or from the collection device 800. For example, as shown in FIGS. 22 and 23, the coupler 813 can be at least indirectly coupled to one or more fluid reservoirs 840A and/or 840B. More specifically, an adapter 846 coupled to the fluid reservoirs 840A and 840B can be coupled to the coupler 813. In some embodiments, the adapter 846 can be coupled to the coupler 813 in a substantially similar manner as described above with reference to the adapter 646. In some embodiments, the adapter 846 can include and/or can be at least temporarily coupled to a sterilization member configured to maintain the sterility of, for example, an interface of the adapter 846 prior to being coupled to the coupler 813, as described above with reference to the adapters 617 and 646. Thus, when the adapter 846 is coupled to the coupler 813, the fluid reservoirs 840A and/or 840B can be placed in fluid communication with, for example, one or more fluid reservoirs 819 within the handle 810.

Although the adapters 646 and 746 are described above as having an actuator, in the embodiment illustrated in FIGS. 22-24, the coupler 813 of the handle 810 includes an actuator 835. As described above, the actuator 835 can be configured to direct a flow of bodily-fluid from the fluid reservoir(s) within the handle 810 and through the adapter 846. In other words, the actuator 835 of the coupler 813 can selectively place the fluid reservoirs 840A and/or 840B in fluid communication with the handle 810. Thus, bodily-fluid stored within the fluid reservoir(s) 819 in the handle 810 can be transferred to the fluid reservoirs 840A and/or 840B, which in turn, can be used in any suitable testing and/or analysis process, as described above with reference to the collection device 600.

As described above with reference to the portion of the collection device 300, the embodiment shown in FIGS. 22-24 includes a sterilization member 850 coupled to the adapter 846. For example, the sterilization member 850 can be a sheet, film, foil, wipe, seal, and/or the like configured to at least temporarily fluidically isolate a portion the adapter 846. Thus, as described above, the sterilization member 850 can be configured to seal the adapter 846 to maintain a portion of the fluid reservoirs 840A and 840B in a substantially sterile environment prior to use. In some embodiments, coupling the adapter 846 to the coupler 813 can include disposing at least a portion of the sterilization member 850 through a set of channels or the like (not shown). As described in detail above with reference to the sterilization member 350, a surface of the coupler 813 defining at least a portion of the channels can engage the sterilization member 850 to remove at least a portion of the adapter 846. Thus, a portion of the fluid reservoirs 840A and 840B can be exposed and placed in fluid communication with the handle 810, as described above.

As shown in FIG. 24, in some embodiments, an additional reservoir 870 can be physically and fluidically coupled to the coupler 813. For example, in some instances, a relatively large volume of bodily-fluid can be withdrawn from the patient, which can, for example, allow for the additional fluid reservoir 870 to be coupled to the coupler 813. Thus, a volume of the bodily-fluid can be transferred into the additional fluid reservoir 870 that can subsequently be used for additional testing or the like. In other embodiments, the additional fluid reservoir 870 can be coupled to the adapter 846. In some embodiments, the actuator 835 included in the coupler 813 can be configured to control a flow of bodily fluid from the reservoir(s) 819 disposed within the handle 810 to the fluid reservoirs 840A, 840B, and/or 870.

In some embodiments, the actuator 815 can be configured to remain in a locked configuration until a volume of bodily-fluid is transferred into, for example, the fluid reservoir 870 (e.g., a pre-sample reservoir). Thus, in some instances, contaminants contained in a fluid flow path defined between the fluid reservoir(s) 819 within the handle 810 and the coupler can be transferred into the fluid reservoir 870. In such instances, after the volume of bodily-fluid is transferred into the fluid reservoir 870, the fluid reservoir 870 can be removed from the coupler 813, which in turn, can sequester the contaminants in the fluid reservoir 870. Thus, subsequent volumes of bodily-fluid transferred to the fluid reservoirs 840A and/or 840B can be substantially free from contaminants. Moreover, disposing the actuator 815 in a locked configuration prior to a volume of bodily-fluid being transferred into the fluid reservoir 870 can ensure a user first collects the volume of bodily-fluid in the fluid reservoir 870, which can reduce an amount of contaminants transferred into the fluid reservoirs 840A and 840B, as described above.

While the handles 610, 710, and 810 are each described above as including the coupler 613, 713, and 813, respectively, that is configured to couple to an adapter, in other embodiments, a handle can include multiple couplers each of which can be coupled to an adapter. For example, in some embodiments, a handle can include a first coupler disposed at, for example, a distal end portion of the handle (e.g., similar to the couplers 613 and 713 described above). The first coupler can be configured to couple to an adapter in fluid communication with, for example, a lumen-defining device that can be placed in fluid communication with one or more fluid reservoirs disposed within the handle when coupled to the first coupler. The handle can also include a second coupler disposed at, for example, a proximal end portion of the handle (e.g., similar to the coupler 813 described above). The second coupler can be configured to couple to an adapter in fluid communication with, for example, one or more sample reservoirs that can be placed in fluid communication with the one or more fluid reservoirs disposed within the handle when coupled to the second coupler. In such embodiments, a volume of bodily-fluid can be transferred from the patient into the one or more fluid reservoirs within the handle, as described above with reference to the handles 610, 710, and/or 810. A volume of the bodily-fluid within the one or more fluid reservoirs within the handle can then be transferred into the sample reservoirs coupled to the second coupler, as described above with reference to the handles 610, 710, and/or 810.

Figure 25:
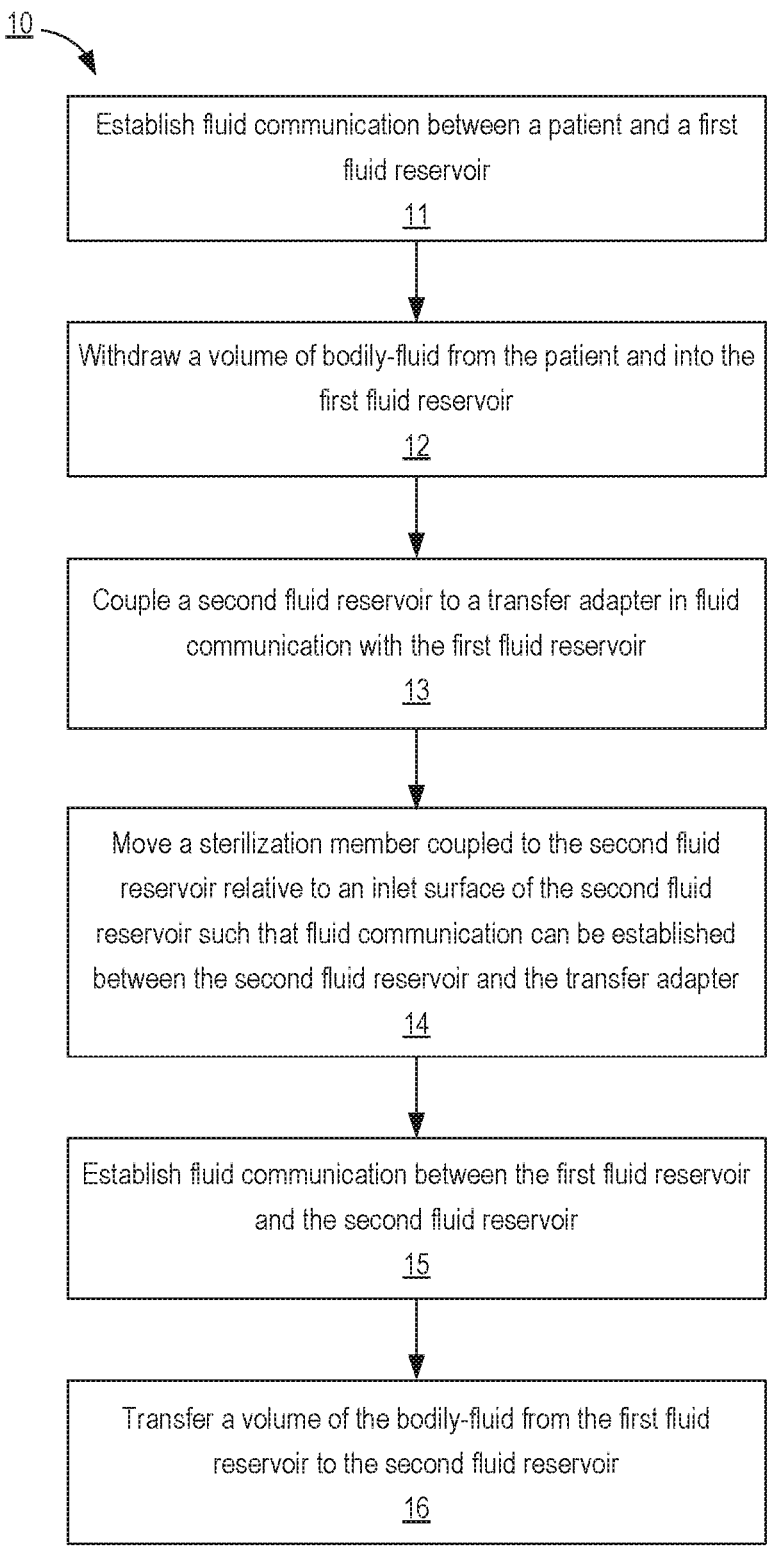
FIG. 25 is a flowchart illustrating a method of parentally-procuring bodily-fluid samples with reduced contamination, according to an embodiment.

FIG. 25 is a flowchart illustrating a method 10 of parentally-procuring bodily-fluid samples with reduced contamination, according to an embodiment. The method 10 includes establishing fluid communication between a patient and a first fluid reservoir, at 11. The first fluid reservoir can be any suitable fluid reservoir such as those described herein. In some embodiments, for example, the first fluid reservoir can be a fluid reservoir disposed within a handle (e.g., the handles 610, 710, and/or 810) and/or any other suitable fluid transfer device.

In some embodiments, the first fluid reservoir can be in fluid communication with a lumen-defining device or the like that defines at least a portion of a fluid flow path between the patient and the first fluid reservoir. For example, the lumen-defining device can be coupled to and/or can include a needle at a first end and can be coupled to the first fluid reservoir and/or other suitable flow path at a second end (e.g., opposite the first end), as described above with reference to the collection device 800. In some embodiments, the lumen-defining device can be coupled to and/or included in an adapter or the like configured to couple to a portion of a fluid transfer device that includes the first fluid reservoir, as described above with reference to the collection devices 600 and/or 700. In some embodiments, fluid communication between the first fluid reservoir and the lumen-defining device (and thus, the patient) can be in response to, for example, an actuation of an actuator or the like, as described above with reference to the collection devices 600, 700, and/or 800.

Once fluid communication is established between the first fluid reservoir and the patient, a volume of bodily-fluid can be withdrawn from the patient and into the first fluid reservoir, at 12. Alternatively, as described above, the method 10 can optionally include withdrawing a pre-sample volume of bodily-fluid into one or more pre-sample reservoirs prior to transferring the volume of bodily-fluid to the first fluid reservoir. The pre-sample volume can then be sequestered in the pre-sample volume prior to transferring the bodily-fluid to the first fluid reservoir. In some instances, transferring bodily-fluid to the first fluid reservoir can be blocked and/or substantially prevented until a pre-sample volume has been sequestered in a pre-sample reservoir.

With the volume of bodily-fluid contained in the first fluid reservoir, a second fluid reservoir is coupled to a transfer adapter in fluid communication with the first fluid reservoir, at 13. The transfer adapter can be any of those described herein. In some embodiments, the transfer adapter can be substantially similar to the coupler 613 described above with reference to FIGS. 15-17. The second fluid reservoir can be any suitable fluid reservoir such as those described herein. In some embodiments, a portion of the second fluid reservoir can be coupled to, for example, a sterilization member or the like configured to maintain the sterility of an inlet surface of the second fluid reservoir. The sterilization member can be substantially similar to any of those described herein. As such, the sterilization member can define at least a portion of a sterile environment in which the inlet surface of the second fluid reservoir is disposed.

The sterilization member is moved relative to the inlet surface of the second fluid reservoir such that fluid communication can be established between the second fluid reservoir and the transfer adapter, at 14. For example, in some embodiments, the transfer adapter can include a surface, a feature, a contour, a protrusion, etc. configured to be placed in contact with the sterilization member as the second fluid reservoir is coupled to the transfer adapter (e.g., occurring at substantially the same time and/or in a single process). In this manner, as the second fluid reservoir moves relative to the transfer adapter to couple thereto, the sterilization member is moved, for example, from a first configuration to a second configuration. In some embodiments, for example, the sterilization member can be at least partially removed from the second fluid reservoir such that the inlet surface is substantially unobstructed, as described in detail above with reference to specific embodiments.

With the inlet surface of the second fluid reservoir substantially unobstructed, fluid communication is established between the first fluid reservoir and the second fluid reservoir, at 15. For example, in some embodiments, a user or the like can actuate an actuator that can be operable to define a fluid flow path between the first fluid reservoir and the second fluid reservoir. In some embodiments, such an actuation of the actuator can, for example, advance one or more puncture members relative to the second fluid reservoir such that a portion of the puncture member punctures or pierces the inlet surface of the second fluid reservoir, as described above. In some embodiments, multiple actuators can be actuated to establish fluid communication between the first fluid reservoir and the second fluid reservoir. Once fluid communication is established between the first fluid reservoir and the second fluid reservoir, a volume of bodily-fluid is transferred from the first fluid reservoir to the second fluid reservoir, at 16. In some instances, maintaining the sterility of at least a portion of the fluid reservoir prior to use and/or maintaining the sterility of one or more interfaces which are coupled to define at least a portion of a fluid flow path, can result in reduced contamination within a sample volume of bodily-fluid transferred to the second fluid reservoir. Similarly, withdrawing a pre-sample volume of bodily-fluid into a pre-sample reservoir and sequestering the pre-sample volume within the pre-sample reservoir can also reduce contaminants that may otherwise be present in a sample volume transferred to the second fluid reservoir.

Any of the embodiments described herein can include components that are manufactured, packaged, and sold independently or collectively. For example, in some instances, any of the embodiments described herein can be manufactured, assembled, and packaged collectively during a manufacturing process. In such instances, one or more sterilization members, such as those described herein, can be positioned within a collection device and/or coupled to a sample reservoir during a manufacturing process (e.g., during assembly), which can be performed, for example, in a substantially sterile environment and/or facilitated using post-manufacturing standard medical sterilization techniques (e.g. ethylene oxide, gamma radiation, e-beam, or the like). Moreover, the position of the sterilization member can be such that during use, a clinician is substantially prevented from collecting and/or transferring a bodily-fluid sample into a fluid reservoir(s) without engaging the sterilization member to at least substantially sterilize a connection between the collection device and the fluid reservoir.

Although not shown, any of the embodiments and/or methods described herein can be used in conjunction with and/or otherwise in the methods described in the '782 publication incorporated by reference above. For example, the embodiments, described herein can be used to collect a bodily-fluid sample, which in turn can be used in any of the testing methods, diagnostic methods, and/or analysis methods described in the '782 publication.

While various embodiments have been described above, it should be understood that they have been presented by way of example only, and not limitation. For example, although not shown, the embodiments and/or methods described herein can be used with any suitable fluid transfer device configured to receive a flow of bodily-fluid from a patient and at least temporarily store and/or otherwise transfer at least a portion of the bodily-fluid to one or more sample reservoirs. Similarly, in some embodiments, such a fluid transfer device can be used to transfer bodily-fluid to a transfer adapter such as those described herein, which in turn, can transfer at least a portion of the bodily-fluid to one or more fluid reservoirs (e.g., sample reservoirs). In some embodiments, such a fluid transfer device can be any of those described in the '241 patent, the '724 patent, the '864 patent, the '495 patent, and/or the '782 publication.

For example, in some instances, the embodiments described herein can be used with a syringe-based fluid transfer device. In some such instances, the use of a syringe-based device can allow a user to manually control a flow of bodily-fluid into a syringe (e.g., the transfer device) by modulating a force exerted on an actuator or plunger. For example, in some instances, a user can control a rate of fluid transfer and/or an amount of negative pressure, which, in the case of drawing a volume of blood, can limit and/or reduce a risk of hemolysis of the volume of blood, a risk of vein collapse, a risk of inaccurate volume collection, and/or the like. In some embodiments, such a syringe-based transfer device can be similar to any of those described in the '495 patent. In some embodiments, once a desired volume of bodily-fluid (e.g., blood) is drawn into the syringe-based device, any of the transfer adapters and/or fluid reservoirs (with or without sterilization members coupled thereto) can be coupled to and/or placed in fluid communication with the syringe-based device such that a desired volume of bodily-fluid can be transferred into one or more fluid reservoirs (e.g., sample reservoirs). In other embodiments, any of the transfer adapters and/or devices described herein can be integrated into and/or otherwise included in a syringe-based transfer device.

While the embodiments have been particularly shown and described, it will be understood that various changes in form and details may be made. Where schematics and/or embodiments described above indicate certain components arranged in certain orientations or positions, the arrangement of components may be modified. Although various embodiments have been described as having particular features and/or combinations of components, other embodiments are possible having a combination of any features and/or components from any of embodiments as discussed above.

By way of example, while the sterilization members 150, 350, 450, 550, 650, 750, and/or 850 have been described above as substantially maintaining the sterility of a surface of a fluid reservoir, in other embodiments, any of the sterilization members described herein can be used to disinfect a surface of a fluid reservoir. For example, in some embodiments, any of the sterilization members can be coupled to a portion of a fluid reservoir in a substantially sterile environment during a manufacturing process or the like such as those described herein. Thus, in such embodiments, the sterilization members can be configured to maintain the sterility of the portion of the fluid reservoir. In other embodiments, however, any of the sterilization members described herein can be coupled to a portion of a fluid reservoir in a non-sterile environment during a manufacturing process and/or by a user prior to use. Thus, in such embodiments, the sterilization members can be configured to disinfect the portion of the fluid reservoir (e.g., an inlet surface or the like) and/or otherwise remove contaminants from the portion of the fluid reservoir. Accordingly, while described above as "sterilization members" configured to maintain the sterility of a portion of a fluid reservoir, it should be understood that such members can be, for example, "disinfection members" configured to disinfect the portion of the fluid reservoir.

The specific configurations of the various components can also be varied. For example, the size and specific shape of the various components can be different from the embodiments shown, while still providing the functions as described herein. More specifically, the size and shape of the various components can be specifically selected for a desired rate of bodily-fluid flow into a fluid reservoir. Similarly, the size and/or specific shape of various components can be specifically selected for a desired fluid reservoir. For example, portions of the embodiments described herein can be modified such that any suitable container, microcontainer, microliter container, vial, microvial, microliter vial, nanovial, sample bottle, culture bottle, tube, syringe, etc. can be placed in contact with a disinfection member to sterilize one or more interfaces associated therewith prior to a bodily-fluid being drawn into a volume so defined.

Where methods and/or events described above indicate certain events and/or procedures occurring in certain order, the ordering of certain events and/or procedures may be modified. Additionally, certain of the events may be performed concurrently in a parallel process when possible, as well as performed sequentially as described above.

What is claimed:

1. An apparatus, comprising:
a fluid reservoir having an inlet surface, the fluid reservoir configured to receive a volume of bodily-fluid transferred from a patient;
a sterilization device operably coupled to the fluid reservoir, the sterilization device including a surface that defines at least a portion of a sterilized environment, the sterilization device configured to be transitioned between a first configuration, in which the surface of the sterilization device obstructs the inlet surface and maintains the inlet surface in the sterilized environment, and a second configuration, in which the inlet surface is unobstructed by the surface of the sterilization device; and
a transfer device including an inlet configured to be placed in fluid communication with a portion of a patient, the transfer device including a set of walls that define an inner volume configured to receive at least a portion of the sterilization device in the first configuration in response to the transfer device being moved relative to the sterilization device from a first position to a second position, a surface of the transfer device configured to contact the sterilization device as the transfer device is moved to the second position to transition the sterilization device to the second configuration, the transfer device defining at least a portion of a flow path that places the inlet of the transfer device in fluid communication with the fluid reservoir when the transfer device is in the second position, wherein the sterilization device member includes a disinfection agent defining at least a portion of the sterilized environment, the sterilization device is coupled to a portion of the fluid reservoir such that the disinfection agent is in contact with the inlet surface.

2. The apparatus of claim 1, further comprising:
a housing defining an inner volume, the housing being coupled to the sterilization device such that the inner volume of the housing forms the sterilized environment when the sterilization device is in the first configuration, the fluid reservoir being disposed within the inner volume of the housing.

3. The apparatus of claim 1, further comprising:
a housing defining an inner volume, the housing being coupled to the sterilization device such that the inner volume of the housing forms the sterilized environment when the sterilization device is in the first configuration, the fluid reservoir being disposed within the inner volume of the housing,
the sterilization device being coupled to the housing when in the first configuration, the sterilization device being at least partially removed from the housing when in the second configuration.

4. The apparatus of claim 3, wherein the sterilization device is at least one of a sheet, a foil, a cap, a membrane, or a diaphragm removably coupled to the housing.

5. The apparatus of claim 1, wherein the sterilization device includes a disinfection agent defining at least a portion of the sterilized environment, the sterilization device is coupled to a portion of the fluid reservoir such that the disinfection agent is in contact with the inlet surface,
the sterilization device defining an opening in fluid communication with the disinfection agent, the sterilization device including a seal member configured to obstruct the opening when the sterilization device is in the first configuration, the surface of the transfer device configured to contact the seal member when the transfer device is moved from the first position to the second position to place the sterilization device in the second configuration, the opening being unobstructed by the seal member when the sterilization device is in the second configuration.

6. The apparatus of claim 1, wherein the sterilization device is removably coupled to a portion of the fluid reservoir, the sterilization device and the portion of the fluid reservoir collectively defining a volume forming at least a portion of the sterilized environment, the inlet surface being disposed within the volume when the sterilization device is in the first configuration,
the surface of the transfer device configured to decouple the sterilization device from the portion of the fluid reservoir to place the sterilization member in the second configuration as the transfer device is placed in the second position.

* * * * *